(12) United States Patent
Hasegawa et al.

(10) Patent No.: US 7,857,752 B2
(45) Date of Patent: Dec. 28, 2010

(54) MEDICAL IMAGE PROCESSING APPARATUS AND MEDICAL IMAGE PROCESSING METHOD

(75) Inventors: Jun Hasegawa, Hino (JP); Hirokazu Nishimura, Hachioji (JP); Hideki Tanaka, Hino (JP); Ryoko Inoue, Hachioji (JP)

(73) Assignee: Olympus Corporation, Tokyo (JP)

( * ) Notice: Subject to any disclaimer, the term of this patent is extended or adjusted under 35 U.S.C. 154(b) by 620 days.

(21) Appl. No.: 11/821,898

(22) Filed: Jun. 26, 2007

(65) Prior Publication Data

US 2008/0097150 A1  Apr. 24, 2008

Related U.S. Application Data

(63) Continuation of application No. PCT/JP2005/023493, filed on Dec. 21, 2005.

(30) Foreign Application Priority Data

| Dec. 27, 2004 | (JP) | ............................. 2004-378011 |
| Jan. 6, 2005 | (JP) | ............................. 2005-001842 |
| Jan. 7, 2005 | (JP) | ............................. 2005-003200 |

(51) Int. Cl.
*A61B 1/04* (2006.01)

(52) U.S. Cl. ....................... 600/109; 600/117; 600/118; 600/407; 600/424

(58) Field of Classification Search ................. 600/109, 600/117–118, 166, 410, 414, 417, 424–426, 600/429, 443, 475, 479; 348/65
See application file for complete search history.

(56) References Cited

U.S. PATENT DOCUMENTS 4,910,590 A * 3/1990 Gillies et al. .................. 348/65

(Continued)

FOREIGN PATENT DOCUMENTS

JP          03-109023          5/1991

(Continued)

OTHER PUBLICATIONS

Okatani, T, et al.; "Reconstructing Shape from Shading with a Point Light Source at the Projection Center-Shape Reconstruction from an Endoscopic Image-" Computer Vision, vol. 98-4, pp. 19-26, 1996.

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A medical image processing apparatus having an image conversion section including a coordinate-system converting section for converting an image in an orthogonal coordinate system to an image in a polar coordinate system, for geometrically converting a medical image of a tubular part in vivo picked up and obtained by the coordinate-system converting section; a squamocolumnar junction detecting section for detecting a squamocolumnar junction that is a junction between a squamous epithelium and a columnar epithelium on the image of the polar coordinate system; and an analyzing section for comparing an evaluation value for a feature value determined for the detected squamocolumnar junction and a predetermined reference value and calculating an analysis result.

31 Claims, 41 Drawing Sheets

U.S. PATENT DOCUMENTS

| | | | | |
|---|---|---|---|---|
| 5,018,509 | A * | 5/1991 | Suzuki et al. | 600/115 |
| 5,432,543 | A * | 7/1995 | Hasegawa et al. | 348/45 |
| 5,469,254 | A * | 11/1995 | Konomura | 356/241.1 |
| 5,469,840 | A * | 11/1995 | Tanii et al. | 600/117 |
| 5,817,019 | A * | 10/1998 | Kawashima | 600/437 |
| 5,841,511 | A * | 11/1998 | D'Souza et al. | 351/212 |
| 5,885,218 | A * | 3/1999 | Teo et al. | 600/443 |
| 6,346,940 | B1 * | 2/2002 | Fukunaga | 345/427 |
| 7,016,539 | B1 * | 3/2006 | Silver et al. | 382/216 |
| 7,197,170 | B2 * | 3/2007 | Dwyer et al. | 382/128 |
| 7,233,820 | B2 * | 6/2007 | Gilboa | 600/427 |
| 7,245,754 | B2 * | 7/2007 | Goto | 382/128 |
| 2003/0103212 | A1 * | 6/2003 | Westphal et al. | 356/479 |
| 2004/0027500 | A1 * | 2/2004 | Davidson et al. | 348/809 |
| 2004/0081340 | A1 * | 4/2004 | Hashimoto | 382/128 |
| 2004/0160440 | A1 * | 8/2004 | Barth | 345/419 |
| 2005/0148847 | A1 * | 7/2005 | Uchiyama et al. | 600/407 |
| 2006/0149134 | A1 * | 7/2006 | Soper et al. | 600/182 |

FOREIGN PATENT DOCUMENTS

| | | |
|---|---|---|
| JP | 04-295326 | 10/1992 |
| JP | 06-007289 | 1/1994 |
| JP | 08-256295 | 10/1996 |
| JP | 11-066316 | 3/1999 |
| JP | 11-299787 | 11/1999 |
| JP | 3347385 | 9/2002 |
| JP | 2003-093328 | 4/2003 |
| JP | 2005-028123 | 2/2005 |
| JP | 2006-166990 | 6/2006 |

OTHER PUBLICATIONS

Office Action mailed Oct. 5, 2010 by the Japan Patent Office.

* cited by examiner

MEDICAL IMAGE PROCESSING APPARATUS AND MEDICAL IMAGE PROCESSING METHOD

CROSS REFERENCE TO RELATED APPLICATION

This application is a continuation application of PCT/JP2005/023493 filed on Dec. 21, 2005 and claims the benefit of Japanese Applications No. 2004-378011 filed in Japan on Dec. 27, 2004, No. 2005-001842 filed in Japan on Jan. 6, 2005, and No. 2005-003200 filed in Japan on Jan. 7, 2005, the entire contents of each of which are incorporated herein by their reference.

BACKGROUND OF THE INVENTION

1. Field of the Invention

The present invention relates to a medical image processing apparatus and medical image processing method for performing image processing including creating an image of a developed view of a medical image such as an endoscopic image.

2. Description of the Related Art

In recent years, endoscopes have been widely adopted in medical fields. For example, Barrett's esophagus is one disease of the esophagus.

The esophagus is covered by the mucosa of the squamous epithelium, and the stomach and the intestine are covered by the mucosa of the columnar epithelium. Barrett's esophagus is considered that the mucosa of the esophagus (the squamous epithelium) near the junction between the stomach and the esophagus is denatured to a columnar epithelium continuously from the stomach due to the backflow of stomach acids to the esophagus.

In order to diagnose Barrett's esophagus, an endoscopic diagnosis may be applied that uses an endoscope to observe how the columnar epithelium present continuously from the esophagogastric junction extends and a distinctive form of the junction between the columnar epithelium and the squamous epithelium.

As a prior art, Japanese Unexamined Patent Application Publication No. 8-256295 discloses means for correcting an optical distortion occurring in the periphery of a captured endoscopic image.

SUMMARY OF THE INVENTION

A medical image processing apparatus according to the invention, including:

an image conversion section that geometrically converts a medical image resulting from the image pickup of a tubular part in vivo;

a developed-view output section that outputs a converted image obtained by the image conversion section to a display device as an image of a developed view.

A medical image processing method according to the invention, including:

an image converting step of geometrically converting a medical image resulting from the image pickup of a tubular part in vivo;

a developed-view output step of outputting a converted image obtained by the image converting step to a display device as an image of a developed view.

DETAILED DESCRIPTION OF THE PREFERRED EMBODIMENTS

With reference to drawings, embodiments of the present invention will be described below.

Embodiment 1

With reference to FIGS. 1 to 8, Embodiment 1 of the present invention will be described.

Figure 1:
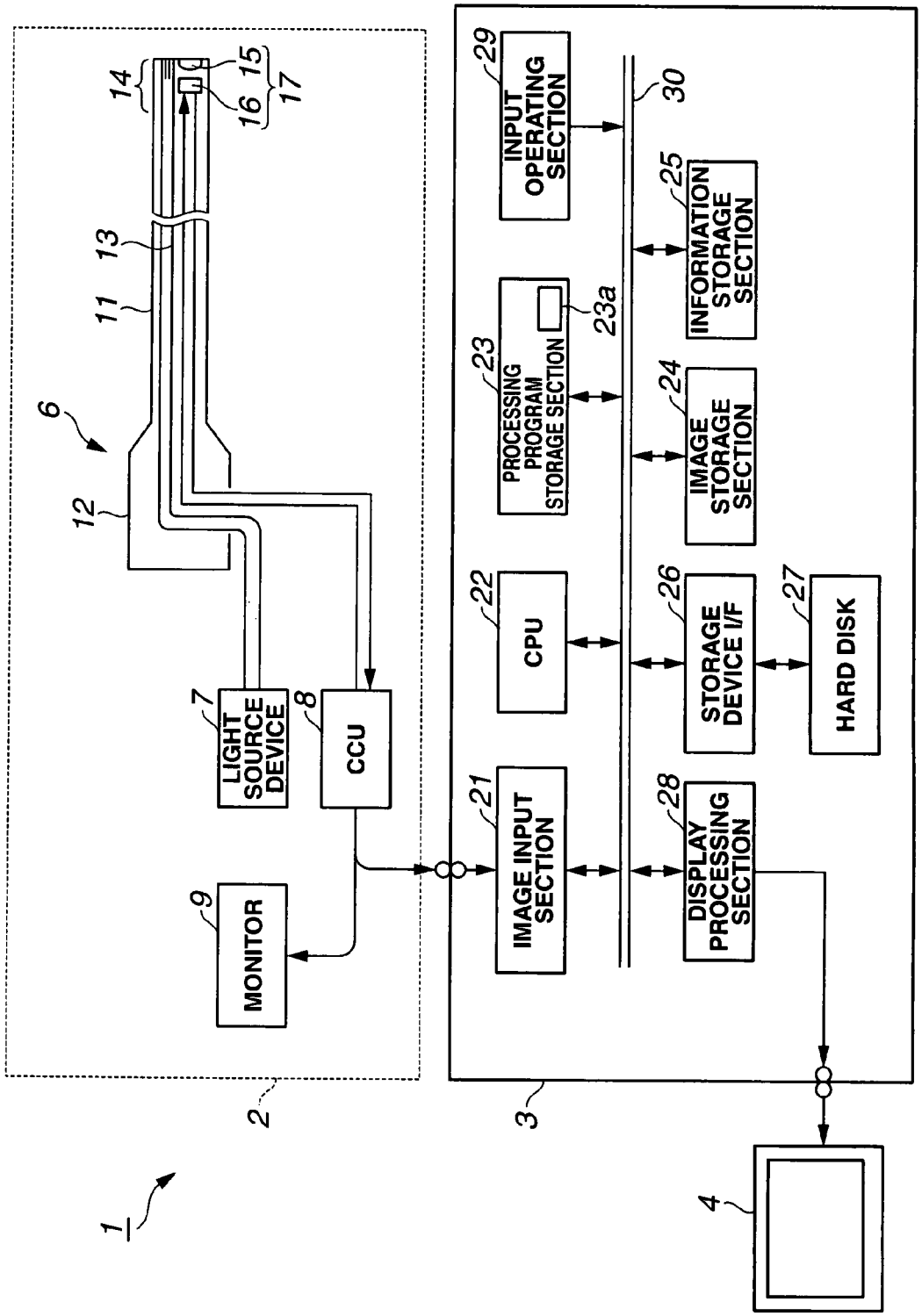
FIG. 1 is a block diagram showing a configuration of an endoscopic system including Embodiment 1 of the present invention.

An endoscopic system 1 shown in FIG. 1 includes an endoscopic observation apparatus 2, an endoscopic image processor (which will be simply abbreviated to image processor) 3 including a personal computer that performs image processing on an endoscopic image obtained by the endoscopic observation apparatus 2 and being Embodiment 1 of the medical image processing apparatus of the present invention, and a display monitor 4 displaying an image image-processed by the image processor 3.

The endoscopic observation apparatus 2 has an endoscope 6 to be inserted to a body cavity, a light source device 7 supplying illumination light to the endoscope 6, a camera control unit (which will be abbreviated to CCU) 8 performing signal processing for image pickup means of the endoscope 6, and a monitor 9 displaying an endoscopic image shot by an image pickup device by receiving the input of video signals outputted from the CCU 8.

The endoscope 6 has a long and narrow insertion section 11 to be inserted to a body cavity and an operating section 12 provided at the rear end of the insertion section 11. A light guide 13 transmitting illumination light is contained through the insertion section 11.

The rear end of the light guide 13 is connected to the light source device 7. Illumination light supplied from the light source device 7 is transferred by the light guide 13 and (the transmitted illumination light) is outputted from the distal end surface mounted on an illumination window provided at a distal end 14 of the insertion section 11 and illuminates a subject such as an affected part.

An image pickup apparatus 17 is provided which includes an objective 15 mounted on an observation window adjacent to the illumination window and a charge-coupled device (which will be abbreviated to CCD) 16, for example, functioning as a solid-state image pickup device placed at the image-forming position of the objective 15. Then, the optical image formed on the image pickup plane of the CCD 16 is photoelectronically converted by the CCD 16.

The CCD 16 is connected to the CCU 8 through a signal line, and, in response to the application of a CCD driving signal from the CCU 8, the CCD 16 outputs the photoelectronically-converted image signals. The image signals are signal-processed by a video processing circuit within the CCU 8 and are converted to video signals. The video signals are outputted to the monitor 9, and an endoscopic image is displayed on the display plane of the monitor 9. The video signals are also inputted to the image processor 3.

The image processor 3 has an image input section 21, a CPU 22 and a processing program storage section 23. The image input section 21 receives the input of video signals corresponding to an endoscopic image inputted from the endoscopic observation apparatus 2. The CPU 22 functions as a central operating processing unit that performs image processing on image data inputted from the image input section 21. The processing program storage section 23 stores a processing program (control program) 23a that causes the CPU 22 to perform image processing.

The image processor 3 has an image storage section 24, an information storage section 25, a hard disk 27, a display processing section 28 and an input operating section 29. The image storage section 24 may store image data inputted from the image input section 21. The information storage section 25 may store information processed by the CPU 22. The hard disk 27 functions as a storage device that may store image data and information processed by the CPU 22 through a storage device interface (I/F) 26. The display processing section 28 performs display processing for displaying image data processed by the CPU 22, for example. The input operating section 29 has a keyboard for inputting data such as a parameter, for image processing and/or performing a command operation by a user.

Then, the video signals generated by the display processing section 28 are displayed on the display monitor 4, and an image-processed image is displayed on the display plane of the display monitor 4. The image input section 21, CPU 22, processing program storage section 23, image storage section 24, information storage section 25, storage device interface 26, display processing section 28 and input operating section 29 are connected to each other through a data bus 30.

Figure 2:
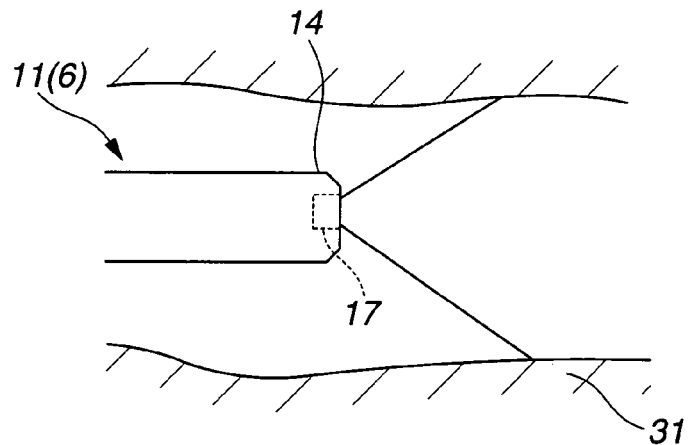
FIG. 2 is a diagram showing a state in which an image is picked up by an endoscope inserted through a tubular organ such as the esophagus.

In the present embodiment, as shown in FIG. 2, the insertion section 11 of the direct-view type endoscope 6 is inserted into a tubular organ such as an esophagus 31 or a tubular part, and an inner wall of the esophagus 31, for example, is picked up by the image pickup apparatus 17 provided in the distal end 14. The direction of the field of vision for image pickup of the image pickup apparatus 17 provided in the direct-view type endoscope 6 is the longitudinal direction of the insertion section 11. Then, the image pickup apparatus 17 is used to pick up an image of the internal surface of a tubular part in a direct-view manner the direction of the field of vision of which is substantially equal to the direction of the luminalis.

Figure 3:
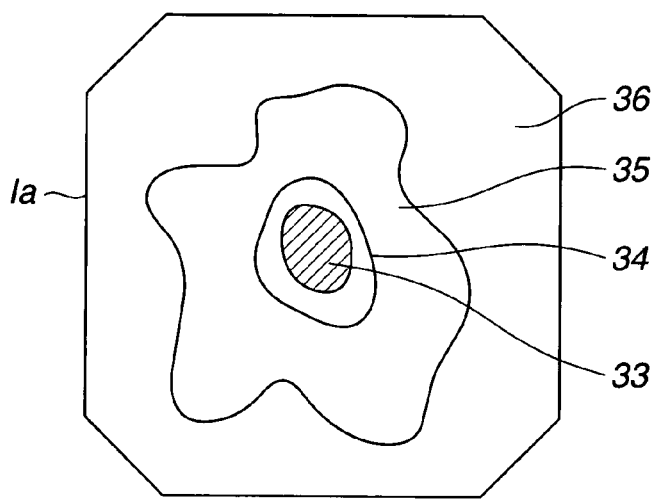
FIG. 3 is a diagram showing an endoscopic image picked up by an image pickup apparatus provided in the endoscope in FIG. 2.

FIG. 3 shows an example of an endoscopic image Ia of Barrett's esophagus image-picked up by the direct-view type endoscope 6. Barrett's esophagus is a state that the mucosa (squamous epithelium) of the esophagus is denatured to the mucosa (columnar epithelium) of the stomach continuously from the esophagogastric junction to the oral cavity. A surgeon diagnoses Barrett's esophagus by observing how the denatured cylindrical epithelial extends and a distinctive form of the junction between the columnar epithelium and the squamous epithelium through the endoscope 6.

The endoscopic image Ia in FIG. 3 is an image of a tubular part from the esophagus 31 to the inside of the stomach. More specifically, (an image part of) a darkest part 33 toward the inside of the stomach, (an image part of) a junction 34 between the surrounding stomach and the esophagus, (an image part of) a columnar epithelium 35 around the junction 34, and (an image part of) a squamous epithelium 36 around the columnar epithelium 35.

In the present embodiment, processing is performed in which an image of a subject of a tubular organ such as the esophagus 31 is picked up by the direct-view type endoscope 6, and the picked up endoscopic image Ia is geometrically converted to create a developed view. The image of the created developed view of the subject is displayed on the display monitor 4.

Figure 4:
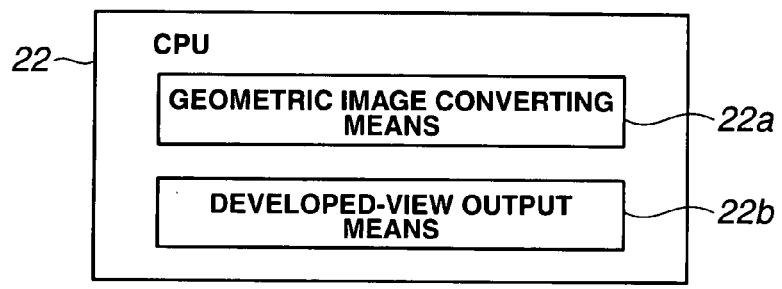
FIG. 4 is a block diagram showing an image processing function by a CPU.

The CPU 22 included in the image processor 3, as shown in FIG. 4, has geometric image converting means (function) 22a that performs geometric conversion and developed-view output means (function) 22b that creates an image of a developed view by geometric conversion and outputs the created image on the display monitor 4. The image of the developed view (or will be simply abbreviated to developed view) is displayed on the display plane of the display monitor 4.

In the present embodiment, the geometric image converting means 22a and developed-view output means 22b, which are shown in FIG. 4, are implemented in software by the CPU 22 by using the processing program 23a. Then, in order to do so, the CPU 22 reads out the processing program 23a memorized (stored) in the processing program storage section 23 shown in FIG. 1, and the CPU 22 performs processing on the flowchart shown in FIG. 5 in accordance with the processing program 23a.

Figure 5:
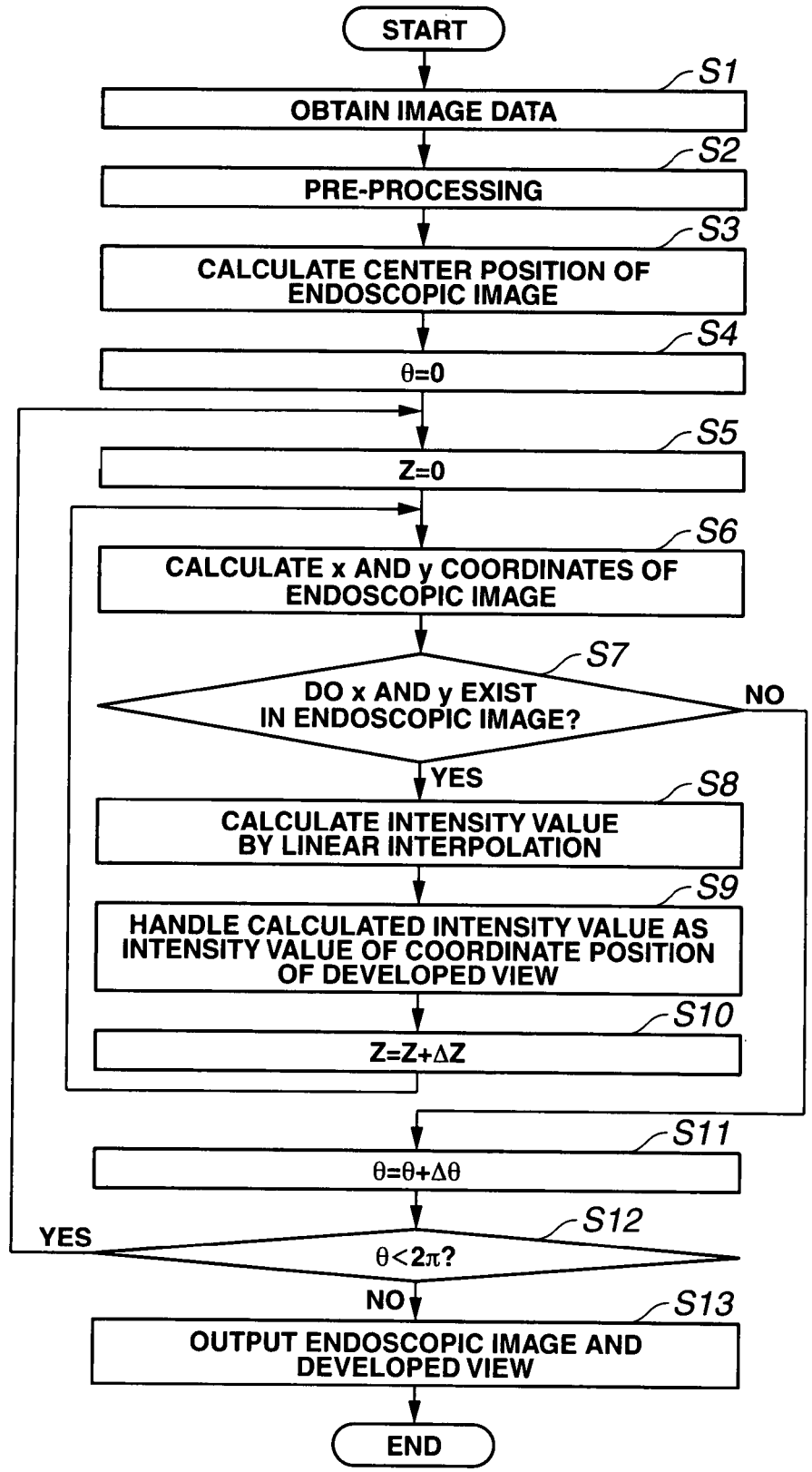
FIG. 5 is a flowchart showing processing steps for creating a developed view.

Next, with reference to FIG. 5, operations of the present embodiment will be described.

When the operation of the image processor 3 starts, the CPU 22 reads out the processing program 23a of the processing program storage section 23 and starts processing in accordance with the processing program 23a. In the first step S1, the CPU 22 obtains image data of the endoscopic image Ia inputted from the CCU 8 of the endoscopic observation apparatus 2 through the image input section 21.

Then, in the next step S2, the CPU 22 performs upstream processing on the obtained image data such as correction for distortion and/or aberration (refer to Japanese Unexamined Patent Application Publication No. 8-256295, for example) and noise removal. In step S3, the CPU 22 detects the position of the darkest part within the endoscopic image Ia and handles the center of gravity of the detected darkest part as the center position of the coordinates of the endoscopic image Ia.

In the present embodiment, a developed view is created about the darkest part within the endoscopic image Ia. In order to detect the darkest part, the endoscopic image Ia is divided into multiple areas, and the average intensities of the divided areas are calculated. Then, the area having the lowest average intensity is calculated as the position of the darkest part.

Figure 6:
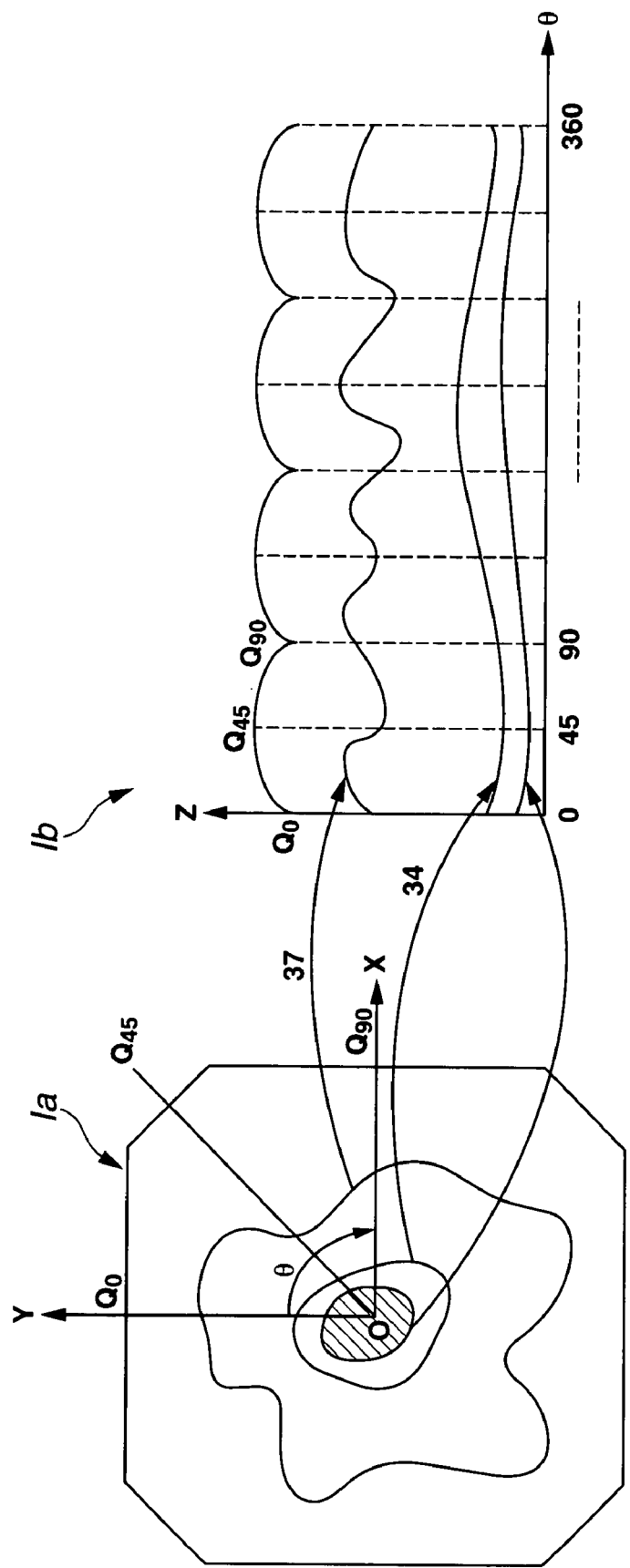
FIG. 6 is a diagram showing a relationship between an endoscopic image and a developed view.

As shown on the left side of FIG. 6, the two-dimensional orthogonal coordinate system of the endoscopic image Ia is handled as X-Y, and the endoscopic image Ia is converted to the polar coordinate system of the coordinate system θ-Z of a developed view Ib as shown in the right side of FIG. 6. The coordinate positions in the coordinate system X-Y are indicated by x and y. The coordinate positions in the polar coordinate system θ-Z are indicated by θ, which indicates the circumferential position, and z, which indicates the distance position from the center.

For easy understanding of the relationship in a case that the developed view Ib is created from the endoscopic image Ia, the forms to display the squamocolumnar junction 37 between the squamous epithelium and the columnar epithelium on the endoscopic image Ia, the esophagogastric junction 34 between the stomach and the esophagus in a developed view are corresponded by arrows in FIG. 6. $Q_0$, $Q_{45}$ and $Q_{90}$ indicate zero, 45 and 90 degrees, which are true in other embodiments to be described later.

In the next steps S4 and S5, the CPU 22 defines the initial value of a coordinate position S (θ,z) of the developed view Ib. In other words, the CPU 22 handles θ=0 in step S4 and z=0 in step S5.

In step S6, the CPU 22 calculates the coordinate position of the endoscopic image Ia, which corresponds to the coordinates S (θ,z) on the defined developed view Ib by:

[EQ 1]

$$x = z \sin \theta$$
$$y = z \cos \theta \quad (1)$$

In step S7, the CPU 22 determines whether the calculated coordinates P (x,y) exists within the endoscope image Ia or not.

Figure 7:
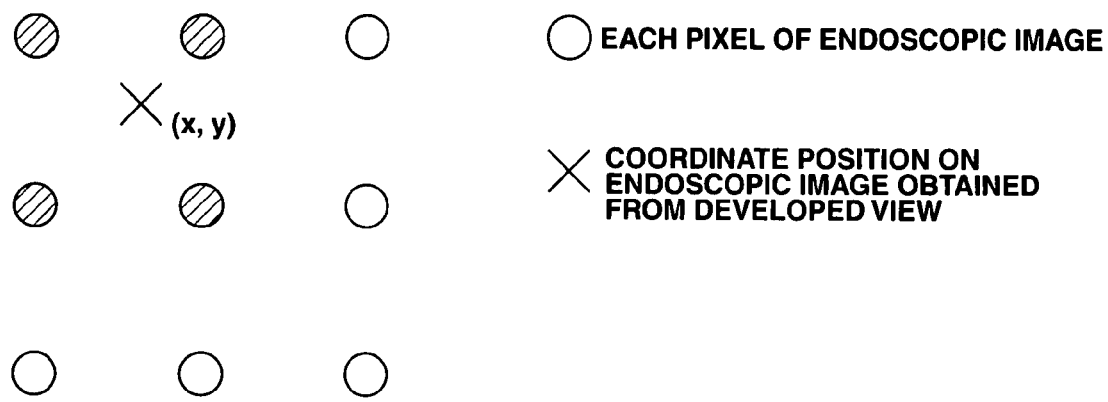
FIG. 7 is an explanatory diagram on a positional relationship between a coordinate position, which is obtained from a developed view, and pixels of an endoscopic image.

Then, if the CPU 22 determines the calculated coordinates P (x,y) exists within the endoscope image Ia, the CPU 22 moves to the processing in step S8. Since, as shown in FIG. 7, the position of the coordinates P (x,y) on the endoscopic image obtained by (Eq. 1) possibly exists between pixels, the CPU 22 in step S8 calculates the intensity value of the coordinates P (x,y) by using a process such as linear interpolation. For example, from the intensity values of four pixels (indicated by shaded circles) around the obtained coordinate position (indicated by x) and the positional relationship, the CPU 22 calculates the intensity value of the coordinate position x.

Notably, the intensity value corresponds to the intensity values of color signals if color image pickup is performed.

The CPU 22 in step S9 handles the intensity value obtained in step S8 as the intensity value of the coordinates S (θ,z) of the developed view. Next, the CPU 22 moves to step S110 where the CPU 22 changes the value z of the developed view (such as the increment of z: Δz=1) and returns to the processing in step S6.

On the other hand, if the coordinates P (x,y) calculated in step S7 do not exist within the endoscopic image Ia, the CPU 22 moves to the processing in step S11 and changes the value θ of the developed view Ib (such as the increment of θ: Δθ=π/180, that is, 1°).

The CPU 22 in the next step S12 returns to step S5 if θ is smaller than 2π (360°) and continues the processing of creating the developed view. On the other hand, if θ is equal to or larger than 2π, the CPU 22 determines that the developed view has been created and moves to step S13 to output the endoscopic image Ia and the developed view Ib to the display monitor 4 and exits the processing.

Figure 8:
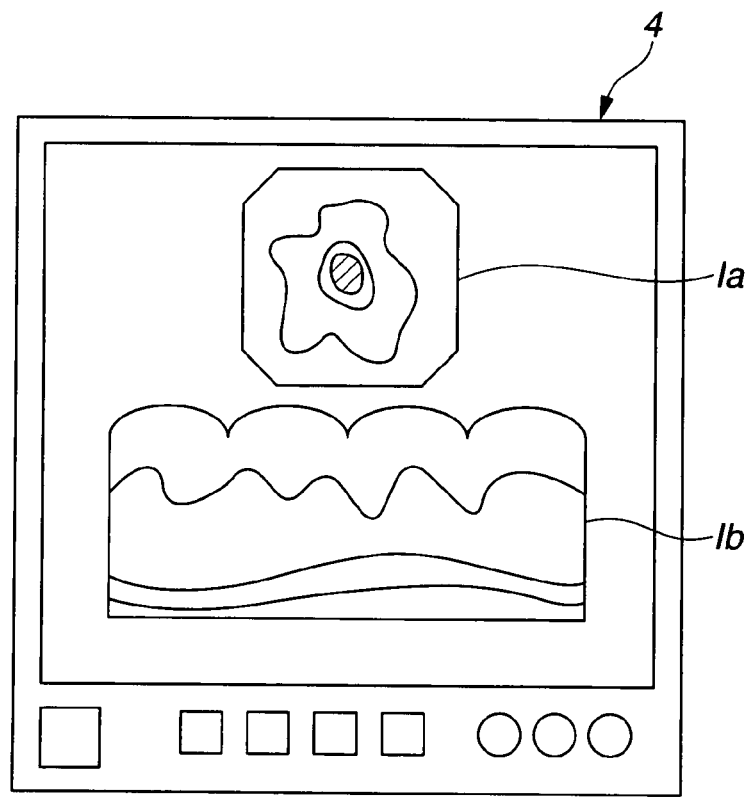
FIG. 8 is a diagram showing a state that a created developed view and an endoscopic image are displayed on a monitor.

Then, as shown in FIG. 8, the endoscopic image Ia and the developed view Ib are displayed on the display monitor 4. Notably, the developed view Ib may only be displayed though both of the endoscopic image Ia and developed view Ib are displayed in FIG. 8.

Since, in this embodiment, the developed view Ib is created, and the developed view Ib is displayed along with the endoscopic image Ia on the display monitor 4 in this way, the values in the circumferential direction (O-direction) and the direction of depth (z-direction), which is the direction of luminalis, can be displayed in a manner allowing easier comparison, for example, than the case with the endoscopic image Ia only. Therefore, the objective diagnoses on a tubular organ such as Barrett's esophagus can be performed more easily.

In the prior art, the endoscopic image Ia in FIG. 8 is only displayed, and the endoscopic image Ia only provides an image projecting the inners of a tubular organ, for example, two-dimensionally. For example, components are displayed in a reduced state in some distances in the direction of depth.

Therefore, a surgeon cannot easily compare parts having different values in the direction of depth since the scales of components depend on the distances in the direction of depth.

On the other hand, according to the present embodiment, the positions of pixels of the endoscopic image Ia, which has been picked up two-dimensionally, are converted to the circumferential positions around a reference line passing through the center position and distance positions (from the center position) orthogonal to the circumferential direction, and the information on intensity values of the pixels is pasted thereto. Then, the image is developed based on the circumferential positions, that is, the value of the angle θ, to display.

In other words, an image of a developed view corresponding to the image created by opening up the inners of a tubular organ at the line in the longitudinal direction (direction of depth) is created and displayed from the endoscopic image Ia.

Thus, according to the present embodiment, even the positions having different distances in the direction of depth can be displayed by an equal scale in the circumferential direction. Therefore, parts in different places can be displayed, which allows easy comparison and easy diagnoses.

Therefore, the present embodiment provides advantages below.

By performing geometric conversion on the endoscopic image Ia of a tubular organ such as the esophagus 31, which is picked up by the direct-view endoscope 6, how the columnar epithelium continuously present from the esophagogastric junction extends and distinctive forms of the columnar epithelium and the squamous epithelium can be easily observed, which therefore allows easily diagnosing Barrett's esophagus, for example.

Embodiment 2

Next, with reference to FIGS. 9 to 13, Embodiment 2 of the present invention will be described.

The present embodiment has the same hardware configuration as that of the image processor 3 in FIG. 1. The present embodiment adopts a processing program having different details from those of the processing program 23*a* stored in the processing program storage section 23 in FIG. 1.

Figure 9:
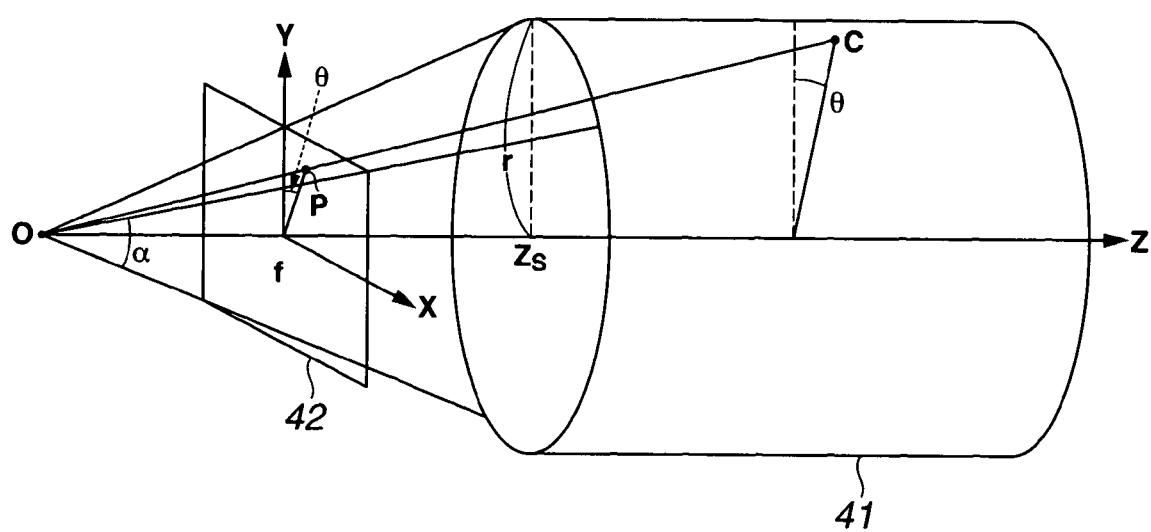
FIG. 9 is an explanatory diagram showing a state that an endoscopic image in Embodiment 2 of the present invention is projected to the surface of a cylinder.

In the present embodiment, as shown in FIG. 9, the geometric conversion is performed to project the endoscopic image picked up by an image pickup plane 42 of the (CCD 16) of the endoscope 6 to the surface of a cylinder 41 by assuming the inners of the esophagus as the cylinder 41 based on the average diameter value of the inners of the esophagus.

In other words, as shown in FIG. 9 the endoscopic image picked up on the image pickup plane 42 (of the CCD 16 included in the image pickup apparatus 17) is projected to the surface of the cylinder 41 through the inside of the cylinder 41. In this case, the size of the cylinder 41 is defined at the value of the tube wall (inner wall) of the near/close esophagus, more specifically, the average value.

In other words, an image of the inners of the esophagus, which is closer to a tube, is formed on the image pickup plane 42 of the CCD 16 by the image pickup apparatus 17 including the objective 15 and the CCD 16, and the formed optical image is picked up by the CCD 16 that performs photoelectronic conversion. Then, the picked endoscopic image mainly near the junction connecting to the esophagus and the stomach is geometrically converted to create an image resulting from the projection of the tube wall of the inside of the esophagus to the inner surface of the approximate cylinder 41 by the objective 16.

Then, by developing the cylinder 41 having the projection of the endoscopic image by the geometric conversion, (the image of) the developed view of the endoscopic image having the projection of the cylinder 41 is created. Then, the developed view is outputted to a display device such as the display monitor 4, and the developed view is displayed on the display plane of the display device.

Figure 10:
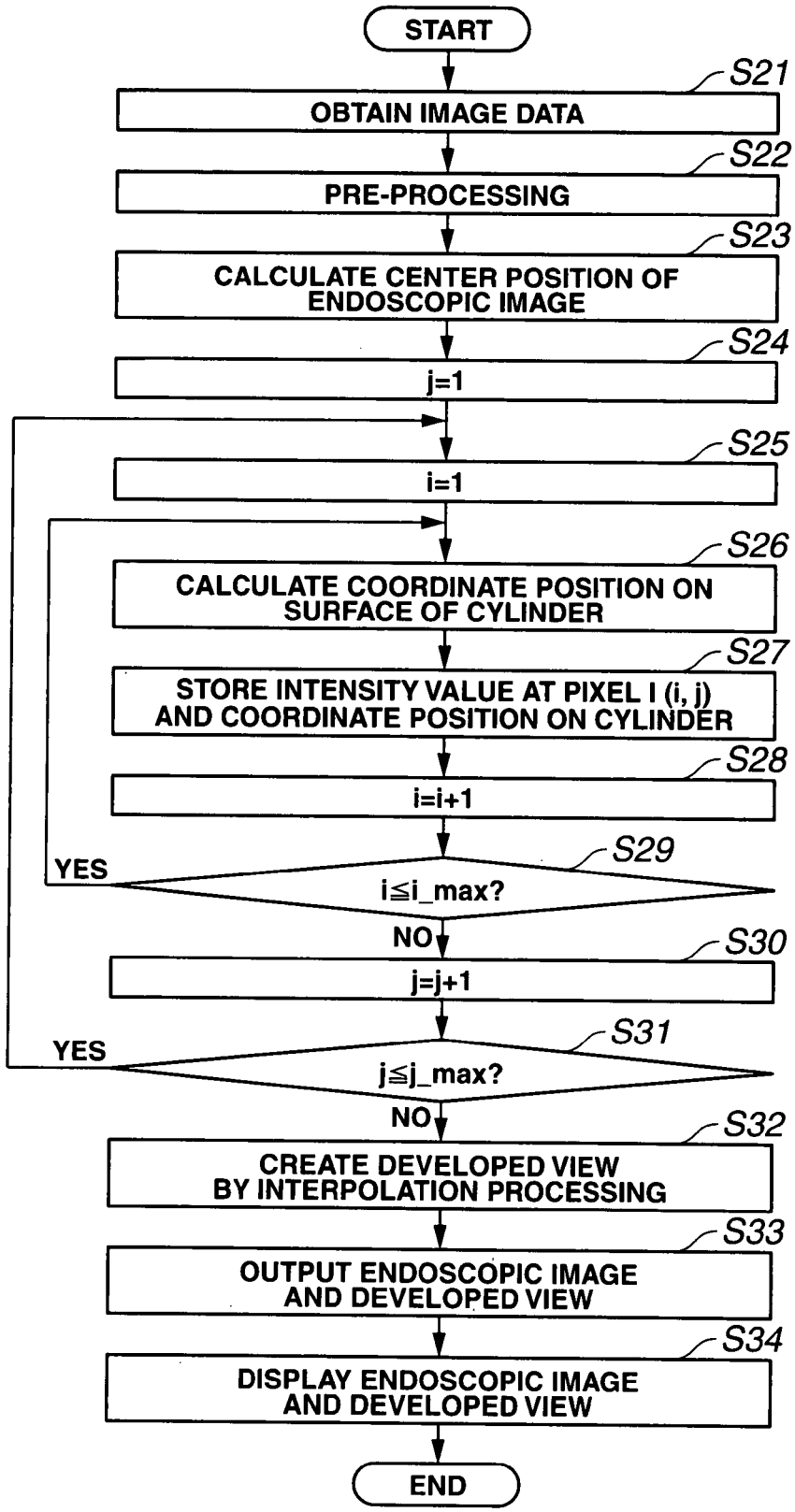
FIG. 10 is a flowchart showing processing steps for creating a developed view in Embodiment 2.

The flowchart in FIG. 10 shows the processing steps of creating a developed view.

Like Embodiment 1, when the operation by the image processor 3 starts, the CPU 22 reads out a processing program in the processing program storage section 23 and starts the processing in accordance with the processing program. The CPU 22 in the first step S21 obtains image data of an endoscopic image Ia inputted from the CCU 8 of the endoscopic observation apparatus 2 through the image input section 21.

Then, the CPU 22 in the next step S22 performs upstream processing on the obtained image data such as correction for distortion/aberration and noise removal, and, in step S23, detects the position of the darkest part within the endoscopic image and handles the detected position as the center position of the coordinates of the endoscopic image.

The CPU 22 handles the coordinate system on the endoscopic image (the image pickup plane 42 of the CCD 16) as X-Y and the coordinate system of the surface of the cylinder as θ-Z as shown in FIG. 9.

Figure 11:
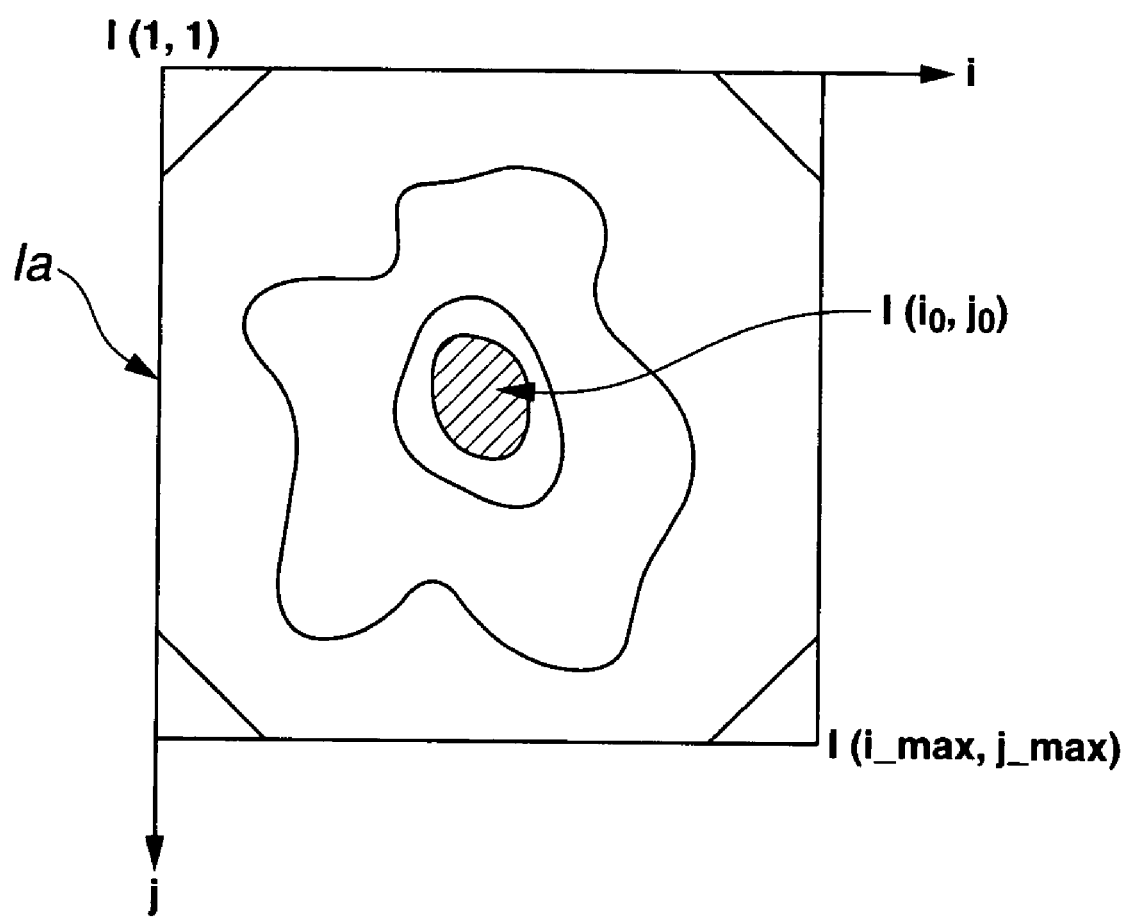
FIG. 11 is an explanatory diagram showing pixel positions on an endoscope image.

As shown in FIG. 11, assuming that each pixel of an endoscopic image Ia is I(i,j) ($1 \leq i \leq i\_max$ and $1 \leq j \leq j\_max$) and the position of the darkest part is I(jo,jo), the relationship between the coordinates P(x,y) in the coordinate system X-Y of the endoscopic image in FIG. 9 and the pixel position I (i,j) of the endoscopic image Ia is expressed by:

[EQ 2]

$$x = (i - i_o) x_{CCD}$$

$$y = (j_o - j) y_{CCD} \qquad (2)$$

where $x_{CCD}$ and $y_{CCD}$ are distances between pixels in the directions of the X-axis and Y-axis.

Next, in steps S24 and S25, the CPU 22 defines the initial position I(1,1) of the pixel of the endoscopic image Ia. In other words, the CPU 22 defines the pixel position parameter as i=1 and j=1. Then, in the next step S26, the CPU 22 obtains the coordinates C (θ,z) on the surface of the cylinder 41, which corresponds to the coordinates P (x,y) on the endoscopic image Ia by:

[EQ 3]

$$\theta = \sin^{-1}\left(x / \sqrt{x^2 + y^2}\right) \qquad (3)$$
$$z = rf / \sqrt{x^2 + y^2}$$
$$z_s = r / \tan(\alpha/2)$$

where f is the focus distance of an image pickup system (more specifically, the objective 15), r is the radius (which may be calculated from the average diameter of the esophagus, for example) of the cylinder 41 and α is the angle of view.

The CPU 22 in step S27 performs in the image storage section 24, for example, processing of storing the coordinate position C(θ,z) on the surface of the cylinder 41, which corresponds to the pixel I (i,j) (where i=1 and j=1) on the endoscopic image Ia.

The CPU 22 in the next step S28 increments the parameter i by one (that is, moves the pixel to the adjacent pixel horizontally) and, in step S29, determines whether the parameter i is equal to or lower than i_max or not. Then, the CPU 22 returns to step S26 if the parameter i is equal to or lower than i_max and continues the processing.

On the other hand, if the parameter i is higher than i_max, the CPU 22 moves to the processing in the next step S30, the CPU 22 in step S30 increments the parameter j by one (that is, moves the pixel to the next pixel vertically).

The CPU 22 in step S31 determines whether the parameter j is equal to or lower than j_max or not. Then, the CPU 22 returns to step S26 if the parameter j is equal to or lower than j_max and continues the processing. On the other hand, if the parameter j is higher than j_max, the CPU 22 moves to the processing in the next step S32.

The CPU 22 in step S32 obtains the coordinate position C(θ,z) on the surface of the cylinder 41, which corresponds to all pixels I (i,j) of the endoscopic image Ia and creates a developed view (by interpolation processing as described below).

Figure 12:
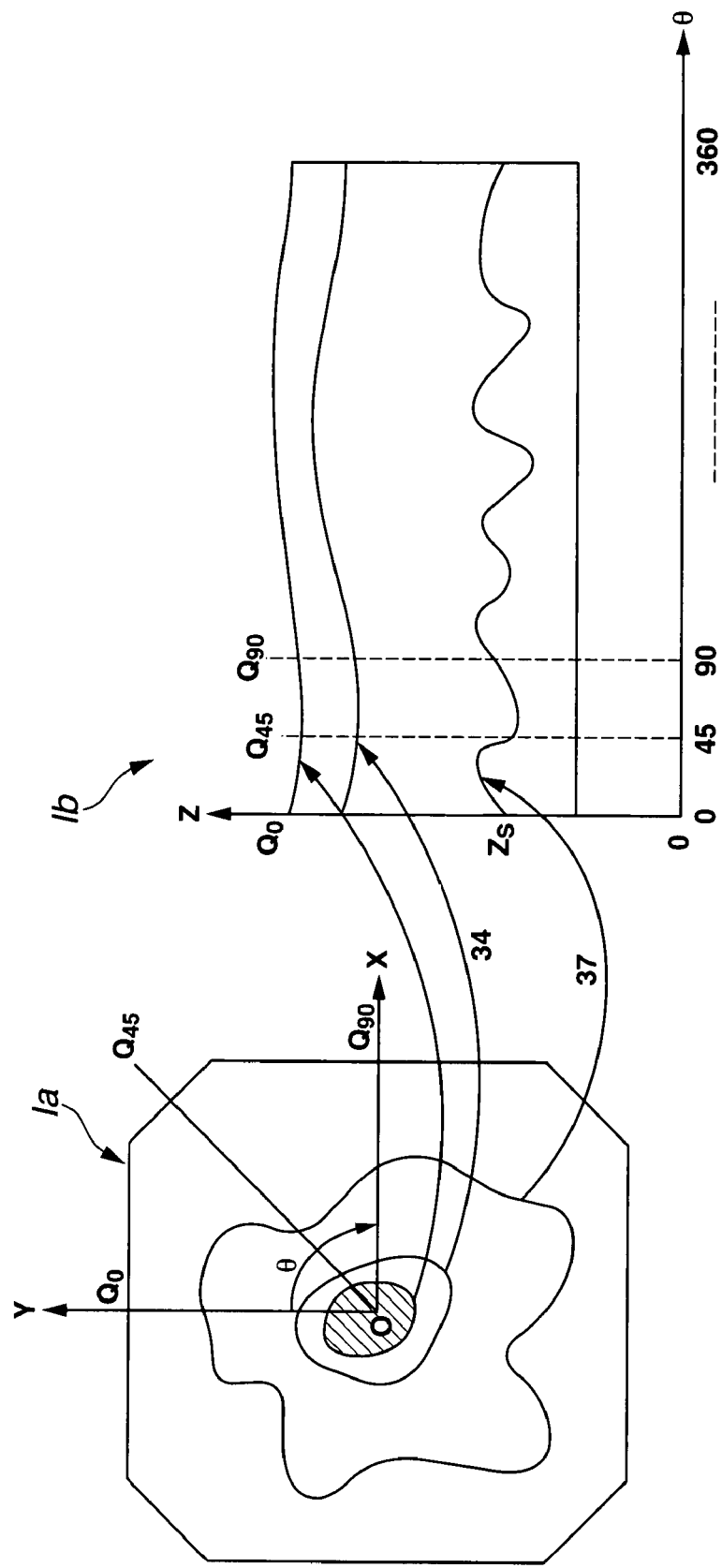
FIG. 12 is an explanatory diagram for creating a developed view by projecting positions of pixels on an endoscopic image to the surface of a cylinder and pasting the intensity values of the pixels thereto.

The CPU 22 pastes the intensity values of the pixels of the endoscopic image Ia on the left side of FIG. 12 to the coordinate system θ-z on the surface of the cylinder shown on the right side in FIG. 12.

Figure 13:
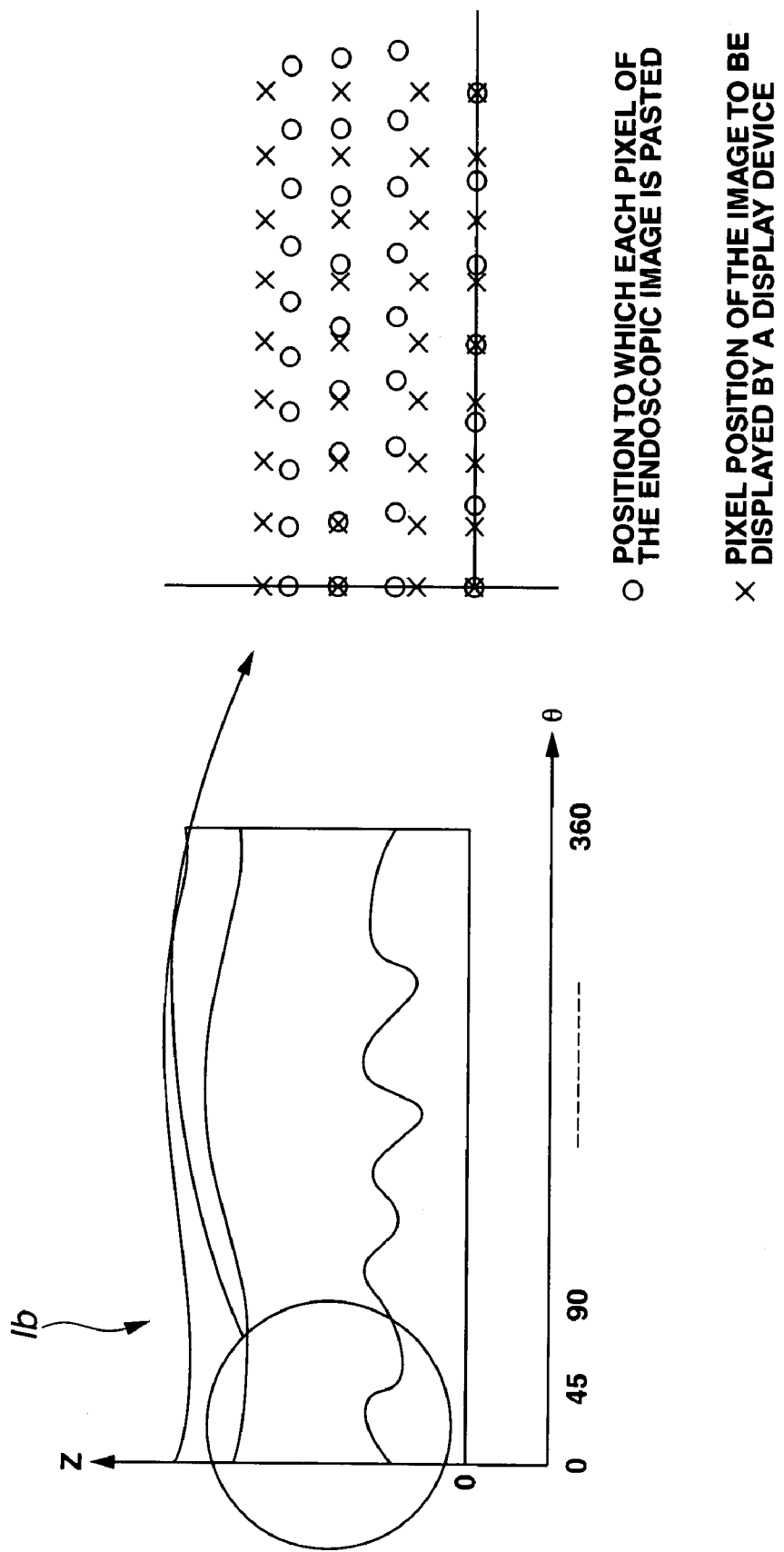
FIG. 13 is an explanatory diagram for performing interpolation processing if the positions to which the pixels of an endoscopic image are pasted do not agree with the positions of the image displayed as a developed view on a display device.

The pixels pasted to the surface of the cylinder displayed by the developed view Ib shown in FIG. 13 exist unevenly, and the degree of roughness increases as the value Z increases. FIG. 13 shows an enlarged view, on the right side, of a part of the developed view Ib on the left side.

Since, as shown in FIG. 13, the pasted pixels do not agree with the pixel positions on the image displayed on a display device such as the display monitor 4, the image to be displayed on the display device, that is, the developed view Ib is created by interpolation processing.

In other words, the CPU 22 in step S32 performs the interpolation processing and creates an image displayable on the display device such as the display monitor 4, that is, the developed view Ib. Then, the CPU 22 in step S33 outputs the developed view Ib to the display monitor 4 along with the endoscopic image Ia. Then, in step S34, the display monitor 4 displays the developed view Ib and the endoscopic image Ia as shown in FIG. 8, and the processing ends. In this case, the developed view Ib is displayed as a developed view having a different gradient in the z-direction from that of Embodiment 1.

The present embodiment provides advantages below.

A developed view Ib with higher accuracy than that of Embodiment 1 can be created since the developed view Ib is created by assuming that the inners of a tubular organ such as the esophagus 31 as the cylinder 41 and projecting the endoscopic image Ia picked up on the image pickup plane of the endoscope 6 to the cylinder 41.

In other words, in Embodiment 1, the positions on an endoscopic image Ia are converted to the polar coordinate system by the distance z from the center on the endoscopic image Ia and the angle θ as positional information in the circumferential direction from a reference position passing through the center, are developed by the angle θ and are displayed as a developed view Ib along with the distance z. On the other hand, in the present embodiment, the developed view Ib is created by assuming a tubular part (tubular organ) of the esophagus 31 as the cylinder 41 and projecting positions on the endoscopic image Ia to the surface of the cylinder 41. Therefore, the developed view Ib reflecting a more realistic state can be created.

Therefore, according to the present embodiment, the developed view Ib can be obtained which allows easier comparison between parts having different values in the direction of depth (the axial direction of the luminalis).

Having described in Embodiments 1 and 2 that the position of the darkest part within an endoscopic image is detected and is handled as the center position of the endoscopic image Ia, the center position may be estimated from the direction that the intensity varies (as disclosed in Japanese Unexamined Patent Application Publication No. 2003-93328).

Embodiment 3

With reference to FIGS. 14 to 17, Embodiment 3 of the present invention will be described next.

The configuration of this image processor is the same as that of Embodiment 1 except that the processing program to be stored in the processing program storage section 23 is different from the processing program 23a in FIG. 1. The processing program is used to perform the processing below.

In the present embodiment, a tubular organ such as the esophagus is assumed as a cylinder 41, and the positional relationship between (image pickup means of) the distal end of an endoscope and the tubular organ is estimated by using a model image and an endoscopic image.

Then, an endoscopic image shot by the endoscope 6 is projected to the surface of the cylinder 41 based on the estimated positional relationship, and the projected image is displayed on a display device such as the display monitor 4 as a developed view created by developing the projected image.

In order to estimate the positional relationship, the present embodiment includes creating multiple model images, which have different positional relationships between (the image pickup plane of) the image pickup apparatus 17 at the distal end of the endoscope 6 and the cylinder 41, performing matching processing between the created multiple model images and the actually shot endoscopic image Ia and detecting the model image close to the shot endoscopic image Ia.

Then, the positional relationship between the image pickup apparatus 17 and the cylinder 41 is estimated from the detected model image. The method for creating the model image will be described with reference to FIG. 14.

Figure 14:
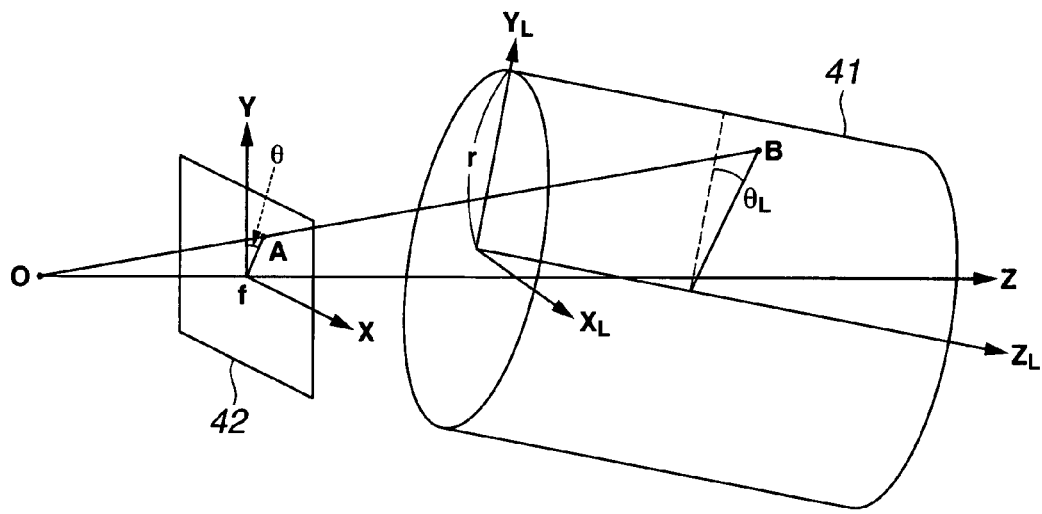
FIG. 14 is an explanatory diagram showing a state that an endoscopic image in Embodiment 3 of the present invention is projected to the surface of a cylinder.

FIG. 14 is a diagram showing the positional relationship between the image pickup plane 42 of the image pickup apparatus 17 and the cylinder 41, assuming that the inners of a tubular organ such as the esophagus as the cylinder 41. While, in Embodiment 2, the condition is defined that the optical axis of the image pickup plane 42 passes through the center of the cylinder 41, the condition is eliminated in the present embodiment in addition to that the case that both of them are inclined/declined will be considered.

The coordinates $(x_L, y_L, z_L)$ on the surface of the cylinder 41 is expressed by:

[EQ 4]

$$\begin{pmatrix} x_L \\ y_L \\ z_L \end{pmatrix} = \begin{pmatrix} r\sin\theta_L \\ r\cos\theta_L \\ z_L \end{pmatrix} \quad (4)$$

where the coordinate system with reference to the cylinder 41 is $x_L\text{-}y_L\text{-}z_L$.

The relationship between the coordinate system X-Y-Z with reference to the image pickup plane 42 and the coordinate system $X_L\text{-}Y_L\text{-}Z_L$ of the cylinder 41 is expressed by:

[EQ 5]

$$\begin{pmatrix} x \\ y \\ z \end{pmatrix} = R \begin{pmatrix} x_L \\ y_L \\ z_L \end{pmatrix} + M \quad (5)$$

where R is a rotation matrix, and M is a translational matrix. In other words, the matrixes R and M function as parameters exhibiting the positional relationship of the cylinder 41 with respect to the image pickup plane 42 of the image pickup apparatus 17.

The relationship between the coordinate system $X_I\text{-}Y_I$ with reference to the endoscopic image shot by the image pickup plane 42 and the coordinate system X-Y-Z of the image pickup plane 42 is expressed by:

[EQ 6]

$$\begin{pmatrix} x_I \\ y_I \end{pmatrix} = \begin{pmatrix} xf/z \\ yf/z \end{pmatrix} \quad (6)$$

Figure 15:
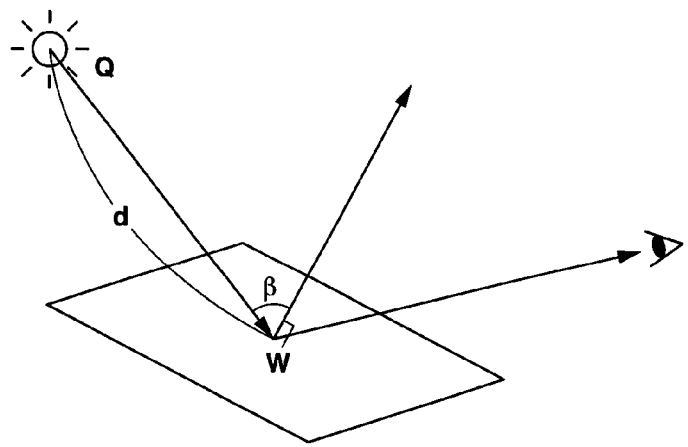
FIG. 15 is an explanatory diagram showing a state that light from a light source is reflected by the surface of an object.

The reflected light I of the surface of the cylinder is expressed by:

[EQ 7]

$$I(x_I, y_I) = kI_q \cos\beta/d^2 \quad (7)$$

assuming that, as shown in FIG. 15, a light source Q is at a limited distance d from an object and the light source Q is a point source and that the surface of the cylinder functioning as a specific example of the object diffuse reflects the light of the light source Q.

In this case, k is a diffuse reflectance of the surface, Iq is the luminous intensity of the light source Q, β is the angle formed by the normal line of the surface at a point W and the direction QW of the light source, and d is the distance between the point W and the light source Q.

Therefore, by defining the position/direction of the cylinder 41 with respect to the image pickup apparatus 17, the position A on the endoscopic image shot by the image pickup apparatus 17 can be obtained from the position B on the surface of the cylinder based on (Eq. 4) to (Eq. 6), and the intensity value then can be calculated based on (Eq. 7).

Figure 16A:
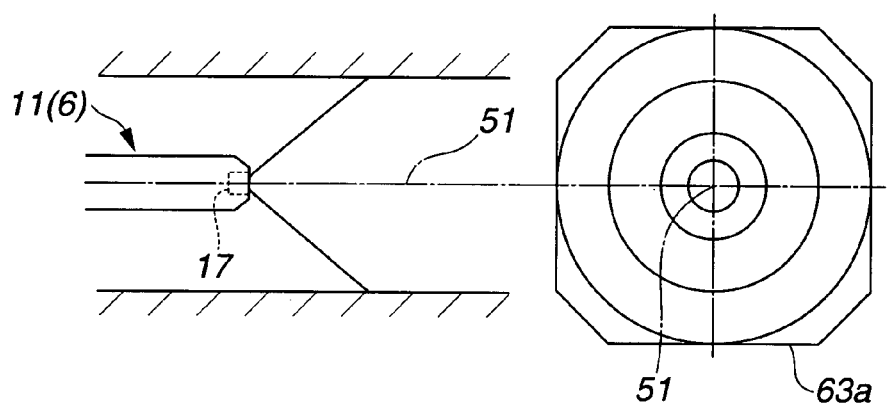
FIG. 16A is a diagram showing a positional relationship in which an image pickup apparatus of an endoscope exists on the center axis of a cylinder and a model image corresponding thereto.
Figure 16B:
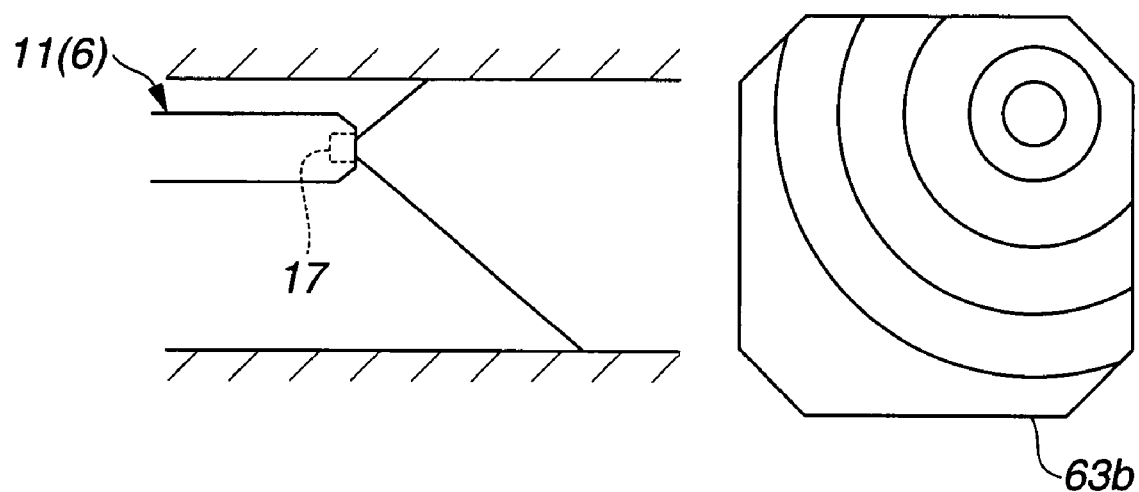
FIG. 16B is a diagram showing a positional relationship resulting from the parallel movement of the image pickup apparatus upward from the state in FIG. 16A and a model image corresponding thereto.
Figure 16C:
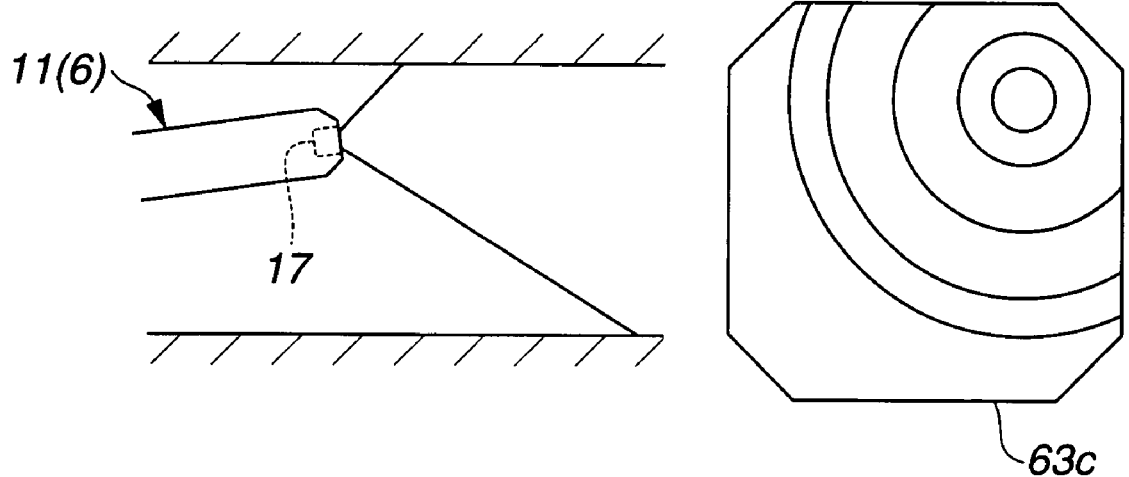
FIG. 16C is a diagram showing a positional relationship resulting from the tilting of the axis direction of the insertion section from the state in FIG. 16A and a model image corresponding thereto.

FIG. 16A shows a model image 63a obtained when the image pickup apparatus 17 exists on the center line 51 of the cylinder 41 and faces in the direction of the center line 51. FIG. 16B is a model image 63b resulting from the upward parallel movement of the image pickup apparatus 17 from the state in FIG. 16A. FIG. 16C is a model image 63c resulting from the parallel movement of the image pickup apparatus 17 from the state in FIG. 16A and the change orientation of the field of vision or the axis of the insertion section 11.

Therefore, in the present embodiment, multiple positions-directions of the image pickup apparatus 17 and the cylinder are defined, and multiple model images are created.

Figure 17:
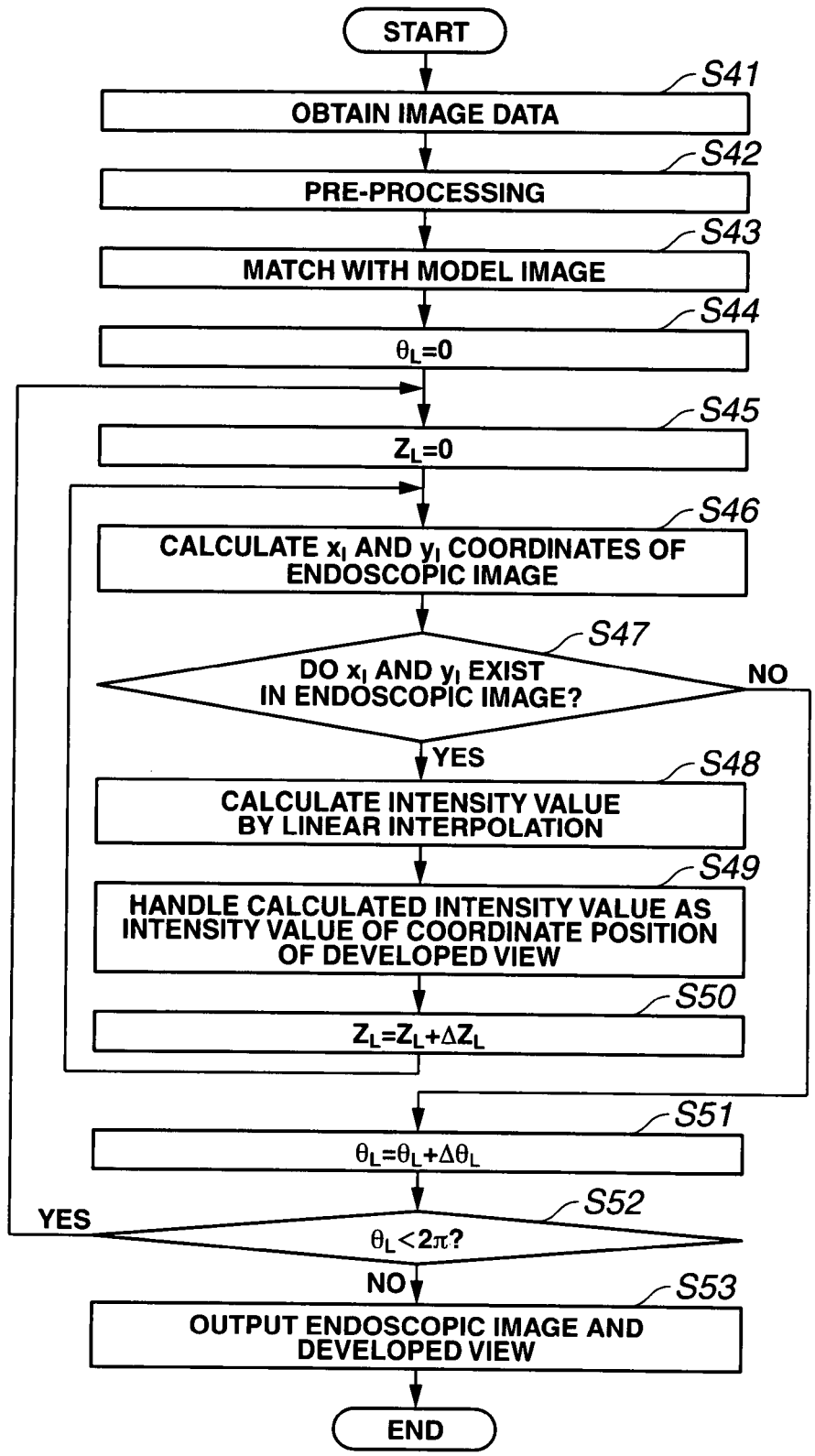
FIG. 17 is a flowchart showing processing steps for creating a developed view in Embodiment 3.

Then, the CPU 22 processes by following the flowchart shown in FIG. 17 and creates the developed view Ib as described below.

Like Embodiment 1, upon start of the operation by the image processor 3, the CPU 22 reads out a processing program in the processing program storage section 23 and starts the processing in accordance with the processing program. The CPU 22 in the first step S41 obtains image data of an endoscopic image inputted from the CCU 8 of the endoscopic observation apparatus 2 through the input section 21.

Then, the CPU 22 in the next step S42 performs upstream processing on the obtained image data such as correction for distortion/aberration and noise removal, and, in step S43, performs matching processing with a model image. By the matching processing, the CPU 22 calculates the correlation value between the endoscopic image and the model image, which are obtained by normalized cross correlation, for example, and detects a model image with the highest correlation.

The CPU 22 detects a model image with the highest correlation with the image data obtained by the matching processing in step S43 and obtains the relationship in position/direction between the image pickup apparatus 17 and the cylinder 41 from the detected model image. As shown in FIG. 6 on Embodiment 1, the coordinate system of the endoscopic image Ia is X-Y, and the coordinate system of the developed view is $\theta_L$-$Z_L$.

Next, the CPU 22 in steps S44 and S45 defines the initial values of the coordinates S ($\theta_L$,$z_L$) on the surface of the cylinder. The CPU 22 in step S46 obtains the coordinates P ($x_I$,$y_I$) on the endoscopic image, which correspond to the defined coordinates S ($\theta_L$,$z_L$) from (Eq. 4) to (Eq. 6).

In step S47, the CPU 22 determines whether the calculated coordinates P ($x_I$,$y_I$) exists within the endoscopic image or not. If so, the CPU 22 moves to step S48.

Since the position of the coordinates P($x_I$,$y_I$) on the endoscopic image may possibly exist in the middle between pixels as shown in FIG. 7 on Embodiment 1, the CPU 22 in step S48 calculates the intensity value of the coordinates P($x_I$,$y_I$) by using processing such as linear interpolation.

For example, the intensity value of the coordinate position x is obtained from the intensity values and positional relationship of the surrounding four pixels (indicated by shaded circles) of the obtained coordinate position x.

In step S49, the CPU 22 handles the intensity value obtained by step S48 as the intensity value of the coordinates S ($\theta_L$,$z_L$) on a developed view thereof.

Next, the CPU 22 moves to step S50 to change the value $Z_L$ of the developed view (such as $\Delta z_L$=1) and then moves to step S46.

If the CPU 22 in step S47 determines that the calculated coordinates P($x_I$,$y_I$) do not exist within the endoscopic image, the CPU 22 moves to step S51 to change the value $\theta_L$ of the developed view (such as $\Delta\theta_L$=$\pi$/180:1°).

If the CPU 22 determines that $\theta_L$ is smaller than 2$\pi$(360°) in step S52, the CPU 22 moves to step S45 to continue the processing of creating the developed view. When $\theta_L$ is equal to or larger than 2$\pi$, the CPU 22 determines that the developed view has been created and moves to step S53 to display the endoscopic image and developed view on the display monitor 4 as in Embodiment 1 and exits the processing (or the developed view may only be displayed).

The present embodiment provides advantages below.

The present embodiment can create a developed view with higher accuracy than that of Embodiment 2 since a developed view of an endoscopic image is created by assuming a tubular organ such as the esophagus as a cylinder 41, estimating the relationship in position/direction between the cylinder 41 and the image pickup apparatus 17 from an image and creating the developed view of the endoscopic image based on the estimated position/direction.

Figure 18:
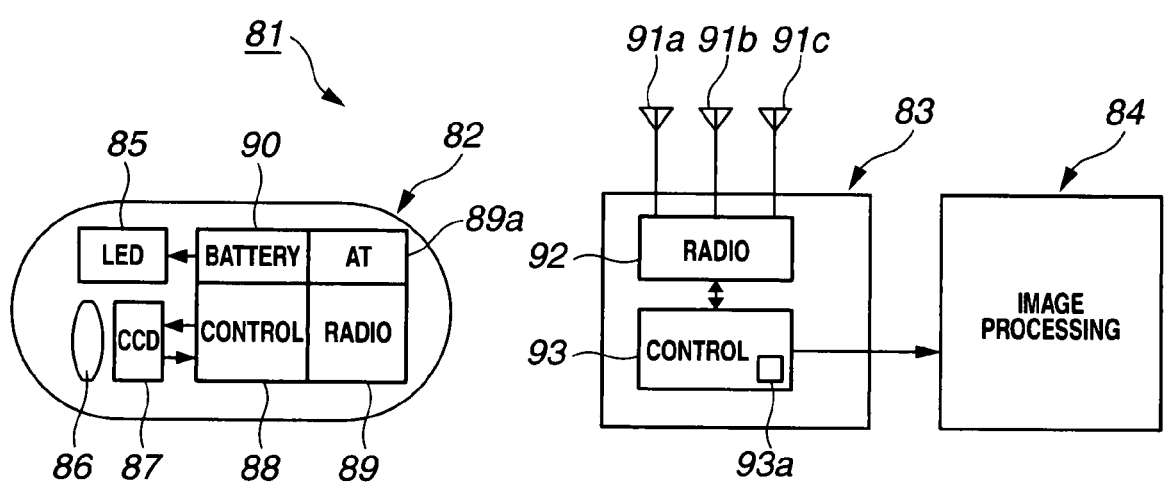
FIG. 18 is a configuration diagram of a capsule-type endoscopic system including a variation example.

Having described the endoscope 6 having the long and narrow insertion section 11 in Embodiments 1 to 3, the present invention is also applicable to a capsule-type endoscope 82 as shown in FIG. 18.

A capsule-type endoscope 81 including a variation example as shown in FIG. 18 includes the capsule-type endoscopic apparatus (which will be abbreviated to capsule type endoscope, hereinafter) 82 that picks up an image of the inside of a body cavity by being swallowed by a patient, an external apparatus 83 that is placed outside of the body of the patient and receives and records image data from the capsule-type endoscope 82 and an image processor 84 to which an image is inputted from the external apparatus 83.

The capsule-type endoscope 82 includes an LED 85, for example, functioning as illumination means within a capsule-shaped container, an objective 86 that forms an image of a illuminated subject, a CCD 87 that is placed at the image-formed position and having image pickup means for picking up an image, a control circuit 88 that performs signal processing, for example, on image pickup signals picked up by the CCD 87, a radio circuit 89 that performs processing of transmitting the picked up image by radio and a battery 90 that supplies power to circuits.

The external apparatus 83 receives, by a radio circuit 92, radio waves from an antenna 89a of the radio circuit 89 in the capsule-type endoscope 82 through multiple antennas 91a, 91b and 91c and transmits the signals to a control circuit 93. The control circuit 93 converts the signals to video signals and outputs the video signals to the image processor 84.

Then, the image processor 84 performs processing as in the embodiments above.

Notably, the control circuit 93 has a position detecting function 93a that estimates the position of the capsule-type endoscope 82 through the multiple antennas 91a to 91c. The position detecting function 93a may be used to select and define an image to be detected. In other words, the position detecting function 93a may be used to detect whether an image of a part close to the border from the esophagus to the stomach is being picked up or not and, if an image of a part closer to the boundary to some extent is being picked up, the image may be used as an endoscopic image to create a developed view thereof as in the cases above.

Thus, the biological mucosa of a part close to the boundary from the esophagus to the stomach to be detected can be determined efficiently.

Embodiment 4

With reference to FIGS. 19 to 30, Embodiment 4 of the invention will be described next. It is an object of Embodiments 4 and 5 to provide a medical image processing apparatus and medical image processing method that can create an image of a developed view with high accuracy by estimating a three-dimensional form of the inners of a tubular part, in addition to the object of Embodiment 1, for example.

Figure 19:
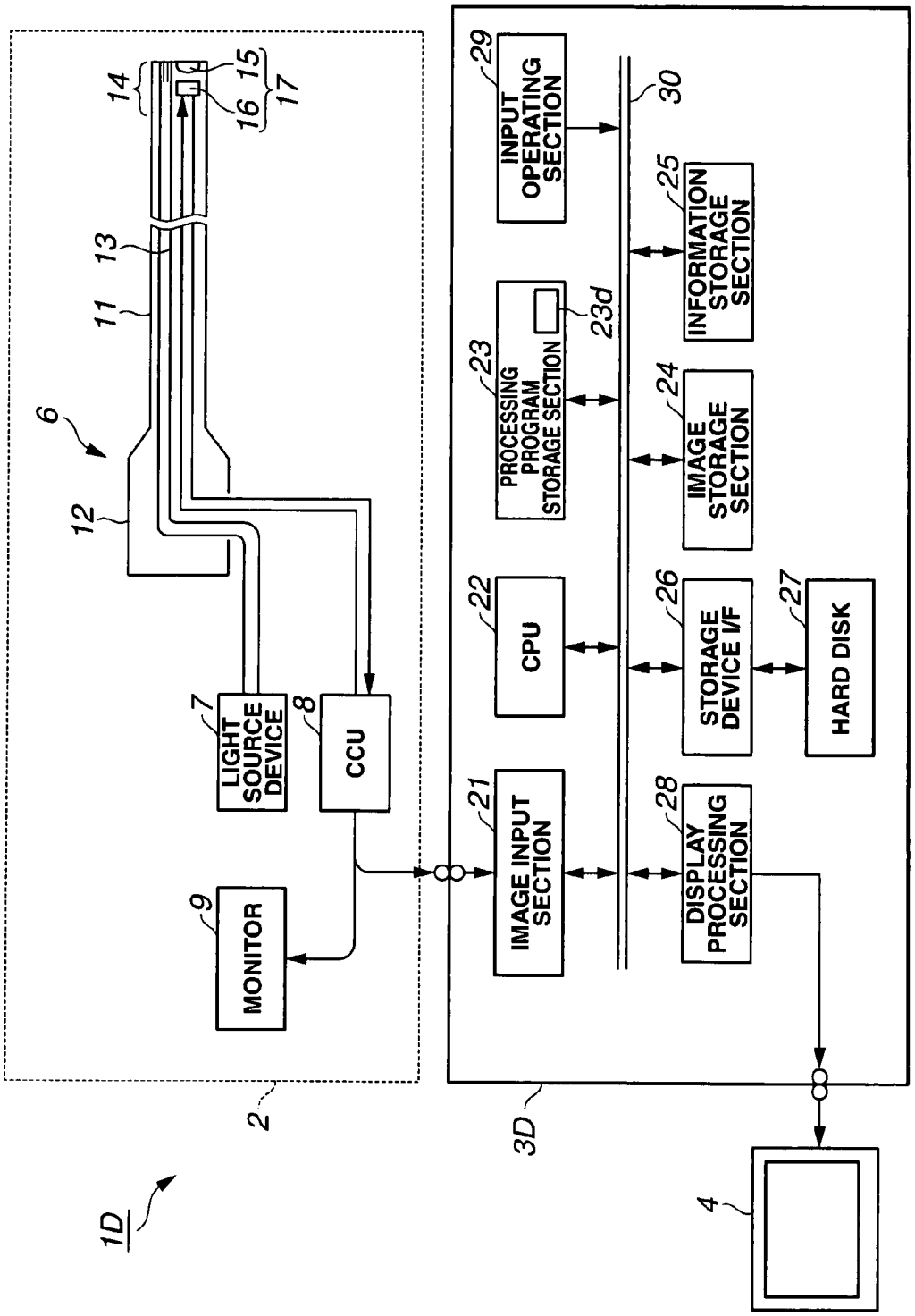
FIG. 19 is a block diagram showing a configuration of an endoscopic system including Embodiment 4 of the present invention.

FIG. 19 shows a configuration of an endoscopic system 1D including an image processor 3D of Embodiment 4 of the present invention. The endoscopic system 1D has the same hardware configuration as that of the endoscopic system 1 in FIG. 1. A processing program 23d stored in the processing program storage section 23 of the image processor 3D is only different from the processing program 23a in FIG. 1. For this reason, the same reference numerals are given to the same components to those of Embodiment 1, the description of which will be omitted herein.

Also in the present embodiment, the insertion section 11 of the direct-view type endoscope 6 is inserted to a tubular part (or tubular organ) such as the esophagus 31, an image of which is then picked up by the image pickup apparatus 17, as shown in FIG. 2. FIG. 3 also shows an example of the endoscopic image Ia of Barrett's esophagus, which is picked up by the direct-view endoscope 6.

In the present embodiment, an image of a tubular organ such as the esophagus 31 is picked up by the direct-type endoscope 6, and a three-dimensional form of the subject is estimated from the picked-up image.

An image allowing easy creation of a developed view is created by estimating the straight line passing through the center of the estimated three-dimensional form and performing geometric conversion with reference to the straight line, and the image is outputted to display means as the developed view. Then, the developed view is displayed on the display plane of the display means.

Figure 20:
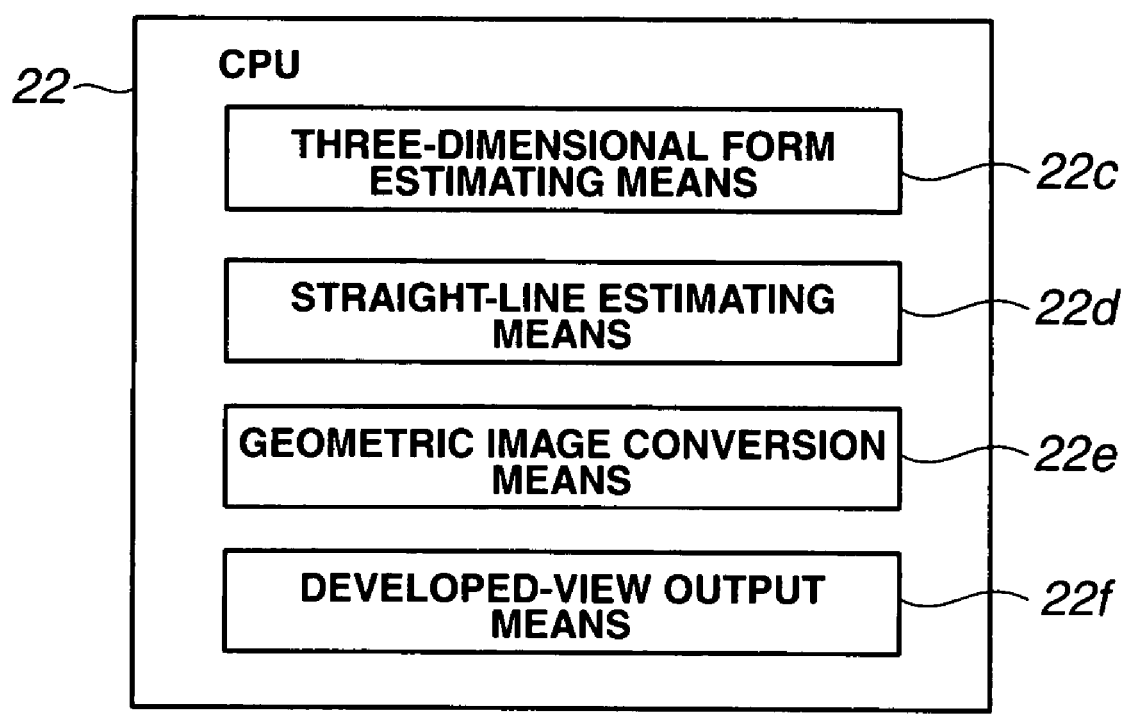
FIG. 20 is a block diagram showing an image processing function by a CPU.

In other words, the CPU 22 included in the image processor 3D has, as functions thereof as shown in FIG. 20, three-dimensional form estimating means (function) 22c, estimating means (function) 22d for a straight line passing through the center of the estimated three-dimensional form, geometric conversion means (function) 22e for performing geometric conversion to a form allowing easy display as a developed view with reference to the estimated straight line, and developed-view output means (function) 22f for outputting the image of a developed view by the geometric conversion to the display monitor 4, and a developed view is displayed on the display plane of the display monitor 4.

In the present embodiment, the three-dimensional form estimating means 22c, straight-line estimating means 22d, geometric conversion means 22e and developed-view output means 22f shown in FIG. 20 are implemented in software. In other words, the processing program 23d memorized (stored) in the processing program storage section 23 is read out by the CPU 22, and the CPU 22 perform processing on the flowchart shown in FIG. 21 in accordance with the processing program 23d.

By following the flowchart in FIG. 21, the processing of creating and displaying a developed view will be described below.

Upon start of the operation by the image processor 3D, the CPU 22 reads out the processing program 23d in the processing program storage section 23 and starts the processing in accordance with the processing program 23d. The CPU 22 in the first step S61 obtains image data as an original image inputted from the CCU 8 of the endoscopic observation apparatus 2 through the image input section 21.

Then, the CPU 22 in the next step S62 performs upstream processing on the obtained image data such as correction for distortion/aberration and noise removal. In step S63, the CPU 22 obtains the three-dimensional positions of a subject corresponding to the pixels within the image.

Figure 22:
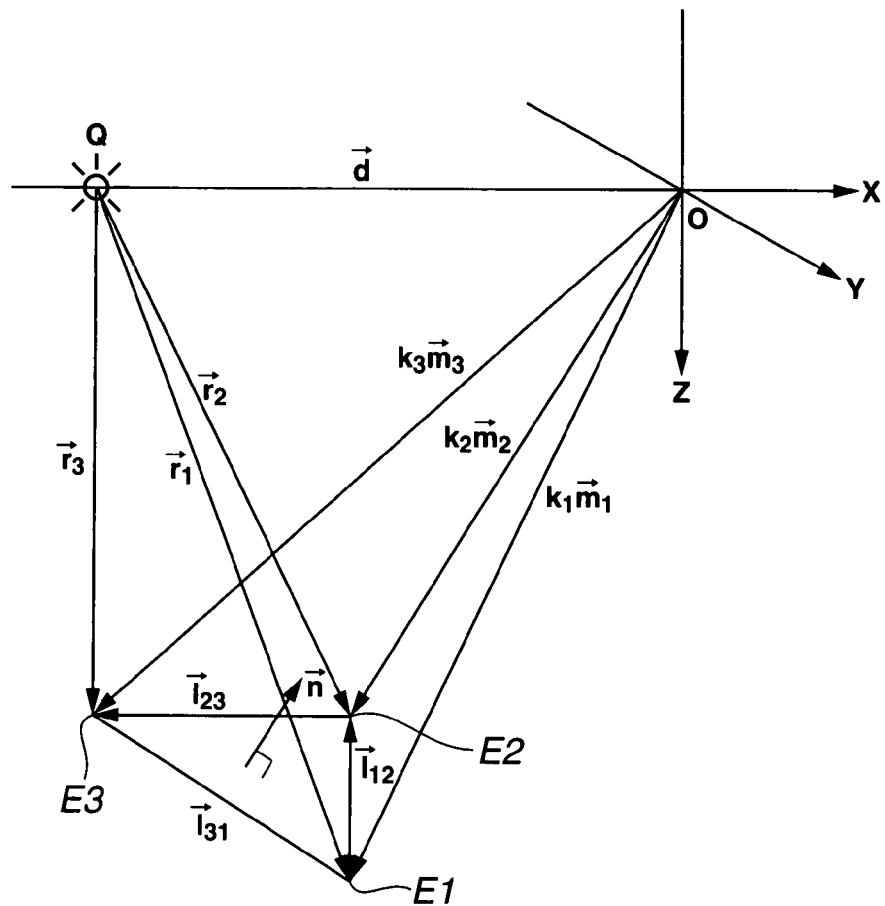
FIG. 22 is a diagram showing a positional relationship between corresponding points on an object, which correspond to pixels of a picked up image and a light source, for example.

As shown in FIG. 22, pixel corresponding points E1, E2 and E3 on the subject, which correspond to three pixels of an image shot by the image pickup means at the point-of-vision position O are extracted, and the positional relationship between the three-dimensional positions of the pixel corresponding points E1, E2 and E3 and the light source Q and the point of vision O provides:

[EQ 8]

$$\vec{r}_1 = \vec{d} - k_1 \vec{m}_1$$

$$\vec{r}_2 = \vec{d} - k_2 \vec{m}_2$$

$$\vec{r}_3 = \vec{d} - k_3 \vec{m}_3 \quad (8)$$

where the three-dimensional positions of the pixel corresponding points E1, E2 and E3 are $k_1 m_1$, $k_2 m_2$, and $k_3 m_3$ (where $m_1$, $m_2$ and $m_3$: unit vectors of one dimension), the vector from the point of vision O to the light source Q and the vectors from the light source Q to the three-dimensional positions of the pixel corresponding points E1, E2 and E3 are $r_1$, $r_2$ and $r_3$.

Based on (Eq. 8), a normal vector n of a plane including the three-dimensional positions of the pixel corresponding points E1, E2 and E3 is as:

[EQ 9]

$$\vec{n}_1 = \vec{l}_{12} \times \vec{l}_{23} = k_1 k_2 k_3 \begin{pmatrix} \frac{1}{k_3} \vec{m}_1 \times \vec{m}_2 + \frac{1}{k_1} \vec{m}_2 \times \vec{m}_3 + \\ \frac{1}{k_2} \vec{m}_3 \times \vec{m}_1 \end{pmatrix} \quad (9)$$

which is expressed by the ratios of the vector components $k_1$, $k_2$ and $k_3$.

Figure 23A:
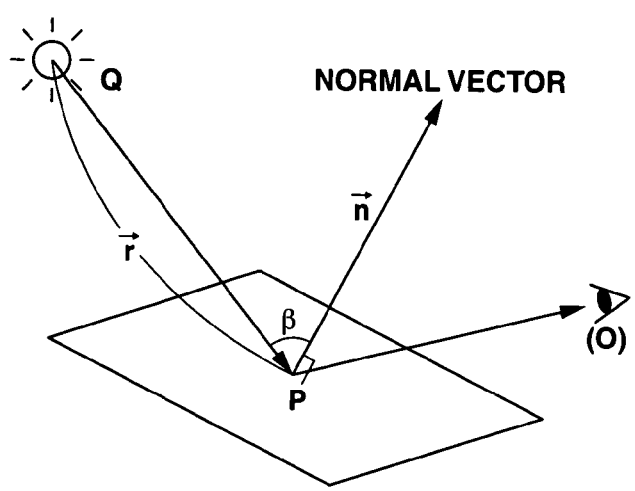
FIG. 23A is a diagram showing a state that light from a light source is reflected by the surface of an object.

In this case, the vector from the point E1 to the point E2 is $l_{12}$, the vector from the point E2 to the point E3 is $l_{23}$, and x expresses an outer product. Assuming that the surface of the subject (such as the inners of the esophagus) the image of which is to be picked up has a diffuse reflectance that reflects light uniformly in all directions as shown in FIG. 23A, the intensity values $I_1$, $I_2$ and $I_3$ of the pixel corresponding points E1, E2 and E3 are expressed by:

[EQ 10]

$$I_1 = h I_q \cos \beta_1 / |\vec{r}_1|^2$$

$$I_2 = h I_q \cos \beta_2 / |\vec{r}_2|^2$$

$$I_3 = h I_q \cos \beta_3 / |\vec{r}_3|^2 \quad (10)$$

where h is the diffuse reflectance of the surface of a subject, Iq is the luminous intensity of the light source Q, and β is an angle formed by the normal vector n of the surface of the subject at the point P and the vector r from the light source Q to the point P. The point P in FIG. 23A is a representative of the pixel corresponding points E1, E2 and E3 in FIG. 22 (therefore, the vector r is a representative of the vectors $r_1$, $r_2$ and $r_3$ in FIG. 22).

Next, the CPU 22 calculates the three-dimensional position of the subject, which corresponds to picked up pixels by defining and assuming the satisfaction of conditions (a) and (b) below.

If conditions:

(a) the distance between the point-of-vision position O and the light source Q < the distance between the point-of-vision position O and the three-dimensional positions of the pixel corresponding points E1, E2 and E3, that is, |d| is much less than $|r_m|$ (or |d| is much less than |r| where m=1 to 3); and (b) the three dimensional positions of the pixel corresponding points E1, E2 and E3 are close are satisfied,

[EQ 11]

$$k_1 : k_2 : k_3 \approx 1/\sqrt{I_1} : 1/\sqrt{I_2} : 1/\sqrt{I_3} \quad (11)$$

is obtained.

Figure 23B:
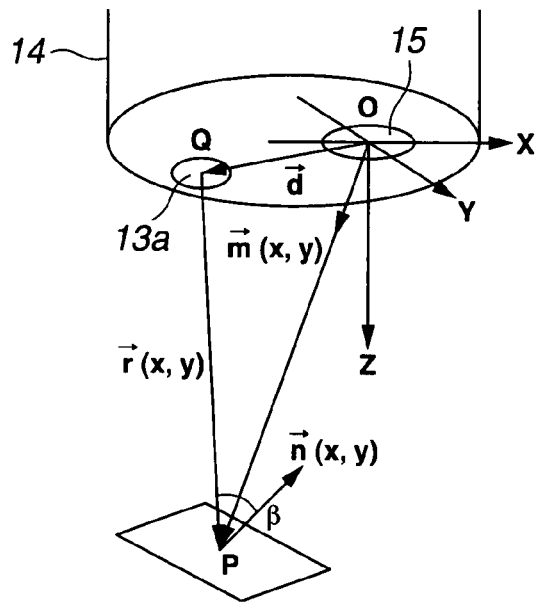
FIG. 23B is a diagram specifically showing the state in FIG. 23A.

The condition (a) is satisfied if the absolute value of r is larger than the absolute value of d as shown in FIG. 23B. The condition (b) may be satisfied in most cases when an image of the inners of a tubular one such as the esophagus is to be picked up. FIG. 23B shows an enlarged view of the distal end surface part of the distal end 14 of the insertion section.

A distal end surface (or illumination lens) 13a of the light guide 13 faces the distal end surface and outputs illumination light. In other words, the distal end surface 13a of the light guide 13 corresponds to the light source Q in FIGS. 22 and 23A. The objective 15 of the image pickup means (image pickup apparatus 17) corresponding to the point of vision O is placed adjacent to the distal end surface 13a.

From (Eq. 11) above, The ratio among $k_1$, $k_2$ and $k_3$ are obtained, and the normal vector n is obtained.

Figure 24:
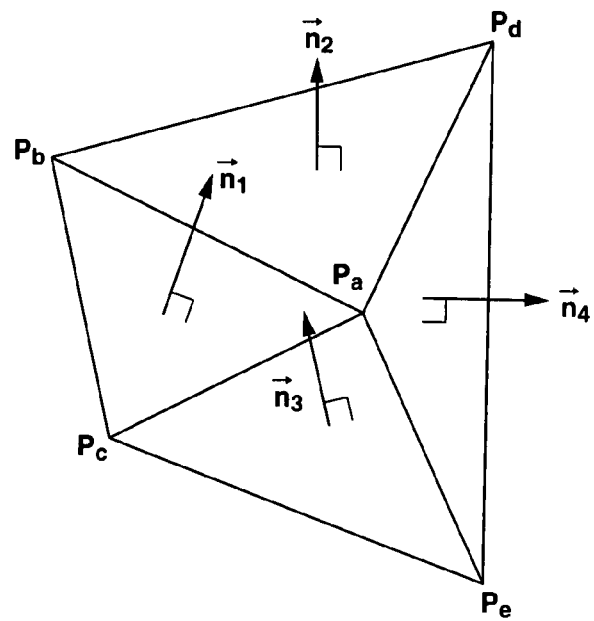
FIG. 24 is a diagram showing multiple normal vectors defined around corresponding points.

Since a pixel corresponding point on the surface of a subject, which corresponds to each pixel within an image, is adjacent to multiple pixel corresponding points, normal vectors $n_1$ to $n_4$ can be calculated for planes having the three points at points Pb to Pe around one pixel corresponding point Pa as shown in FIG. 24. Therefore, the average vector of the multiple normal vectors $n_1$ to $n_4$ may be calculated, and the average vector may be handled as the normal vector of the pixel corresponding point.

By assuming that the surface of a subject has diffuse reflection and rewriting the angle β as shown in FIG. 23A, the intensity value I(x,y) of each pixel corresponding point P(x,y) can be expressed by:

[EQ 12]

$$I_{(x,y)} = hI_q \cos\beta/r^2 = hI_q \vec{n}_{(x,y)} \cdot \vec{r}_{(x,y)}/|\vec{r}_{(x,y)}|^3 \quad (12)$$

where h is a diffuse reflectance of the surface of a subject, Iq is the luminous intensity of the light source Q, and β is an angle formed by the normal vector n (x,y) of the surface of a subject at the point P and the direction r(x,y) of the light source.

The direction r(x,y) of the light source at the point P can be expressed by:

[EQ 13]

$$\vec{r}_{(x,y)} = k_{(x,y)} \vec{m}_{(x,y)} - \vec{d} \quad (13)$$

where, as shown in FIG. 23B, the vector from the point of vision O of the objective 15 to the light source Q is d, the unit vector from the point of vision O to the position P of a subject is m(x,y), and the distance OP is k(x,y).

Figure 25:
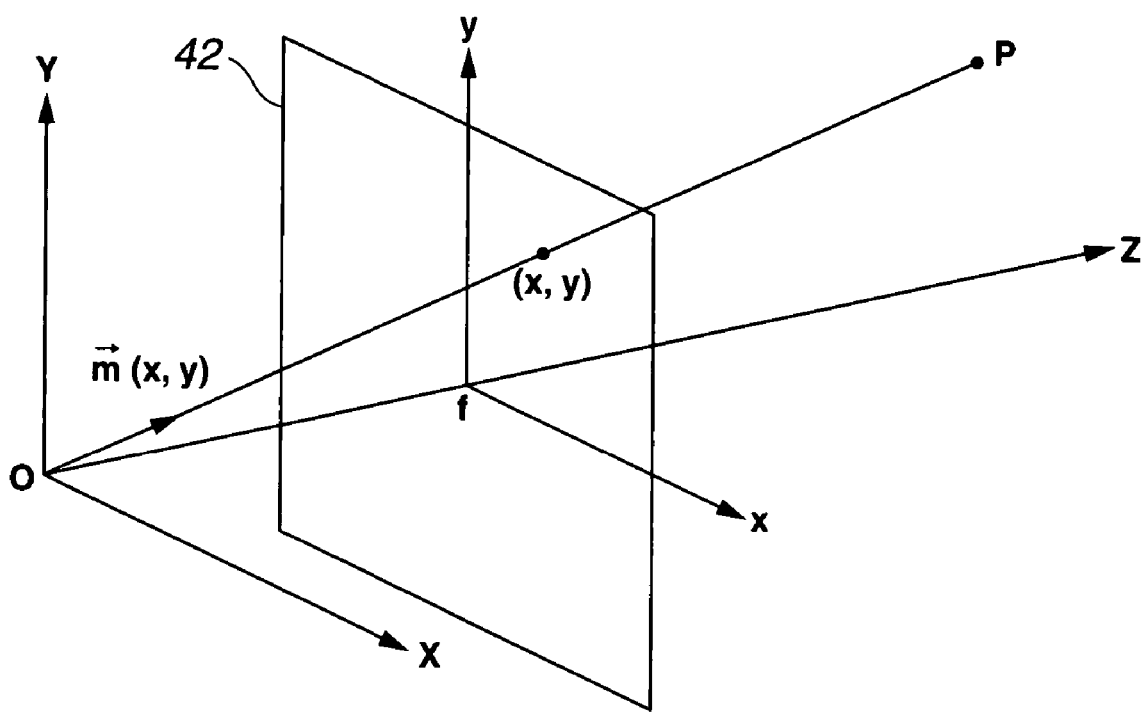
FIG. 25 is a diagram showing that a vector m passes through a position on an image.

Since the vector m(x,y) passes through the position (x,y) on the image on the image pickup plane 42 (of the CCD 16) as shown in FIG. 25, the vector m(x,y) is as:

[EQ 14]

$$\vec{m}_{(x,y)} = \begin{pmatrix} x/\sqrt{x^2 + y^2 + f^2} \\ y/\sqrt{x^2 + y^2 + f^2} \\ f/\sqrt{x^2 + y^2 + f^2} \end{pmatrix} \quad (14)$$

where f is the focal length of the image pickup apparatus 17. The intensity value I(x,y) of each pixel on the image can be expressed by:

[EQ 15]

$$I_{(x,y)} = hI_q \vec{n}_{(x,y)} \cdot (k_{(x,y)} \vec{m}_{(x,y)} - \vec{d})/|k_{(x,y)} \vec{m}_{(x,y)} - \vec{d}|^3 \quad (15)$$

Since all of them in (Eq. 15) except for k(x,y) are known, the CPU 22 calculates k(x,y) based on (Eq. 15) and calculates the three-dimensional position (X,Y,Z) corresponding to each pixel (x,y) on the image based on:

[EQ 16]

$$\begin{pmatrix} X \\ Y \\ Z \end{pmatrix} = k_{(x,y)} \vec{m}_{(x,y)} = k_{(x,y)} \begin{pmatrix} x/\sqrt{x^2 + y^2 + f^2} \\ y/\sqrt{x^2 + y^2 + f^2} \\ f/\sqrt{x^2 + y^2 + f^2} \end{pmatrix} \quad (16)$$

The CPU 22 in the next step S64 estimates a straight line passing through the center of the three-dimensional form obtained by step S63 (the form obtained based on the three-dimensional positions of pixel corresponding points).

Figure 26:
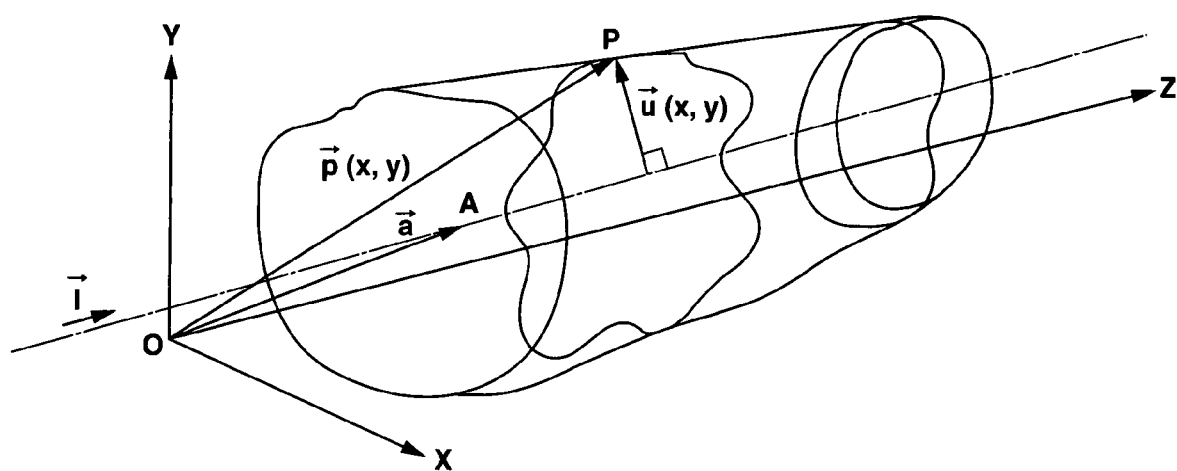
FIG. 26 is an explanatory diagram for calculating the straight line passing through the center of a three-dimensional form.

The vector u(x,y) drawing a straight line vertically from the point P of a three-dimensional form is expressed by:

[EQ 17]

$$\vec{u}_{(x,y)} = \vec{a} - \vec{p} + \frac{(\vec{p} - \vec{a}) \cdot \vec{l}}{|\vec{l}|^2} \vec{l} \quad (17)$$

where, as shown in FIG. 26, the vector from the point of vision O to the point P of the three-dimensional form is p, the vector to an arbitrary point A on the straight line is a, and the direction vector of the straight line is l.

When the estimated three-dimensional form exhibits a form close to a cylinder, the straight line passing through the center of the three-dimensional form is considered as being present at an equal distance from the three-dimensional positions of the three-dimensional form corresponding to the pixels. Therefore, the CPU 22 estimates an arbitrary dimension r (which is radius of the cylinder), the direction vector l of the straight line and the vector a to the point A by least square method such that the total sum of the differences between the vector u(x,y) obtained by (Eq. 17) and the arbitrary dimension r can be minimum, as expressed by:

[EQ 18]

$$\Sigma(|\vec{u}_{(x,y)}|-r)^2 \to \min \quad (18)$$

Figure 27:
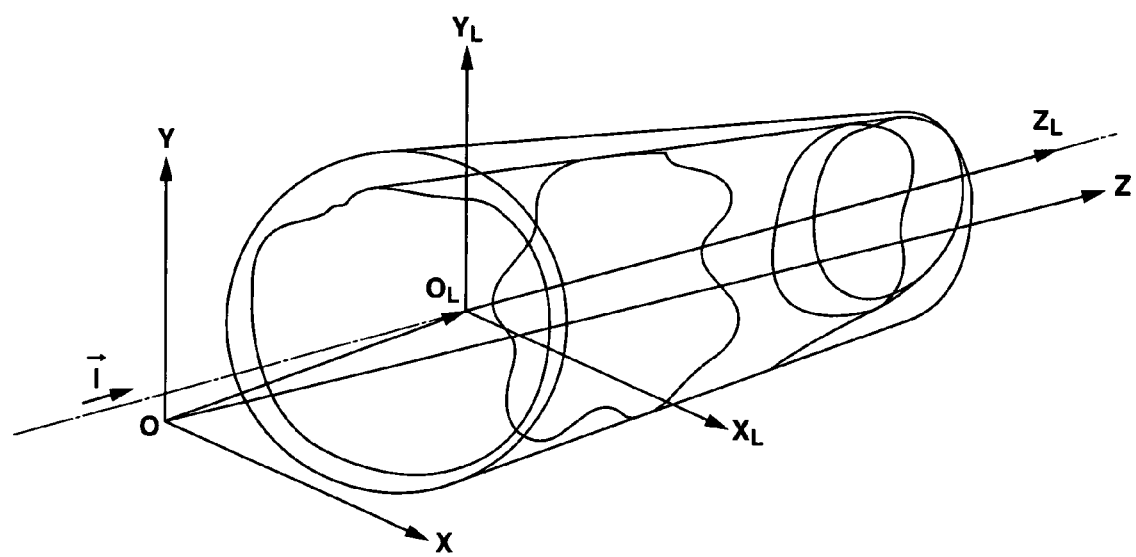
FIG. 27 is an explanatory diagram of conversion from a coordinate system of a three dimensional form to a coordinate system based on a straight line.

The CPU 22 in the next step S65 obtains, from the relationship shown in FIG. 27, a parameter rotation matrix R and a translational matrix M for converting the three-dimensional positions of the three-dimensional form corresponding to pixels from the coordinate system X-Y-Z to the coordinate system $X_L$-$Y_L$-$Z_L$ with reference to the straight line.

Based on the vector Z in the Z-direction of the coordinate system X-Y-Z and the vector l of the straight line, the unit vector v(vx,vy,vz) and the angle γ are as:

[EQ 19]

$$\vec{v} = \vec{Z} \times \vec{l}$$

$$\gamma = \cos^{-1}(\vec{Z} \cdot \vec{l}) \quad (19)$$

Therefore, the rotation matrix R and translational matrix M are as:

[EQ 20]

$$R = \begin{pmatrix} \cos\gamma + v_x^2(1-\cos\gamma) & v_x v_y(1-\cos\gamma) \cdot v_z \sin\gamma & v_x v_z(1-\cos\gamma) \cdot v_y \sin\gamma^2 \\ v_y v_x(1-\cos\gamma) + v_z \sin\gamma & \cos\gamma + v_y^2(1-\cos\gamma) & v_y v_z(1-\cos\gamma) - v_x \sin\gamma \\ v_z v_x(1-\cos\gamma) + v_y \sin\gamma & v_z v_y(1-\cos\gamma) + v_x \sin\gamma & \cos\gamma + v_z^2(1-\cos\gamma) \end{pmatrix} \quad (20)$$

$$M = \begin{pmatrix} a_x \\ a_y \\ a_z \end{pmatrix} \quad (21)$$

where, the vector a=($a_x$,$a_y$,$a_z$) is defined as the translational matrix M.

The CPU 22 in the next step S66 converts the three-dimensional positions expressed by the coordinate system X-Y-Z to those in the coordinate system $X_L$-$Y_L$-$Z_L$. The conversion equation is:

[EQ 21]

$$P_L = R^{-1}(P-M) \quad (22)$$

Figure 28A:
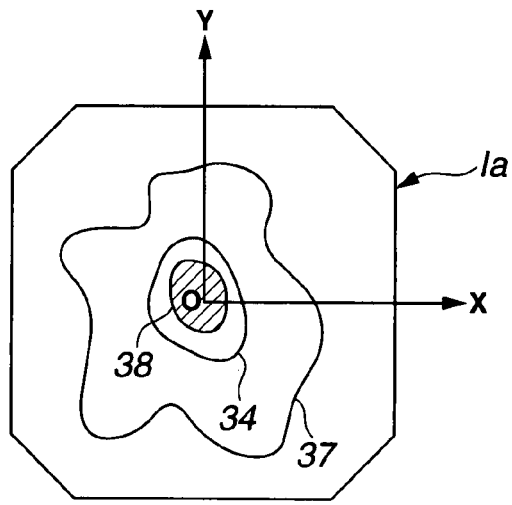
FIG. 28A is a diagram showing an endoscopic image obtained by a direct-view type endoscope.
Figure 28B:
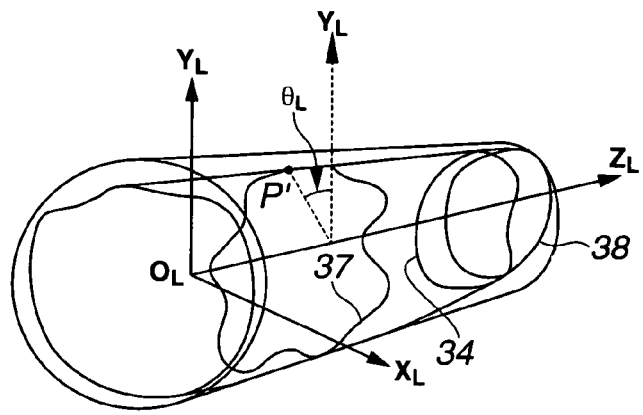
FIG. 28B is an explanatory diagram showing a relationship between an endoscopic image and the surface of a cylinder modeling the esophagus.

The CPU 22 in the next step S67 further projects the three-dimensional position $P_L$=($X_L$, $Y_L$, $Z_L$) of each pixel corresponding point converted as shown in FIG. 28B, which corresponds to the endoscopic image Ia in FIG. 28A, by (Eq. 22) to the surface of the cylinder about ZL.

For the cylinder, a value close to the size of a tubular part such as the esophagus is defined. For example, the value resulting from the averaging of inner radiuses of a tubular part is used as the diameter of the cylinder.

For example, the squamocolumnar junction 37 and (esophagogastric) junction 34 and a dark part junction 38 on the endoscopic image Ia in FIG. 28A correspond to the three-dimensional form parts indicated by the same reference numerals 37, 34 and 38 in FIG. 28B, and each position of the three-dimensional form parts is projected to the surface of the cylinder about ZL, which is indicated by a thick line.

The converted three-dimensional position $P_L$=($X_L$,$Y_L$, $Z_L$) is obtained by:

[EQ 22]

$$\theta_L = \tan\left(\frac{X_L}{Y_L}\right) \quad (23)$$

$$Z_L = Z_L$$

where the coordinate system of the surface of the cylinder is $\theta_L$-$Z_L$.

Figure 28C:
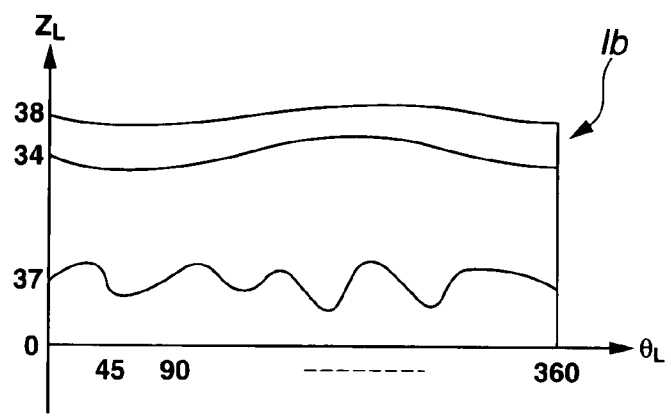
FIG. 28C is a diagram showing a developed view created from the endoscopic image projected on the surface of the cylinder in FIG. 28B.

The position C($\theta_L$,$Z_L$) on the surface of the cylinder, corresponding to each of all pixels of the image, is obtained, and the intensity value of each pixel is pasted to the coordinate system $\theta_L$-$Z_L$. Then, the developed view Ib shown in FIG. 28C is created. The intensity value is the intensity value of each color signal for a full-color image.

Figure 29:
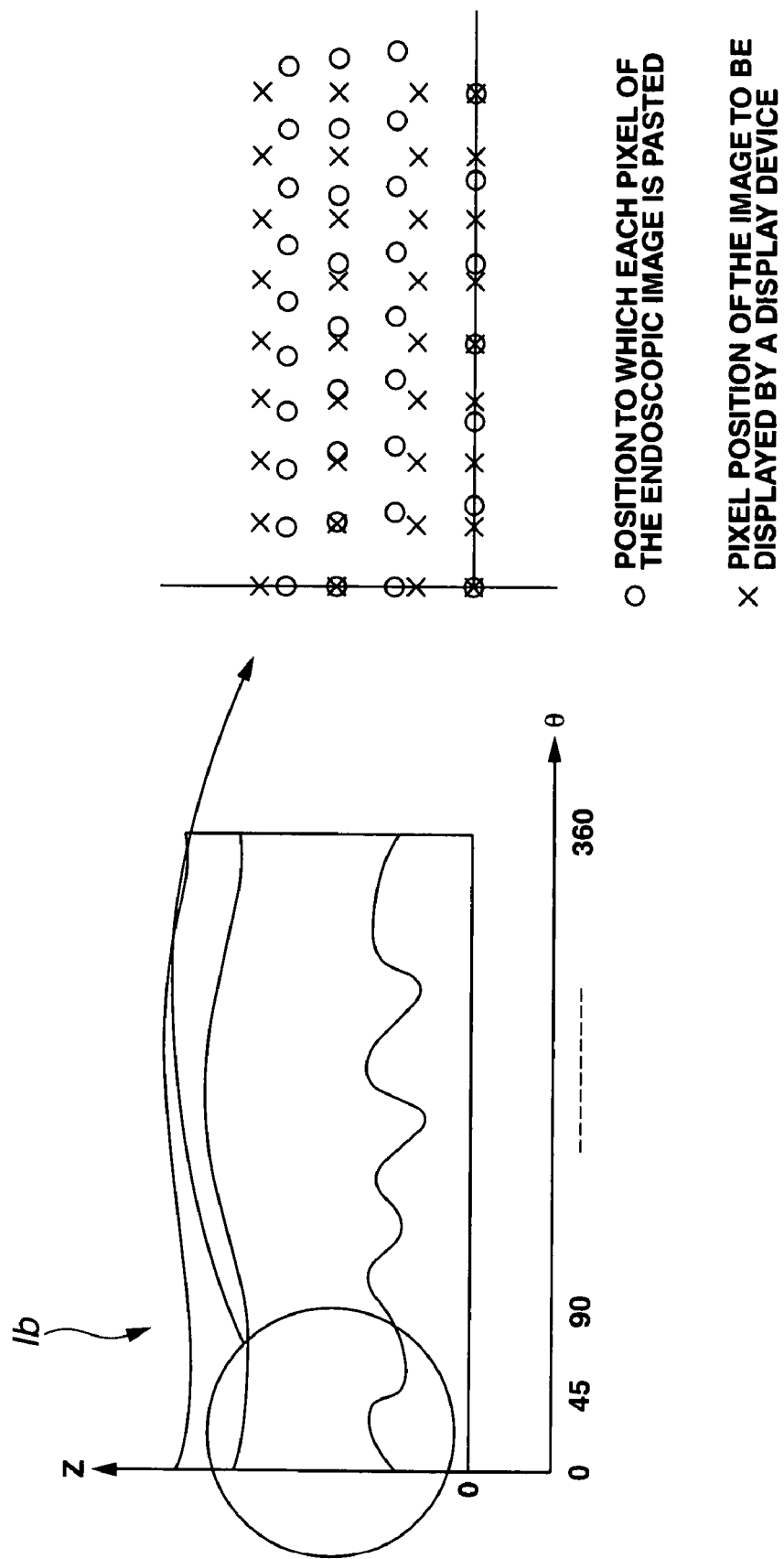
FIG. 29 is an explanatory diagram for creating a developed view by interpolation processing.

The pixels pasted to the surface of the cylinder as shown in FIG. 28C or 29 exist unevenly, and the roughness increases as the value of $Z_L$ increases (that is, the roughness increases as the distance from the point of vision to the position of the image part increases).

Each pixel pasted as shown in the partial enlarged view in FIG. 29 may not often agree with each pixel position of the image to be displayed on a display device. Therefore, an image to be displayed on a display device, that is, the developed view Ib, is created by interpolation processing.

Figure 30:
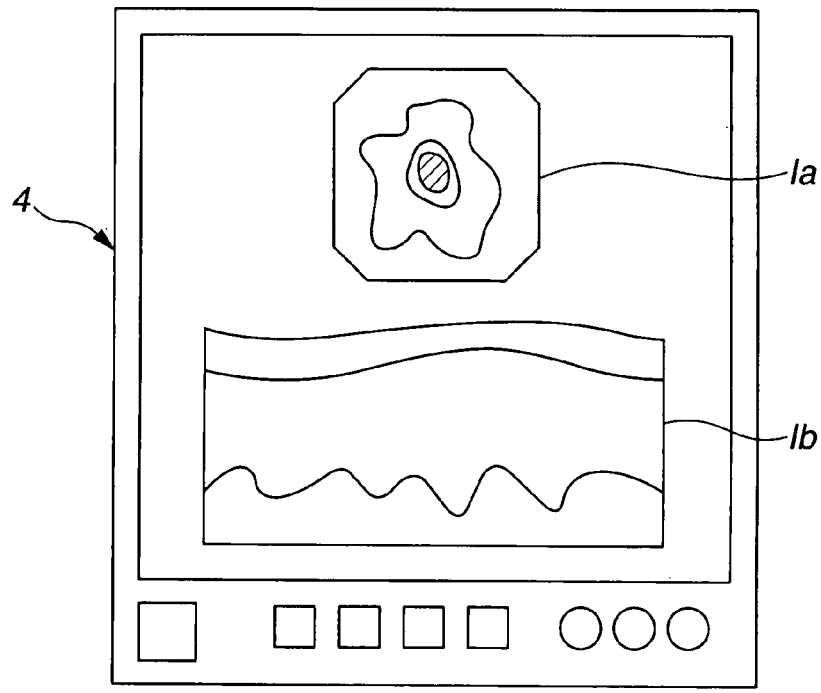
FIG. 30 is a diagram showing an endoscopic image and developed view, which are developed on a display device.

The CPU 22 in step S68 performs the interpolation processing and creates an image, which can be displayed on a display device such as the display monitor 4, that is, the developed view Ib. The CPU 22 in the next step S69 outputs the endoscopic image Ia and the developed view Ib to the display monitor 4. Then, as shown in FIG. 30, the display monitor 4 displays the endoscopic image Ia in step S10 and the developed view Ib. Then, the processing of displaying the developed view Ib ends.

The present embodiment provides advantages below.

By displaying how the columnar epithelium continuously present from the esophagogastric junction extends and distinctive forms of the columnar epithelium and the squamous epithelium on (an image of) a developed view, a surgeon can easily observe them in a manner allowing easier comparison, for example. Therefore, the diagnoses on a tubular part such as Barrett's esophagus can be more easily performed.

In other words, in a prior art, the endoscopic image Ia in FIG. 30 is only displayed, and the endoscopic image Ia has an image having the two-dimensional projection of the inners of a tubular part. For example, each part is displayed which is scaled down based on the value of the distance in the direction of depth (the axial direction of the tubular part).

Therefore, the parts having different values in the direction of depth cannot be compared easily since the scales of the parts are different based on the distances in the direction of depth.

On the other hand, according to the present embodiment, the three-dimensional positions of the inners of a tubular part, which correspond to pixels of the endoscopic image Ia, which is picked up two-dimensionally, are calculated, and the position information of each pixel is converted to the position information in the circumferential direction and distance component information in the direction of the near/close center axis of the luminalis, which is orthogonal to the circumferential direction based on the calculation of the three-dimensional positions. Furthermore, the image is projected to the surface of a cylinder defined in an average size, for example, of the tubular part and is displayed by developing the intensity information of each part based on the positional information in the circumferential direction, that is, the value of the angle.

Thus, according to the present embodiment, positions having different directions of depth can be displayed at an even scale in the circumferential direction, which therefore allows easy comparison among parts at different places and further allows objective and easy comparison, for example, with past cases.

Therefore, according to the present embodiment, an image of a developed view allowing an easy diagnose of a tubular part can be created, and an image processing apparatus and image processing method, which are greatly effective for diagnoses, can be provided.

Embodiment 5

Next, with reference to FIGS. 31 to 33, Embodiment 5 of the present invention will be described. The configuration of an image processor of the present embodiment is the same as that of Embodiment 4 except that a processing program, which is different from the processing program 23d stored in the processing program storage section 23 in FIG. 19, is adopted.

While, in Embodiment 4, the three-dimensional position of the pixel corresponding point, which corresponds to each pixel, is estimated from one image, multiple endoscopic images are picked up, and three-dimensional positions on a subject, which correspond to the picked up multiple endoscopic images, are calculated in the present embodiment as described below.

Processing below after the calculation of three-dimensional positions is the same as that of Embodiment 4. FIG. 31 shows a flowchart for calculating a three-dimensional position in the present embodiment. FIG. 32 shows schematic operations of the processing details. FIG. 33 shows a state that an amount of shift between a template image and a reference image is obtained.

Figure 31:
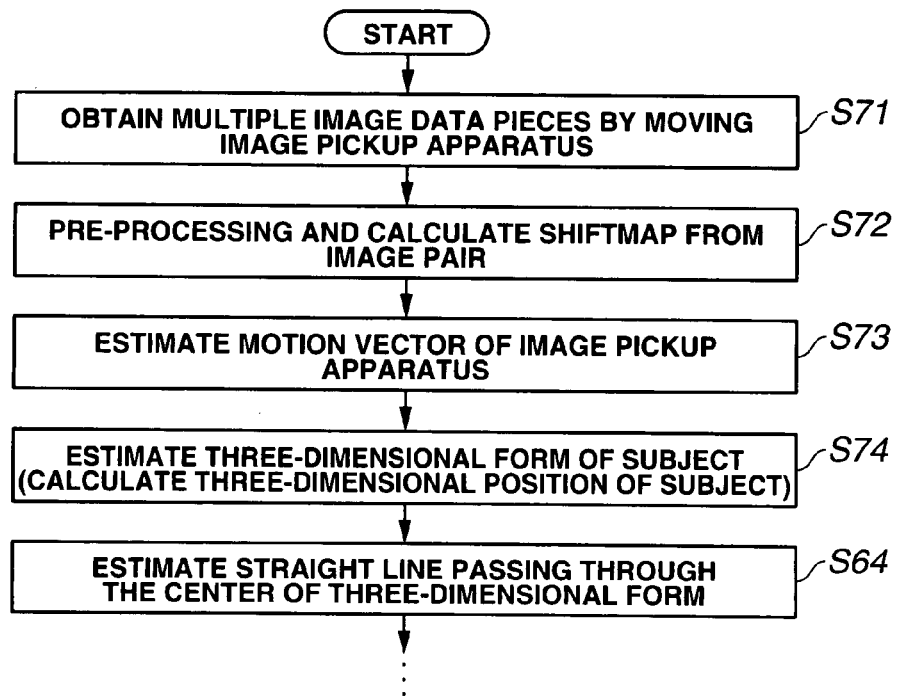
FIG. 31 is a flowchart showing a part of processing steps for creating a developed view in Embodiment 5 of the present invention.
Figure 32:
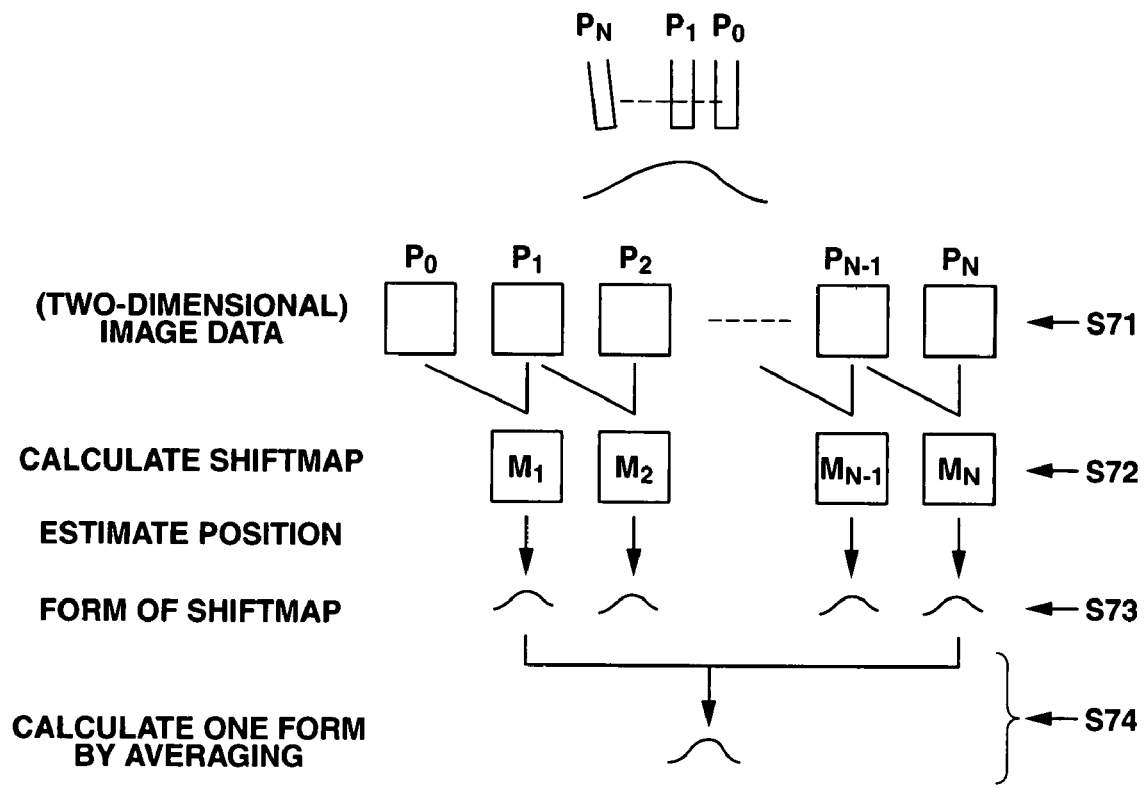
FIG. 32 is an explanatory diagram of processing details in FIG. 31.

With reference to FIGS. 31 and 32, a process until the calculation of three-dimensional image data will be described.

As described in step S71, the CPU 22 of the image processor 3 picks up images by moving the image pickup apparatus 17 of the distal end 14 of the insertion section 11 of the endoscope 6 and obtains multiple image data pieces.

The picked up multiple image data is temporarily stored in the image storage section 24 within the image processor 3 through the image input section 21.

In other words, two-dimension image data pieces at slightly different positions from each other are obtained by moving the image pickup apparatus 17 (of the distal end 14 of the endoscope 6) about one subject.

A state that the pickup operation is being performed by moving the distal end side of the insertion section 11 is shown in FIG. 32. Here, the image data picked up by moving the distal end side from $P_0$ to $P_N$ is indicated by a square. The CPU 22 in the next step S72 applies pre-processing such as correction for distortion/aberration on multiple images obtained in step S71, and distortions of the images are corrected.

Distortions on images are corrected by applying processing of correction for distortion/aberration to images since image data of an endoscope, which is transmitted from the endoscopic observation apparatus 2, may have a distortion due to the use of a wide-angle lens as the objective.

The CPU 22 in step S72 traces a corresponding point by using the corrected multiple images (image pair), that is, selects one image (template image) representing a subject, selects multiple points on the image and traces how the points move on a reference image, which is different. The corresponding-point tracing will be elaborated.

Figure 33:
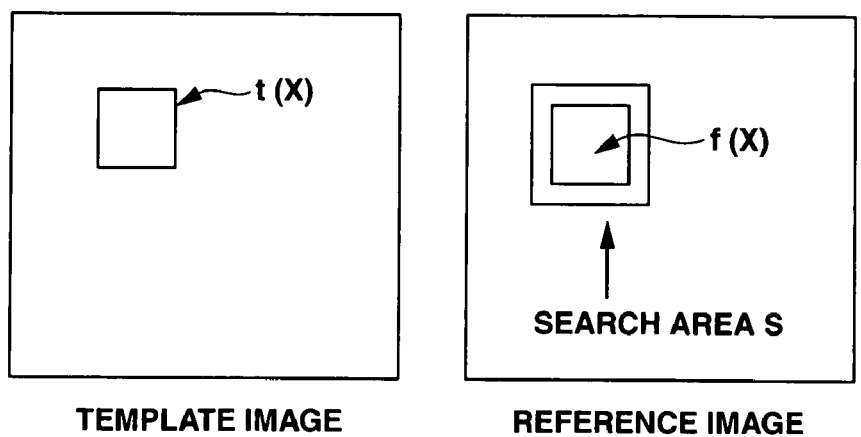
FIG. 33 is an explanatory diagram of a state that an amount of shift between a template image and a reference image is calculated.

The corresponding-point tracing, as shown on the left side of FIG. 33, defines a rectangular area (window) about one point as t(x) on the template image of a subject to be detected, and, as shown on the right side of FIG. 33, defines a search area S having a certain size on a reference image, performs block matching processing between the corresponding area f(x) within the search area S and the rectangular area t(x) on the template image by correlation calculation to perform a calculation for obtaining an area having a highest correlated value, and obtains the direction of movement and the amount of movement of the reference image with respect to the template image in that case.

For example, the correlation D(u,v) of a normalized equation (Eq. 24) below:

[EQ 23]

$$D(u, v) = \frac{\iint s[(f(x+u, y+v) - \langle f \rangle)(t(x,y) - \langle t \rangle)] dx dy}{\sqrt{\iint s(f(x+u, y+v) - \langle f \rangle)^2 dx dy \iint (t(x, y) - \langle t \rangle)^2 dx dy}} \quad (24)$$

is used to calculate the correlated values, and the area having the highest one is obtained. Then, the direction of movement and the amount of movement are obtained in that case. Here, the double integral indicates the integral within the search area S, and <f> and <t> are averages of f(x+u,y+v) and t(x,y), respectively, within the S.

The block matching processing is not limited to correlation calculation, and the color matching technique disclosed in the specification of U.S. Pat. No. 4,962,540 is applicable thereto.

In this manner, a shiftmap describing the direction of the movement and the value of the travel of the point selected on the template image is obtained.

FIG. 32 also shows a state that shiftmaps $M_1$, $M_2$ and so on, are calculated from the obtained image data based on the adjacent image pickup points $P_0$ and $P_1$, and $P_1$ and $P_2$, for example, to perform the position estimation.

The CPU 22 in the next step S73 uses the shiftmaps obtained in step S72 to obtain the motion vector of the image pickup apparatus 17 by repetitive processing such as method of steepest descent, and the position of the subject and the relative positional relationship with the position of the image pickup apparatus 17 are obtained.

The CPU 22 in the next step S74 converts such that the positional relationships between the subject and the image pickup apparatus 17, which are obtained from the shiftmaps, can be within a same coordinate space and estimates a three-dimensional form of one subject by averaging the positions of the subject and image pickup apparatus 17 at each point (that is, calculates each three-dimensional position of the subject).

Figure 21:
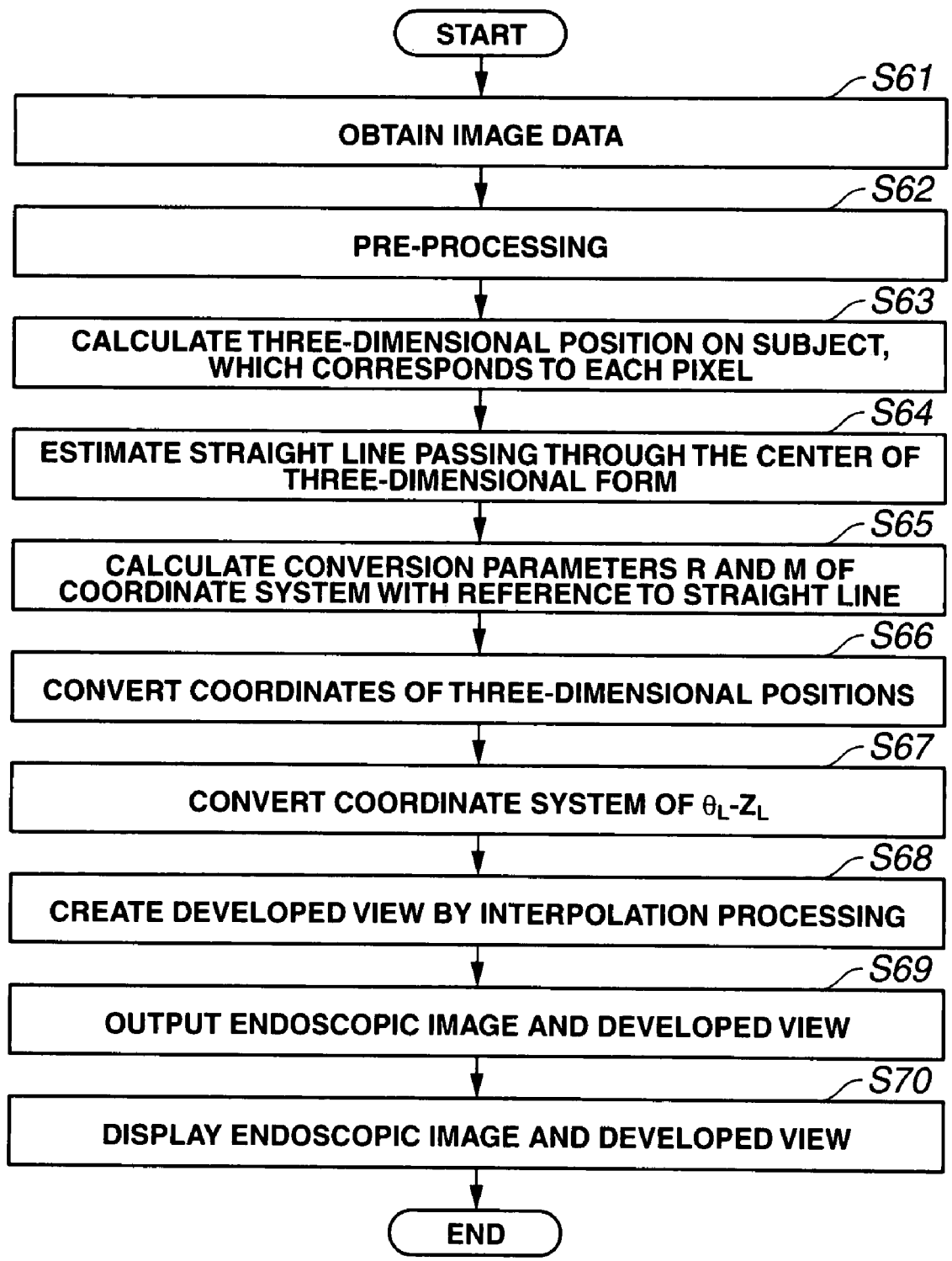
FIG. 21 is a flowchart showing processing steps for creating a developed view.

In this way, after the three-dimensional position of the subject is calculated, processing is performed such as the estimation of a straight line passing through the center of the three-dimensional form in step S64 in FIG. 21.

Like Embodiment 4, an image of a developed view suitable for diagnoses can be obtained in the present embodiment by using multiple images picked up by the image pickup apparatus 17.

Alternatively, a three-dimensional form may be estimated from one image by a shape-from-shading technique, and a developed view may be created from the estimated three-dimensional form, as disclosed in the document below:

Three-dimensional Form Reconstruction from an Endoscope Image Form Document: Computer Vision, by Shape from Shading Techniques for a Point Light Source at the Projection Center, Okaya and Deguchi, pp. 19-26, 1996

This document discloses a technique including focusing on curved lines on the surface of a tubular organ spaced apart from a light source (the light guide distal end surface 13a of the distal end 14) by an equal distance and describing and solving the evolution equations of the curved lines by partial differential equations to reconstruct (calculate) the three-dimensional form. The processing after the calculation of the three-dimensional form is the same processing as in Embodiment 4.

Embodiment 6

With reference to FIGS. 34 to 44C, Embodiment 6 of the present invention will be described next. It is an object of Embodiment 6 and subsequent embodiments to provide a medical image processing apparatus (more specifically, image processing apparatus for mucosa of the esophagus) and medical image processing method suitable for efficiently performing a diagnosis of Barrett's esophagus, for example, even for an endoscopic image of the esophagus, which is picked up by a direct-view endoscope. The background will be elaborated.

Since an image of a tubular part such as the inners of the esophagus, which is picked up by a direct-view type endoscope, has a tubular mucosa tissue (more specifically, epithelial tissue) picked up in a diagonal direction or direction close to the straight angle about the axial direction of the luminalis, the form spaced apart from the image pickup apparatus by different distances, may vary largely.

For this reason, it takes time to grasp the form and size, for example, only from the endoscopic image picked up by a direct-view type endoscope. Therefore, providing an image allowing easier grasping is highly convenient for a diagnosis. In other words, the object is greatly efficient.

Figure 34:
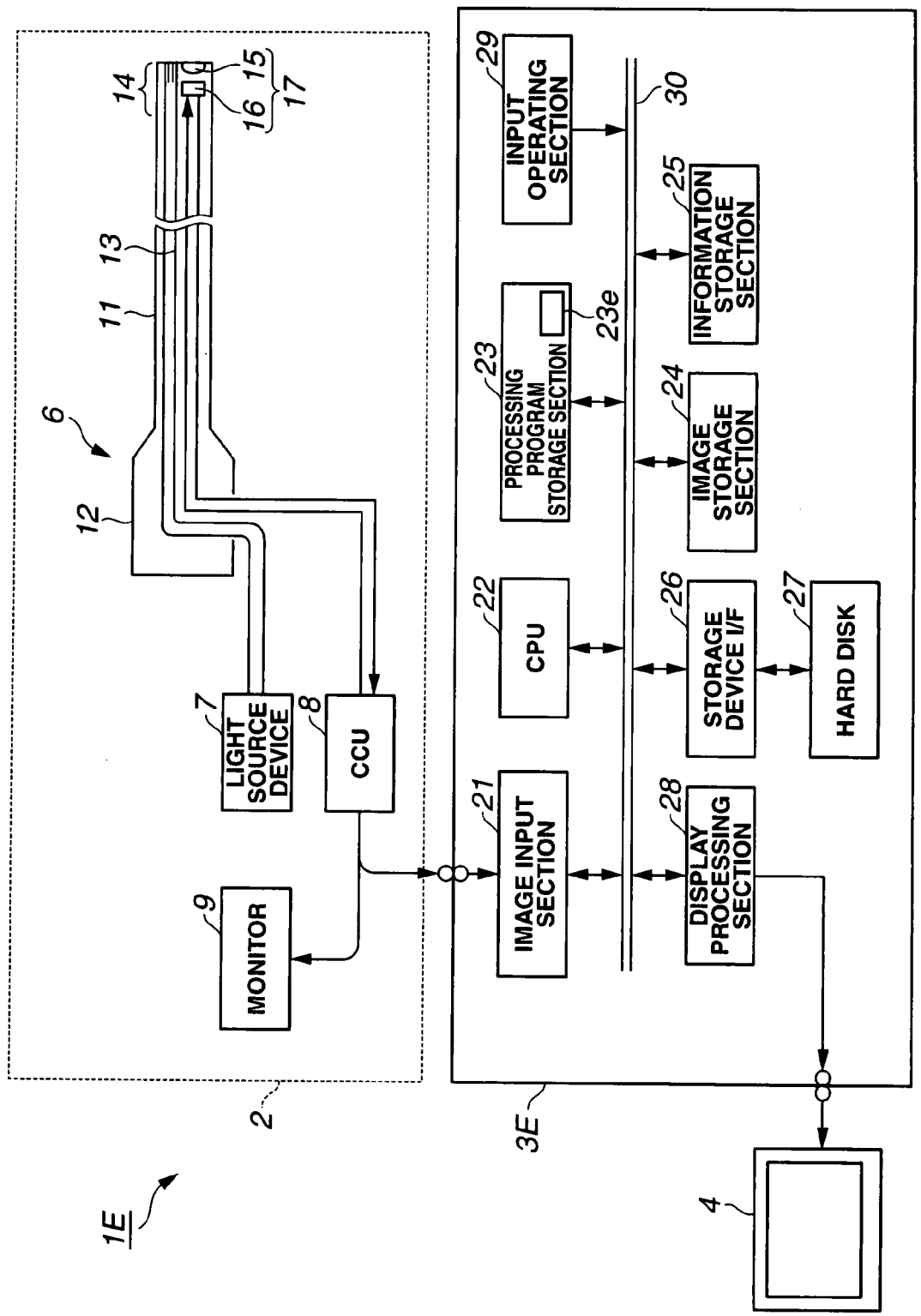
FIG. 34 is a block diagram showing a configuration of an endoscopic system including Embodiment 6 of the present invention.

An endoscopic system 1E shown in FIG. 34 has the same configuration in hardware as that of the endoscopic system 1 in FIG. 1. An image processor for mucosa of the esophagus (which will be simply abbreviated to image processor) 3E of the present embodiment additionally has a function of performing image processing for analyzing a feature value that Barrett's esophagus has by using an image of a developed view created by the image processor 3 in FIG. 1.

Thus, the image processor 3E in FIG. 34 includes a processing program 23e having a function of detecting a squamocolumnar junction and a function of performing an analysis for examining a feature value of Barrett's esophagus on the detected squamocolumnar junction in addition to the processing program 23a in the case of the image processor 3 in FIG. 1. Since the rest has the same configuration as that of Embodiment 1, the same reference numerals are given to the same components, the description of which will be omitted hereinafter.

Also in the present embodiment, as shown in FIG. 2, the insertion section 11 of the direct-view type endoscope 6 is inserted to a tubular organ or tubular part such as the esophagus 31, and an image of the mucosa of the inner wall of the esophagus 31 is picked up by the image pickup apparatus 17 provided in the distal end 14.

Figure 35:
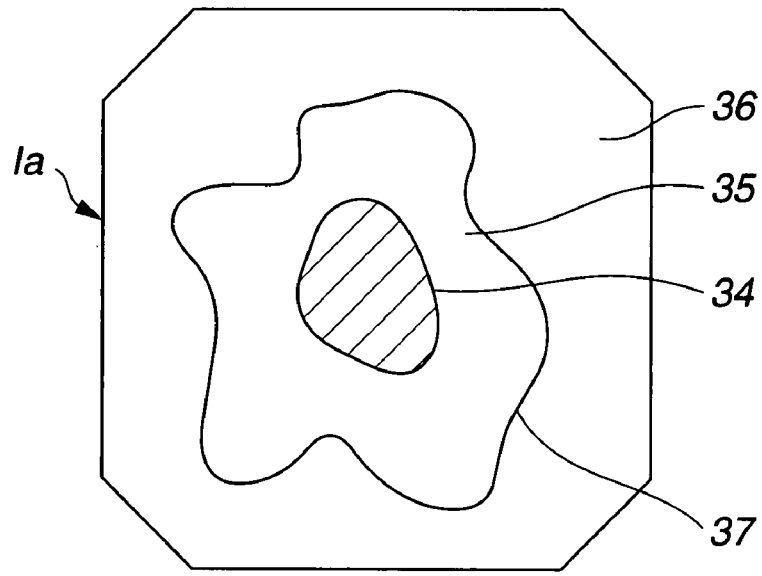
FIG. 35 is a diagram showing an endoscopic image picked up by an image pickup apparatus of the endoscope in FIG. 34.

FIG. 35 shows an example of the endoscopic image Ia of Barrett's esophagus, which is picked up by the direct-view type endoscope 6. Barrett's esophagus is the junction between the stomach and the esophagus, that is, the squamous epithelium 36, which is the mucosa of the esophagus, denatured to the columnar epithelium 35, which is the gastric mucosa or the Barrette's mucosa, continuously from the junction between the stomach and the esophagus, that is, the esophagogastric junction 34 to the oral cavity side. The disease, Barrett's esophagus, is diagnosed when the Barrett's mucosa occurs circumferentially on the section of the luminalis of the esophagus from the normal mucosa junction by 3 cm or longer.

In addition to the definition, a surgeon diagnoses Barrett's esophagus by using the endoscope 6 to observe how the denatured columnar epithelium 35 extends and/or a distinctive form of the squamocolumnar junction 37 which is the junction between the squamous epithelium 35 and the columnar epithelium 36.

The endoscopic image Ia in FIG. 35 displays, as the tubular part from the esophagus 31 to the inside of the stomach, the esophagogastric junction 34 around the darkest part, not shown, the columnar epithelium 35 outside of the margin of the esophagogastric junction 34, the squamocolumnar junction 37 outside thereof, and the squamous epithelium 36 outside of the squamocolumnar junction 37.

The present embodiment includes picking up an image of a subject in a tubular organ such as the esophagus 31 by the direct-view type endoscope 6, converting the picked up endoscopic image Ia geometrically, performing processing of creating a developed view therefrom, displaying the created developed view of the subject on the monitor 4 and detecting the squamocolumnar junction 37 from the created developed view.

Then, based on the detected distinctive form of the squamocolumnar junction 37, processing is performed including analyzing the form and outputting the analysis result.

More specifically, processing of determining either squamocolumnar junction or Barrett's esophagus by calculating the average value in the Z-direction of the squamocolumnar junction 37 and calculating a variance in the Z-direction of the squamocolumnar junction 37 and outputting a determination result (analysis result) on either squamocolumnar junction or Barrett's esophagus.

Figure 36:
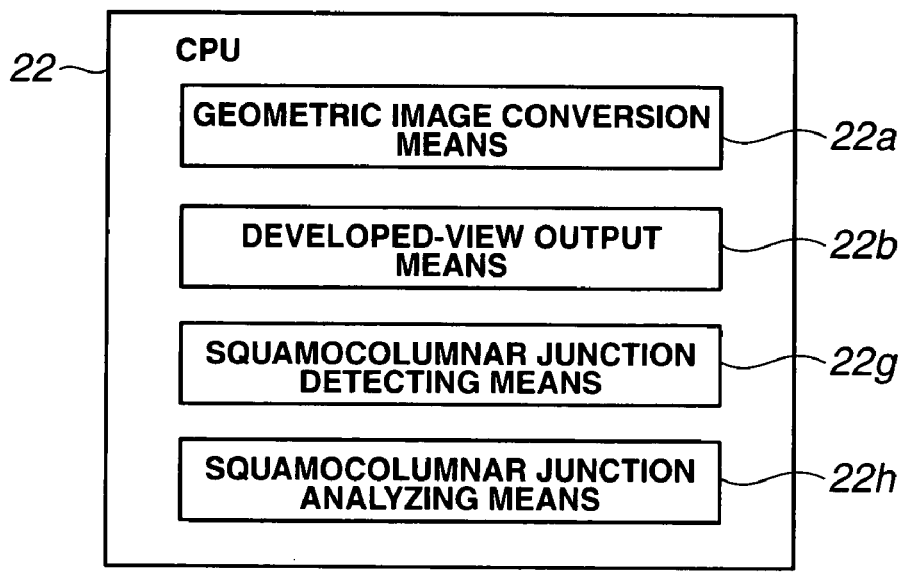
FIG. 36 is a diagram showing an image processing function by a CPU.

As shown in FIG. 36, the CPU 22 included in the image processor 3 includes geometric image conversion means (function) 22a for performing geometric conversion, developed-view output means (function) 22b for outputting an image of a developed view by the geometric conversion, squamocolumnar junction detecting means (function) 22g for detecting a squamocolumnar junction from a developed view, and squamocolumnar junction analyzing means (function) 22h for analyzing the form of a squamocolumnar junction and outputting the analysis result.

The squamocolumnar analyzing means 22h includes, specifically, squamocolumnar-junction average-value calculating means (function) for detecting the average value in the Z-axis direction of a squamocolumnar junction, squamocolumnar-junction variance calculating means (function) for calculating a variance in the Z-direction of a squamocolumnar junction, and determining means (function) for determining whether the variance exhibits a squamocolumnar junction or Barrett's esophagus.

In the present embodiment, the geometric image conversion means 22a, developed-view output means 22b, squamocolumnar junction detecting means 22g and squamocolumnar analyzing means 22h shown in FIG. 36 are implemented by software, and the CPU 22 reads out a processing program 23e memorized (stored) in the processing program storage section 23 therefore. Then, the CPU 22 performs the processing steps shown in FIG. 37 in accordance with the processing program 23e.

The present embodiment includes, as described later, creating a developed view Ib from an endoscopic image Ia resulting from the pickup of a surrounding part of an esophagogastric junction of the esophagus by the direct-view type endoscope 6, detecting the squamocolumnar junction from the developed view Ib, and determining whether the form of the squamocolumnar junction 37 has a typical form of Barrett's esophagus or not, that is, the form has a feature value exhibited when the squamocolumnar junction 37 has a complex form or not, for example, whether the points at the squamocolumnar junction 37 form a serrated line or not by calculating variances at the points of the squamocolumnar junction.

Then, typical Barrett's esophagus having a complex form is objectively determined for example, when the points at the squamocolumnar junction 37 on the picked up endoscopic image Ia form a serrated line in the direction of the luminalis.

Next, with reference to FIG. 37, operations of the present embodiment will be described.

Upon start of the operation by the image processor 3, the CPU 22 reads out the processing program 23e in the processing program storage section 23 and starts the processing in accordance with the processing program 23e. The CPU 22 in the first step S81 obtains image data of an endoscopic image Ia inputted from the CCU 8 of the endoscopic observation apparatus 2 through the image input section 21.

Figure 38:
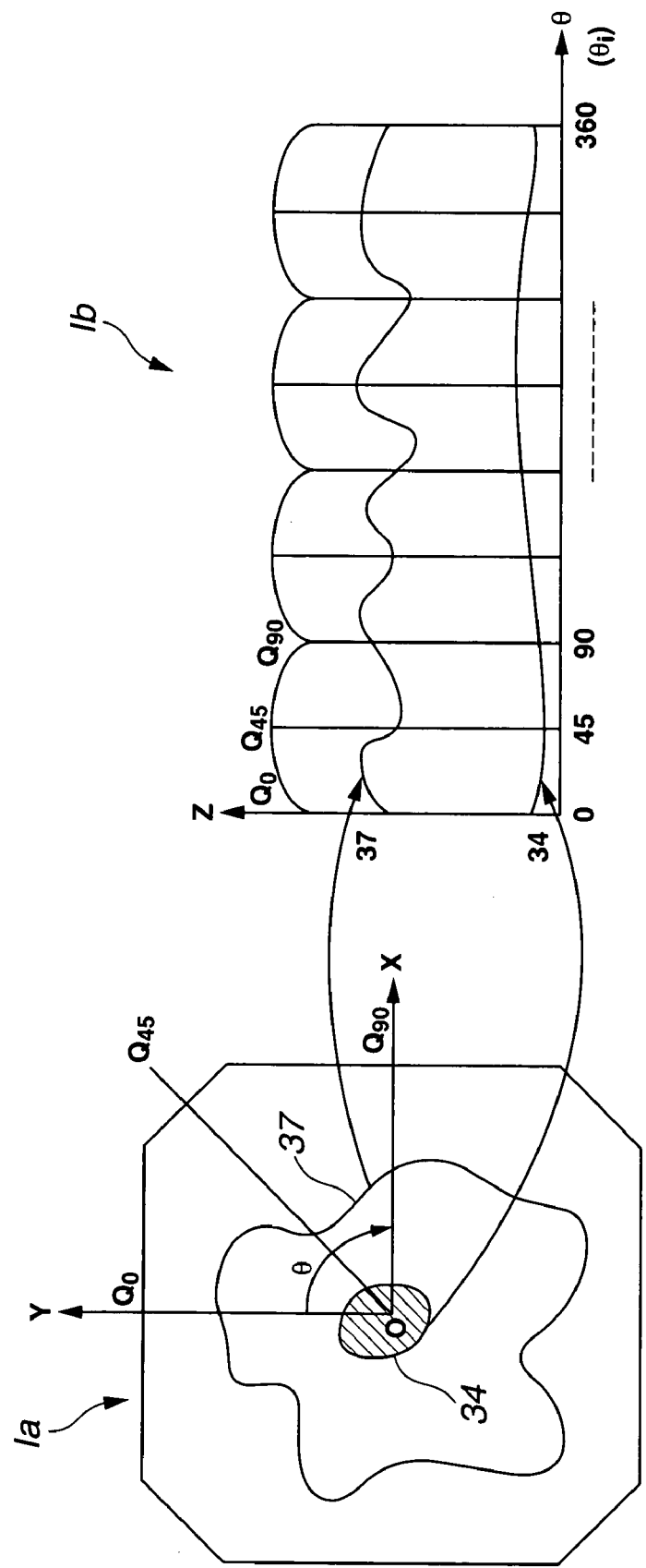
FIG. 38 is a diagram showing a relationship between an endoscopic image and a created developed view.

Then, the CPU 22 in the next step S82 performs upstream processing on the obtained image data such as correction for distortion/aberration and noise removal and in step S83 performs processing of creating a developed view Ib shown on the right side of FIG. 38 from the endoscopic image Ia shown on the left side.

Figure 39:
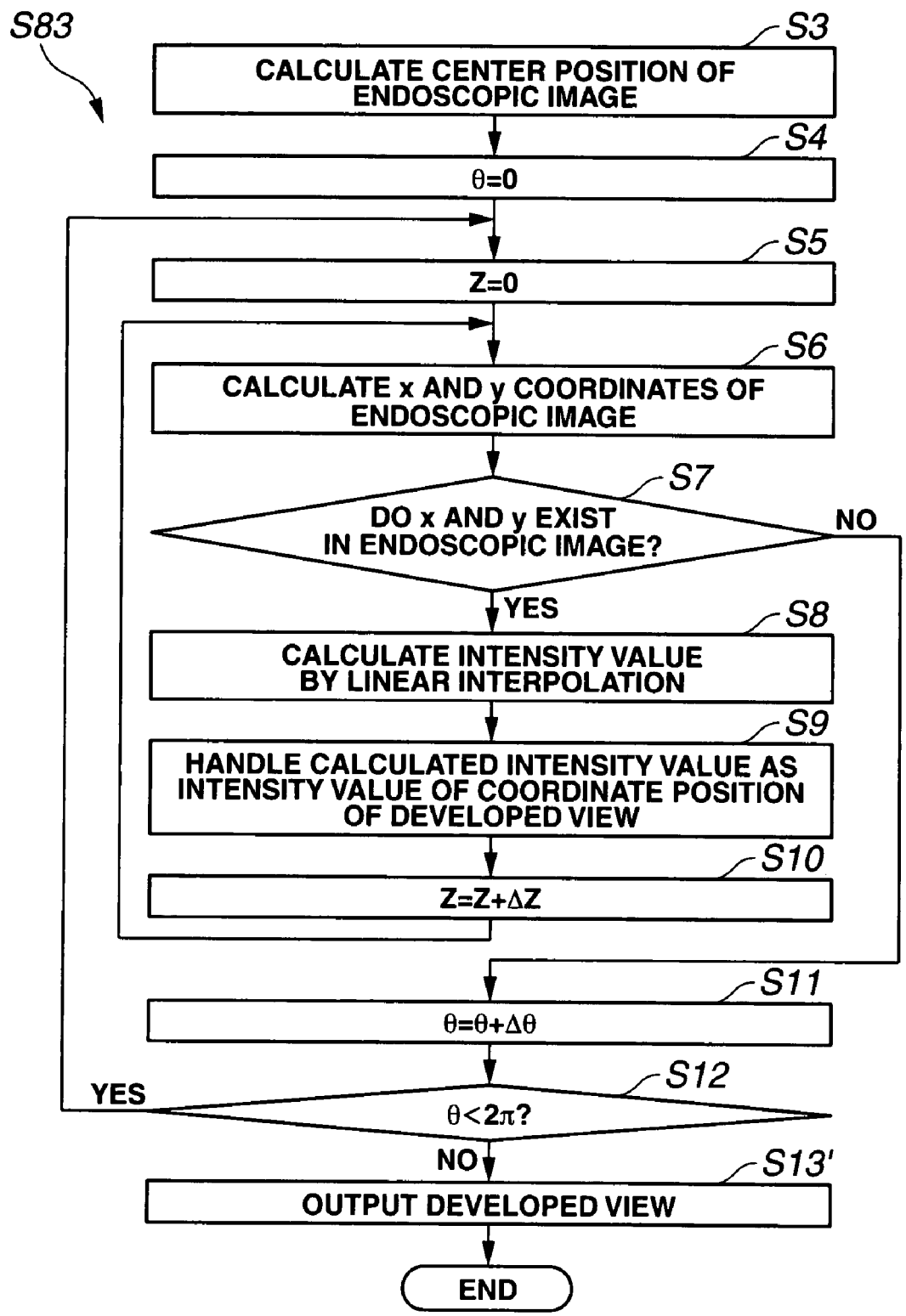
FIG. 39 is a flowchart of processing steps of creating a developed view from an endoscopic image.

The processing in step S83 of creating the developed view Ib is shown in FIG. 39. Since the processing shown in FIG. 39 is the same as the processing in steps S3 through step S13 described with reference to FIG. 5, the same reference numerals are given to the steps having the same processing details. However, step S13' in FIG. 39 is processing outputting a developed view only.

In the first step S3, as shown in FIG. 39, the position of the darkest part within the endoscopic image Ia is detected, and the center of gravity of the detected darkest part is handled as the center position of the coordinates of the endoscopic image Ia.

In the present embodiment, a developed view is created about the position of the darkest part within the endoscopic image Ia. The method for detecting the darkest part includes dividing the endoscopic image Ia into multiple areas, calculating the average intensities of the divided areas, and the area having the lowest average intensity as the position of the darkest part.

As shown in FIG. 38, the two-dimensional orthogonal coordinate system of the endoscopic image Ia is defined as X-Y, and the developed view Ib is created by geometrically converting the coordinate system of the endoscopic image Ia to a polar coordinate system θ-Z. The coordinate position on the coordinate system X-Y are expressed by x and y. The coordinate position on the polar coordinate system θ-Z is expressed by θ, which is a position in the circumferential direction, and z, which is a distance position from the center.

For easy understanding of the relationship in the case when the developed view Ib is created from the endoscopic image Ia, FIG. 6 has arrows indicating correspondences describing the forms on the developed view Ib of the squamocolumnar junction 37 between the squamous epithelium 36 and the columnar epithelium 35 and the esophagogastric junction 34 on the endoscopic image Ia. Here, the O-axis is divided by 0, 45, 90 degrees and so on. The positions of the display frame of the image are indicated by $Q_0$, $Q_{45}$ and $Q_{90}$.

In the next steps S4 and S5, the initial values of the coordinates S(θ,z) of the developed view Ib are defined. In other words, the CPU 22 in step S4 defines θ=0 and in step S5 defines z=0.

The coordinate position of the endoscopic image Ia, which is defined in the next step S6 and corresponds to the coordinates S(θ,z) of the developed view Ib, is calculated by:

$$x = z \sin\theta, \quad y = z \cos\theta \tag{1}$$

Whether the coordinates P(x,y) calculated in step S7 exist within the endoscopic image Ia or not is determined.

If so, the CPU 22 moves to step S8. Since the position at the coordinates P(x,y) of the endoscopic image, which is obtained by (Eq. 1), may possibly exist between pixels, the intensity value of the coordinates P(x,y) is calculated by using the processing such as linear interpolation in step S8.

As the intensity value, the intensity value of each color signal is calculated when the image pickup has been performed in color.

In step S9, the intensity value obtained in step S8 is handled as the intensity value at the coordinates S(θ,z) of the developed view. Then, in step S10, the value z of the developed view Ib is changed (such as the increment of z: Δz=1), and the CPU 22 returns to step S6.

On the other hand, if the coordinates P(x,y) calculated in step S7 do not exist within the endoscopic image Ia, the CPU 22 moves to step S11 and changes the value θ of the developed view Ib (such as the increment of θ: Δθ=π/180, that is, 1°). The CPU 22 in the next step S12 returns to step S5 if θ is smaller than 2π (360°) and continues the processing of creating the developed view. On the other hand, if θ is equal to or larger than 2π, the CPU 22 determines that the developed view Ib has been created and moves to step S13 to output the developed view Ib to the monitor 4 and exits the processing of developed-view creation and moves to processing of detecting the squamocolumnar junction 37 in step S84 in FIG. 37 by using the created developed view Ib.

Figure 37:
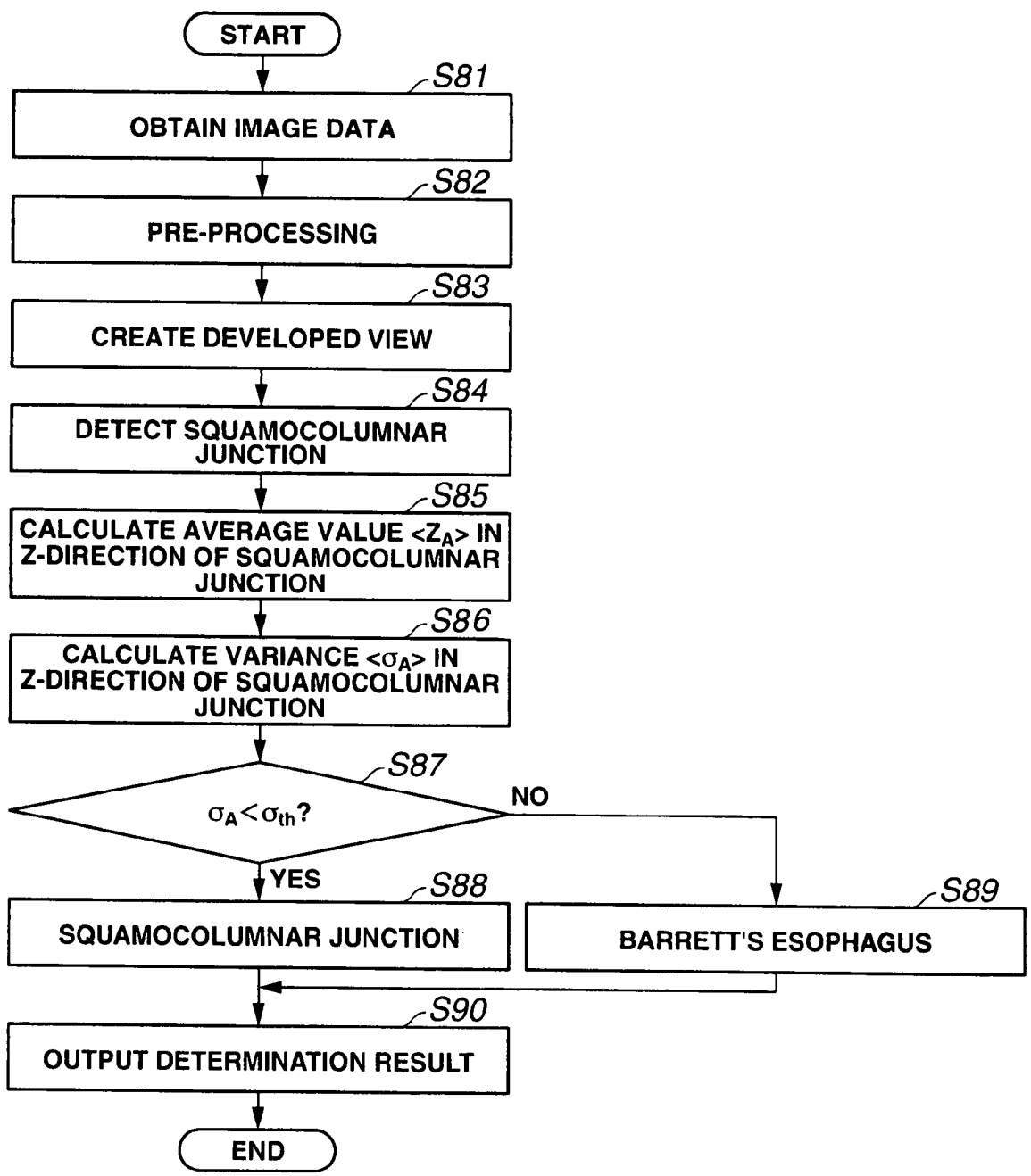
FIG. 37 is a flowchart showing processing steps for determining whether Barrett's esophagus through processing of creating a developed view or not.
Figure 40:
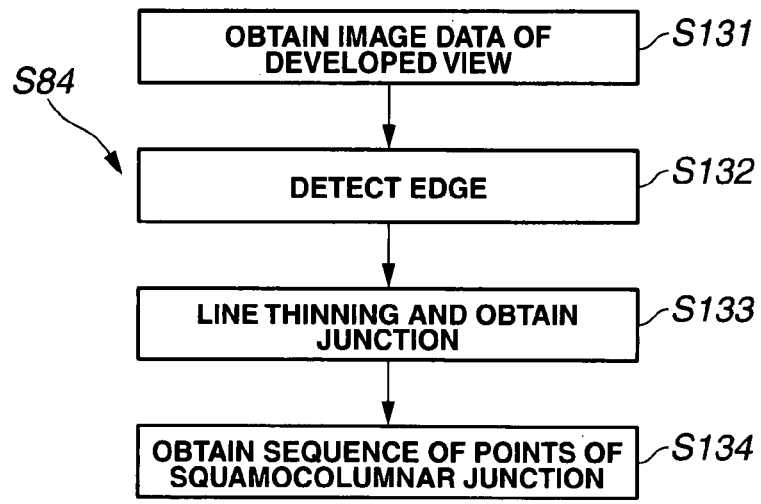
FIG. 40 is a flowchart of processing steps of detecting the squamocolumnar junction in FIG. 37.

In order to detect (obtain the sequence of coordinate points of) the squamocolumnar junction 37 as the junction between the squamous epithelium 36 and the columnar epithelium 35 shown in step S84 in FIG. 37, edge detection, for example, is applied as shown in FIG. 40. Since the squamous epithelium 36 appears with a white tone while the columnar epithelium 36 appears with a red tone, the squamocolumnar junction 37 can be detected from a specific tone in RGB color signals, for example.

As shown in FIG. 40, the CPU 22 in step S131 obtains image data of the developed view Ib stored in the image storage section 24.

Then, the CPU 22 in the next step S132 performs processing of the publicly known edge detection as the contour extracting/filtering processing on the image data and creates an edge-detected image.

The CPU 22 in the next step S1133 performs binarizing processing and line-thinning processing on the edge-detected image and obtains the junction.

The CPU 22 in the next step S1134 performs trace processing on the obtained junction and obtains the sequence of coordinate points along the junction, that is, the sequence of points at the squamocolumnar junction.

After the sequence of points on the squamocolumnar junction 37 is obtained in this way, the CPU 22 calculates the average value $\langle Z_A \rangle$ in the Z-direction (which is the direction of the luminalis of the esophagus) of the squamocolumnar junction 37 as described in step S85 in FIG. 37.

In other words, the CPU 22 obtains the average value $\langle Z_A \rangle$ in the Z-direction of the detected squamocolumnar junction 37 by:

[EQ 24]

$$\langle Z_A \rangle = \frac{1}{N} \sum_{i=0}^{N-1} Z_{A\theta_i} \quad (25)$$

where $Z_{A\theta i}$ is the value Z at $\theta i$ on the squamocolumnar junction on the developed view obtained by (Eq. 1). From (Eq. 25), the average is calculated from a sample value N for one rotation in the circumferential direction (where the resolution of the developed view Ib in FIG. 38 depends on the degree of details of the sampling of $\theta i$ and Z (which are distances from the center O).

Figure 41:
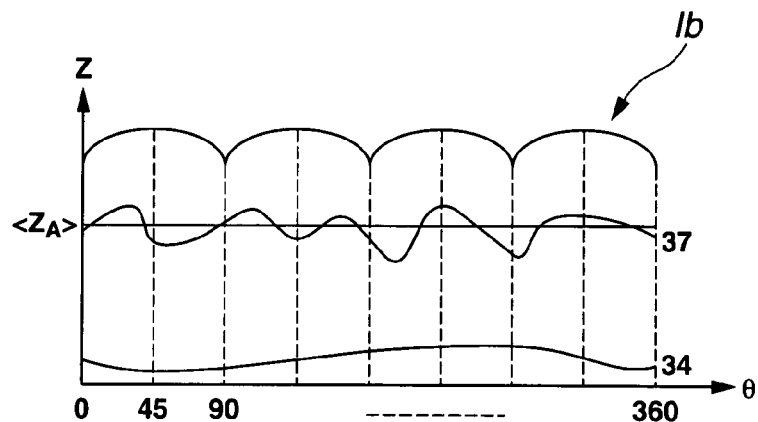
FIG. 41 is a diagram showing a developed view displaying the calculated average values in Z direction of the squamocolumnar junction.

FIG. 41 shows an example in which an average value $\langle Z_A \rangle$ in the Z-direction of the squamocolumnar junction 37 is displayed on the developed view Ib. After the average value $\langle Z_A \rangle$ is calculated from (Eq. 25), the CPU 22 in the next step S86 obtains a variance $\sigma_A$ expressing the degree of variations (pits and projections at the junction) at coordinate positions in the Z-direction of the squamocolumnar junction 37 by:

[EQ 25]

$$\sigma_A = \frac{1}{N} \sum_{i=0}^{N-1} (Z_{A\theta_i} - \langle Z_A \rangle)^2 \quad (26)$$

The CPU 22 in the next step S87 compares the variance $\sigma_A$ calculated by (Eq. 26) and a reference value $\sigma_{th}$ and determines whether the variance $\sigma_A$ is smaller than the reference value $\sigma_{th}$ or not.

If the variance $\sigma_A$ is smaller than the reference value $\sigma_{th}$, the CPU 22 in step S88 determines the squamocolumnar junction 37. On the other hand, if the variance $\sigma_A$ is larger than the reference value $\sigma_{th}$, the CPU 22 in step S89 determines that the squamocolumnar junction 37 has a complex form and determines the picked up image as Barrett's esophagus.

Figure 42:
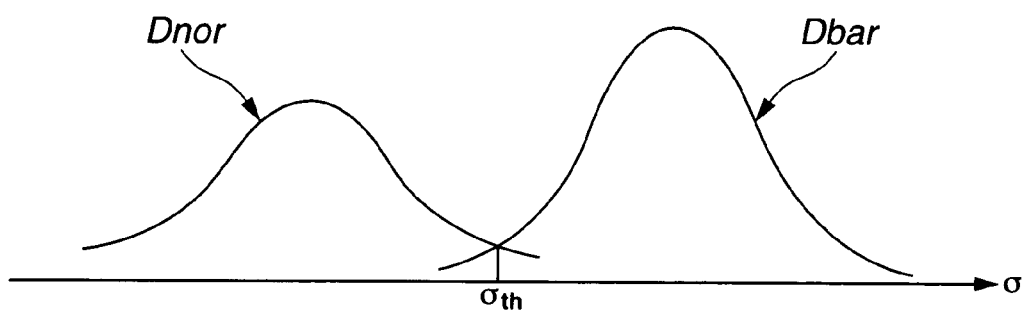
FIG. 42 is a diagram showing a histogram example in which a reference value, which functions as a criterion, is calculated from a histogram of distributed values of samples in a case of the squamocolumnar junction which has been already diagnosed and a case of Barrett's esophagus.

In this case, the reference value $\sigma_{th}$ to be used for the variance $\sigma_A$ obtained from the developed view Ib is determined by the histogram of the variance a based on the use of a sample of the squamocolumnar junction 37 and a sample of Barrett's esophagus, the diagnoses of which have been already confirmed, as shown in FIG. 42.

FIG. 42 shows a histogram $D_{nor}$ of the distribution of variances $\sigma_{nor}$, which can be obtained for the case of the squamocolumnar junction 37 and a histogram $D_{bar}$ of the distribution of variances $\sigma_{bar}$, which can be obtained for the case of Barrett's esophagus. Notably, the sample for the case of Barrett's esophagus is a sample having a complex junction form such as serration at the squamocolumnar junction 37. Based on the two histograms $D_{nor}$ and $D_{bar}$ as shown in FIG. 42, the reference value $\sigma_{th}$ may be determined for evaluating the position $\sigma_{th}$ where the two histograms cross as Barrett's esophagus, for example.

By comparing the variance $\sigma_A$, which is obtained by (Eq. 26) as described above with the reference value $\sigma_{th}$, the CPU 22 determines either squamocolumnar junction 37 or Barrett's esophagus.

The CPU 22 in step S90 outputs the information on the determination result (analysis result) by step S88 or S89 to a display device such as the monitor 4 and exits the processing.

Figure 43:
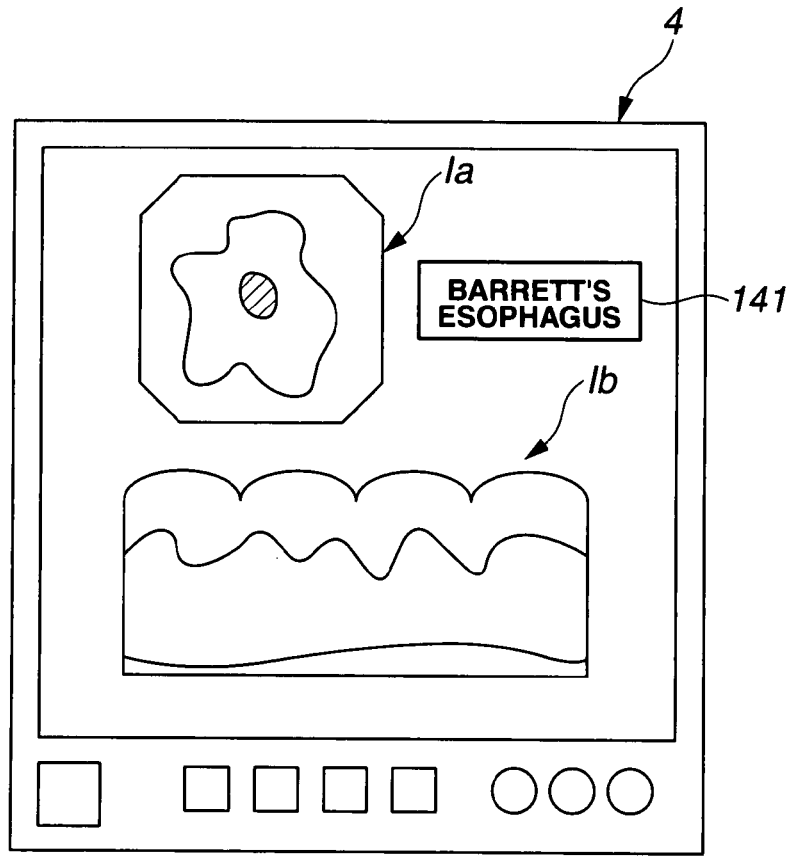
FIG. 43 is a diagram showing a display example on a monitor displaying an endoscopic image, a developed view and a determination result.

FIG. 43 shows a display example displaying the endoscopic image Ia, developed view Ib and information on a determination result on the monitor 4. In the display example in FIG. 43, the determination result determining "Barrett's esophagus" is displayed at a determination indicating section 41 as an example of the case that the variance $\sigma_A$ is equal to or larger than the reference value $\sigma_{th}$.

Notably, while the name "Barrett's esophagus" is displayed here, an expression "highly possibly Barrett's esophagus" may be displayed, for example, instead. Alternatively, the standard deviation value may be calculated and compared with a reference value instead of the variance $\sigma_A$, and the comparison result may be displayed as an analysis result.

Having described that the comparison result from the comparison between the evaluation value for a feature value of Barrett's esophagus to be determined, such as the calculated variance $\sigma_A$, and a single reference value (such as $\sigma_{th}$) is handled as an analysis result in the present and subsequent embodiments, the analysis result may be outputted which is in (one or more) medium state(s) between a state having a high possibility of Barrett's esophagus and a state close to the normal based on the comparison between the calculated evaluation value and multiple reference values.

For example, when it is determined that the squamous epithelium 36 functioning as the gastric mucosa is slightly denatured instead of the squamocolumnar junction 37, a determination result indicating the initial state that the columnar epithelium (Barrett's mucosa) 35 is slightly formed or indicating that a symptom that the columnar epithelium (Barrett's mucosa) 35 is largely formed is developing if it is determined that the squamous epithelium 36 has been further denatured may be displayed for a notice, for example.

A surgeon can perform an efficient diagnosis with reference to the information on the determination result. In addition, with reference to the developed view Ib displayed along with the endoscopic image Ia displayed on the monitor 4, a surgeon can more easily grasp the circumferential form, for example, of the squamocolumnar junction 37 (than the case with the endoscopic image Ia only), which therefore results in an efficient diagnosis.

Figure 44A:
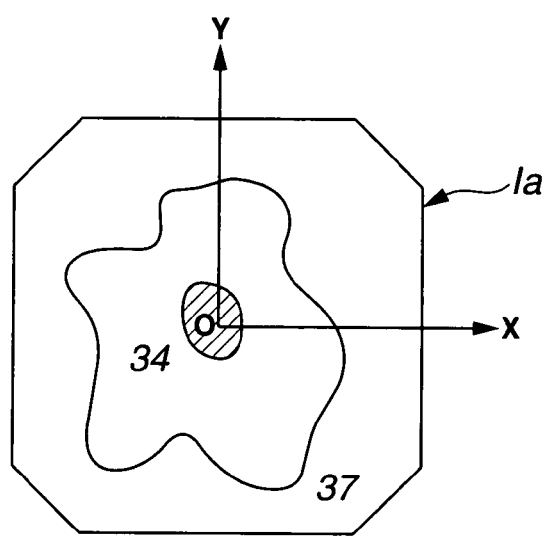
FIG. 44A is a diagram showing an endoscopic image obtained by a direct-view type endoscope.
Figure 44B:
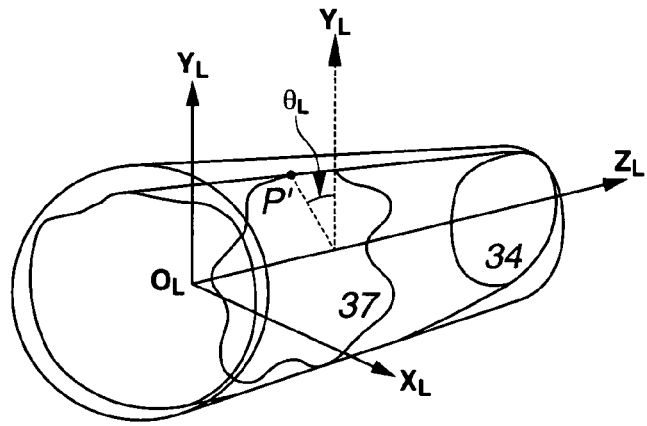
FIG. 44B is an explanatory diagram showing a relationship between the endoscopic image in FIG. 44A and the surface of a cylinder modeling the esophagus.
Figure 44C:
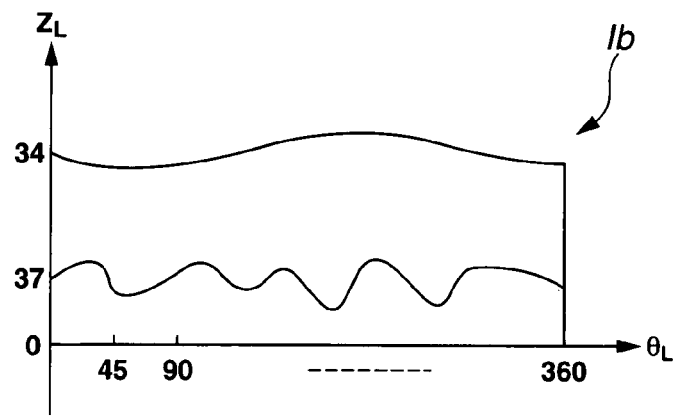
FIG. 44C is a diagram showing a developed view created from an endoscopic image projected on the surface of the cylinder in FIG. 44B.

Having described the case that the developed view Ib is created by geometric conversion from the two-dimensional image Ia by the processing as shown in FIG. 39 above, the developed view Ib shown in FIG. 44C may be created after the three-dimensional form of the surface of the inner wall of the margin of the esophagogastric junction of the esophagus to be diagnosed as shown in FIG. 44B is estimated from the endoscopic image Ia shown in FIG. 44A.

When the three-dimensional form is estimated as in FIG. 44B, the center line of the three-dimensional form may be estimated, the points on the endoscopic image Ia may be converted to the three-dimensional coordinate system $(X_L, Y_L, Z_L)$ with the coordinate axis $Z_L$ in the direction of the center line.

The points of the three-dimensional form on the three-dimensional coordinate system $(X_L, Y_L, Z_L)$ are projected to the surface of a cylinder about the same $Z_L$, which is close to the three-dimensional form. The coordinate system of the surface of the cylinder is $\theta_L$-$Z_L$. The points on the three-dimensional coordinate system $(X_L, Y_L, Z_L)$ or the points projected to the surface of the cylinder are converted to the coordinate system $\theta_L$-$Z_L$.

FIG. 44B shows a point P' on the squamocolumnar junction 37, and the angle formed by the point P' on the squamocolumnar junction 37 and the $Y_L$-axis is indicated by $\theta_L$.

As shown in FIG. 44B, after each point projected to the surface of the cylinder is converted to the coordinate system $\theta_L$-$Z_L$ and then is developed by $\theta_L$ being equal to zero. Then, the position on the endoscopic image Ia is displayed on the developed view Ib shown in FIG. 44C. This processing has been described in more detail in Embodiment 4.

Alternatively, the developed-view creating means in Embodiment 5 may be adopted to create a developed view. (The developed-view creating means in Embodiment 2 or 3 may be adopted to create a developed view by two-dimensional conversion, and the developed view may be used to perform the processing).

In this case, as shown in FIG. 44C, since the side having a higher $Z_L$ is farther away from the image pickup means, the form of the squamocolumnar junction 37 is displayed below (inside of) the esophagogastric junction 34 corresponding to the far position.

In this way, also from the developed view Ib shown in FIG. 44C, either squamocolumnar junction or Barrett's esophagus resulting from a change in property can be determined by calculating the average value $<Z_A>$ and variance $\sigma_A$ in the Z-direction (that is, ZL-direction in FIG. 44C) of the squamocolumnar junction 37 and comparing the variance $\sigma_A$ with a reference value $\sigma_{th}$ by performing processing in step S84 and subsequent steps in FIG. 37. The resolution of the developed view Ib in FIG. 44C depends on the resolution of an image for estimating a three-dimensional form to be diagnosed.

In this way, according to the present embodiment, whether Barrett's esophagus or not can be easily and objectively determined by creating the developed view Ib of an endoscopic image of the esophagus, which is picked up by the direct-view endoscope 6, and quantitatively determining a variation, for example, of the form of the squamocolumnar junction 37 on the developed view Ib.

Therefore, a surgeon can use the determination result to efficiently perform a diagnosis on whether Barrett's esophagus or not.

Since the developed view Ib is created in the present embodiment, a surgeon can more easily grasp the form distribution, for example, of the squamocolumnous junction 37 in the direction of the luminalis or in the circumferential direction orthogonal to the luminalis than the case with the endoscopic image Ia only, which allows the surgeon to easily perform a diagnosis.

Embodiment 7

Figure 45:
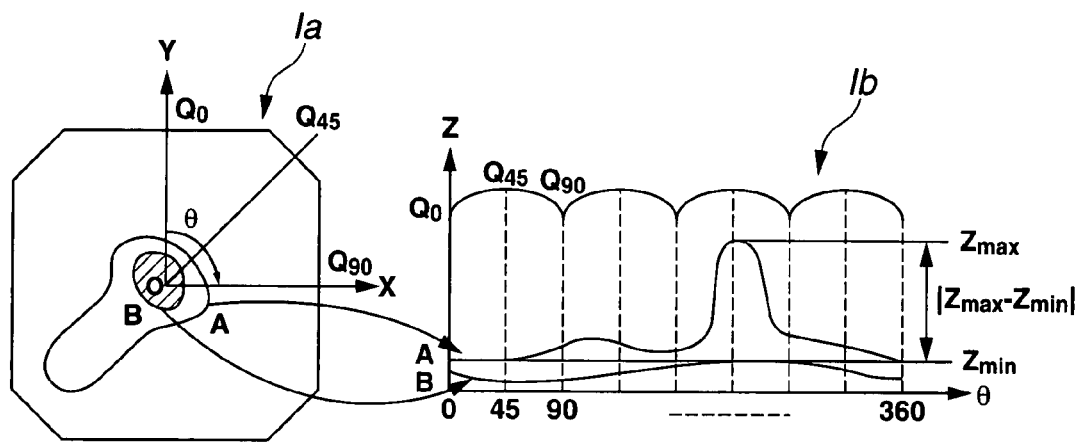
FIG. 45 is a diagram showing an endoscopic image and a developed view in Embodiment 7 of the present invention.
Figure 46:
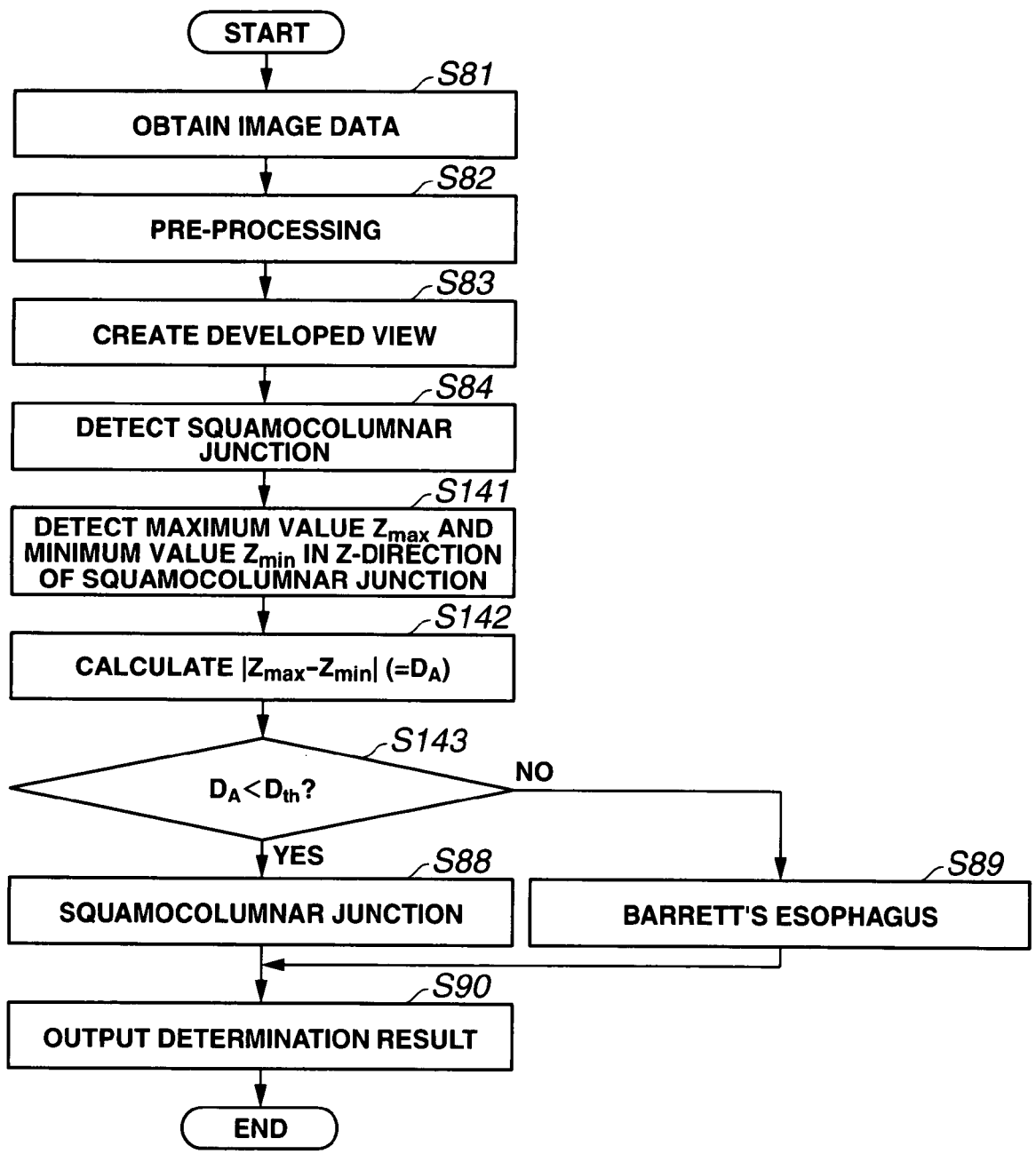
FIG. 46 is a flowchart showing processing steps for determining whether Barrett's esophagus through processing of creating a developed view or not.

With reference to FIGS. 45 and 46, Embodiment 7 will be described next. While Barrett's esophagus is applied to the squamocolumnar junction 37 having a complex form, as described in Embodiment 6, the columnar epithelium (Barrett's mucosa) 35 may extend in a tang-like shape, and the form of the squamocolumnar junction 37 may therefore be in a tang-like shape.

In this case, it may be difficult to output a proper analysis result for the form according to Embodiment 6. Therefore, the object of the present embodiment is to allow outputting a proper analysis result (determination result) even when the columnar epithelium 35 extends in a tang-like shape.

Accordingly, according to the present embodiment, instead of the calculation of the average value $<Z_A>$ in the Z-direction of the squamocolumnar junction 37 and calculation of the variance $\sigma_A$ corresponding to a variation (complexity) in the Z-direction of the squamocolumnar junction 37 in Embodiment 6, whether the squamocolumnar junction 37 is Barrett's esophagus or not is determined by obtaining maximum and minimum values in the Z-direction of the squamocolumnar junction 37 and comparing the absolute value of the difference therebetween with a reference value, as described later.

FIG. 45 shows an endoscopic image Ia resulting from the pickup of an image of the esophagogastric junction and the vicinity and a developed view Ib created two- or three-dimensionally from the endoscopic image Ia.

In the present embodiment, the processing as shown in FIG. 46 is performed. The processing in steps S81 through step S84 in FIG. 46 is the same as the processing in FIG. 37. After the squamocolumnar junction 37 is detected in step S84, the CPU 22 in step S141 calculates a maximum value Zmax and a minimum value Zmin in the Z-direction of the squamocolumnar junction 37 in the present embodiment.

The CPU 22 in the next step S142 obtains the absolute value $D_A$ of the difference between the maximum value Zmax and the minimum value Zmin.

The CPU 22 in the next step S143 compares the absolute value $D_A$ of the difference with a reference value $D_{th}$ and determines whether the absolute value $D_A$ of the difference is smaller than the reference value $D_{th}$ or not.

From the calculated histograms of the absolute values of the differences of a normal sample the diagnosis of which has been confirmed and a sample of Barrett's esophagus in which the squamocolumnar junction 37 extends in a tang-like shape, the reference value $D_{th}$ is calculated as a threshold value suitable for the determination of both of them.

If the absolute value $D_A$ of the difference is smaller than the reference value $D_{th}$, the CPU 22 in step S88 determines the squamocolumnar junction 37. If the absolute value $D_A$ of the difference is equal to or larger than the reference value $D_{th}$, the CPU 22 in step S89 determines Barrett's esophagus. Then, the CPU 22 in step S90 may output the result of the determination in step S88 or S89 to a display device such as the monitor 4 and exits the processing.

According to the present embodiment, accurate determination can be performed by properly analyzing even the characteristic of Barrett's esophagus, if any, that the squamocolumnar junction 37 extends in a tang-like shape, for example.

Embodiment 8

Figure 47:
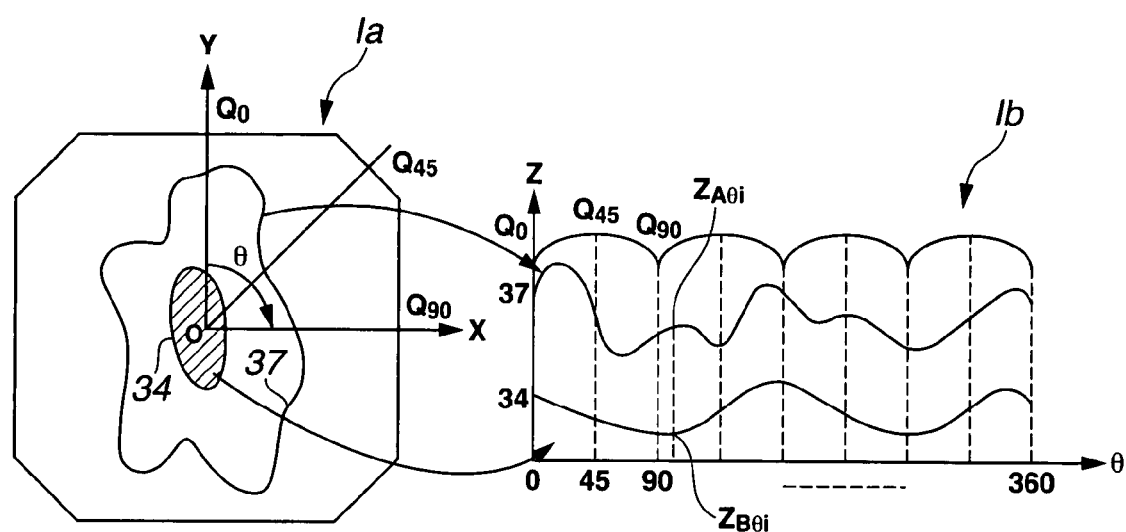
FIG. 47 is a diagram showing an endoscopic image and a developed view in Embodiment 8 of the present invention.
Figure 48:
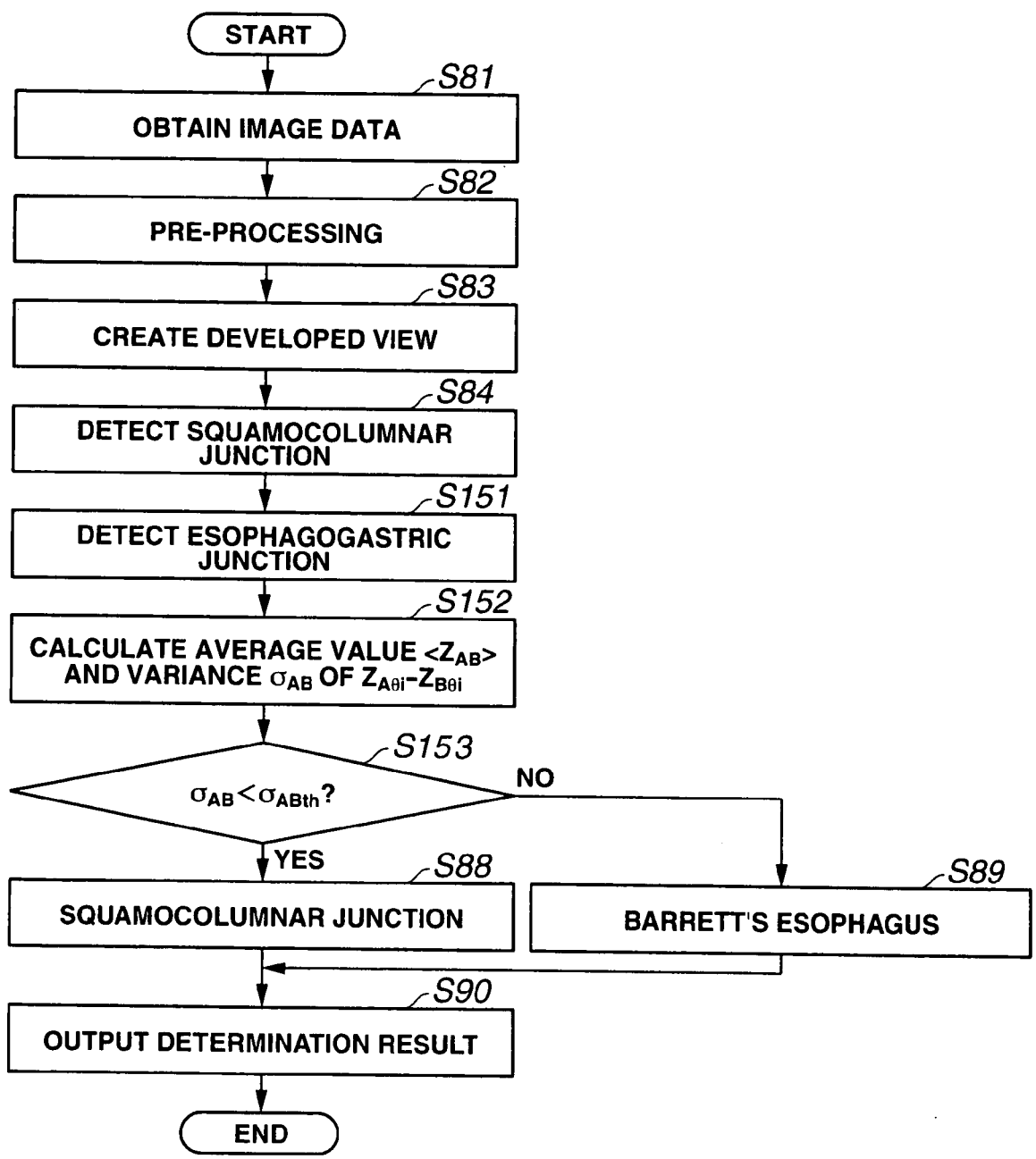
FIG. 48 is a flowchart showing processing steps for determining whether Barrett's esophagus through processing of creating a developed view or not.

With reference to FIGS. 47 and 48, Embodiment 8 of the present invention will be described next. The object of the present embodiment is to properly determine Barrett's esophagus from a distinctive form of the squamocolumnar junction even when a tubular form of the esophagus results from deformation of a circular tubular form, for example.

The determination method of Embodiment 6 includes assuming that the esophagus is close to a circular tubular form, calculating the average value $<Z_A>$ in the Z-direction of the squamocolumnar junction 37, calculating a variation (variance) from the average value $<Z_A>$ for each position in the Z-direction of the squamocolumnar junction 37, and determining Barrett's esophagus. In this method, when the tubular form of the esophagus results from deformation from a circular tubular form due to an effect of heart beats or other effects, for example, the determination result is susceptible to the effects.

In order to reduce the effects, the present embodiment includes creating a developed view Ib on the right side in FIG. 47 from an endoscopic image Ia shown on the left side, detecting the esophagogastric junction 34, for example, on the developed view Ib, and determining Barrett's esophagus from a variance of the distance from the esophagogastric junction 34 to the squamocolumnar junction 37.

In other words, when the tubular form of the esophagus is denatured, the esophagogastric junction 34 may be also denatured in the same manner. Therefore, by using the distance information from the esophagogastric junction 34 to the squamocolumnar junction 37, the determination is allowed, which is hardly affected by the tubular form of the esophagus. In this case, a dark part connecting to the stomach or the cardia may be detected and used instead of the esophagogastric junction 34.

The esophagogastric junction 34 can be detected by detecting the end points of palisade blood vessels traveling in the direction of the luminalis (that is, in the Z-direction) of the esophageal mucosa and connecting the end points.

The processing method of the present embodiment is as shown in FIG. 48. Steps S81 to S84 in FIG. 48 are the same as those in FIG. 37 or 46. The CPU 22 in step S151 after step S84 performs processing of detecting the esophagogastric junction 34 and detects the esophagogastric junction B34.

The CPU 22 in the next step S1152 calculates the average value $<Z_{AB}>$ and variance $\sigma_{AB}$ of the distance $Z_{A\theta i}$-$Z_{B\theta i}$ in the Z-direction between the squamocolumnar junction 37 and the esophagogastric junction 34.

Here, the average value $<Z_{AB}>$ and variance $\sigma_{AB}$ can be obtained by:

[EQ 26]

[EQ 26]

$$\langle Z_{AB} \rangle = \frac{1}{N} \sum_{i=0}^{N-1} (Z_{A\theta_i} - Z_{B\theta_i}) \quad (27)$$

$$\sigma_{AB} = \frac{1}{N} \sum_{i=0}^{N-1} (Z_{A\theta_i} - Z_{B\theta_i} - \langle Z_{AB} \rangle)^2$$

Then, the CPU 22 in the next step S153 determines either squamocolumnar junction or Barrett's esophagus resulting from a changed property by comparing the variance $\sigma_{AB}$ and a reference variance $\sigma_{ABth}$ to be used for determination, which has been calculated in advance.

In other words, if the variance $\sigma_{AB}$ is smaller than the reference variance $\sigma_{ABth}$ in step S153, the CPU 22 in step S88 determines the squamocolumnar junction. On the other hand, if the variance $\sigma_{AB}$ is equal to or larger than the reference variance $\sigma_{ABth}$, the CPU 22 in step S89 determines Barrett's esophagus.

Then, the CPU 22 in step S90 outputs the determination result in step S88 or S89 to display the determination result on the monitor 4 and exits the processing.

According to the present embodiment, whether the squamocolumnar junction 37 is the squamocolumnar junction or Barrett's esophagus is determined by calculating the average value $<Z_{AB}>$ of the distance (=$Z_{A\theta i}$-$Z_{B\theta i}$) to the squamocolumnar junction 37 with reference to the esophagogastric junction 34 and evaluating the variation of the distance $Z_{A\theta i}$-$Z_{B\theta i}$. Therefore, the determination can be performed properly even when the tubular form of the esophagus is deformed.

Instead of the reference to the esophagogastric junction 34, the determination may be performed with reference to a dark part connecting to the stomach or the cardia. For example, in order to detect a dark part (darkest part), the edge of the dark part can be detected by binarizing based on a threshold value defined for detecting a dark part, detecting the border by edge extraction and performing line-thinning.

In this case, simpler processing may be performed to calculate than the case for detecting the esophagogastric junction 34.

Embodiment 9

Figure 49:
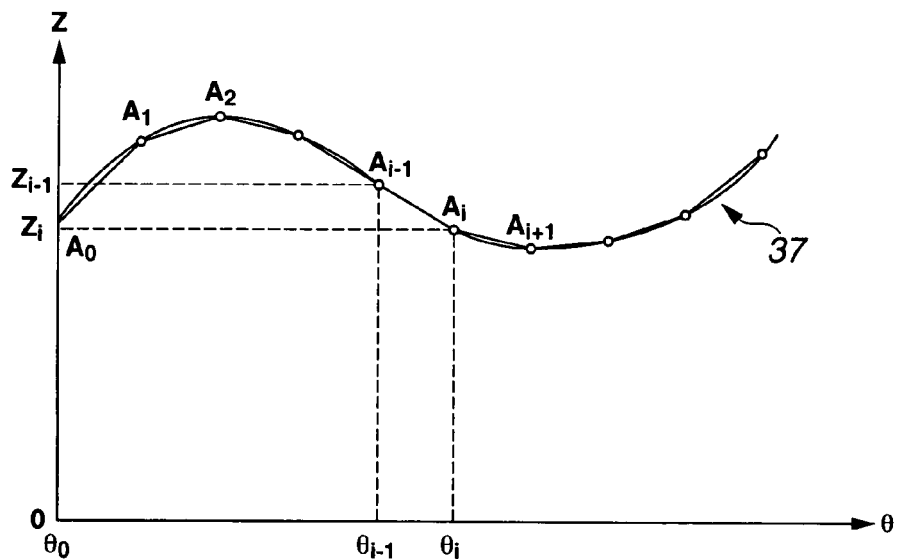
FIG. 49 is an explanatory diagram for a case that the distance between two adjacent points at the squamocolumnar junction in a developed view in Embodiment 9 is calculated.
Figure 50:
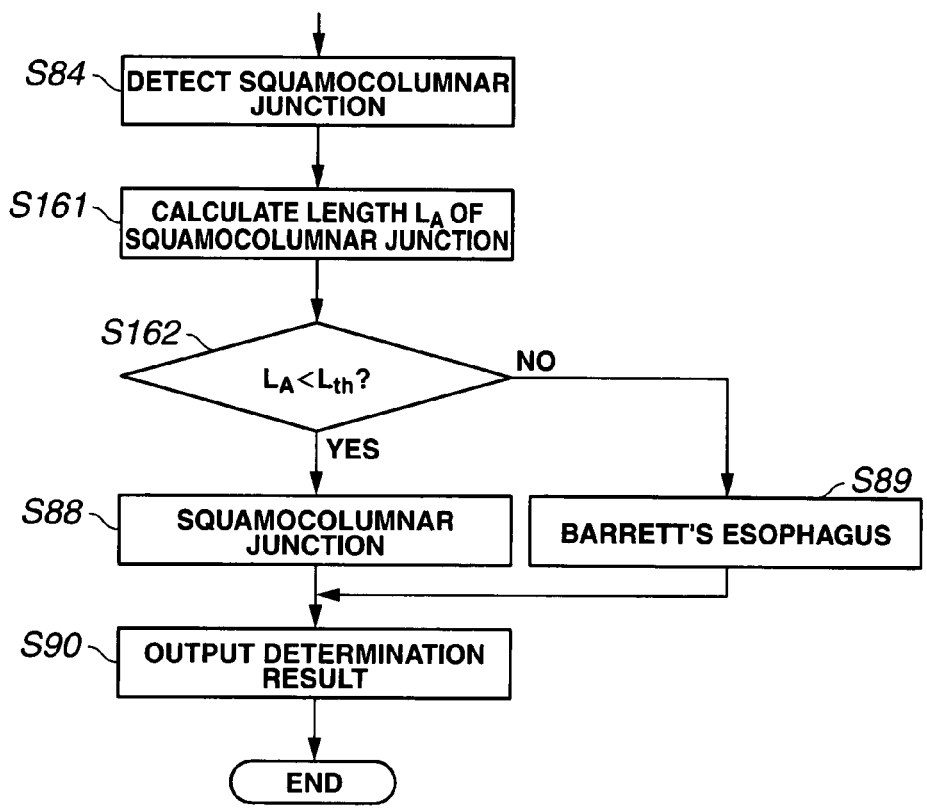
FIG. 50 is a flowchart showing processing steps for determining whether Barrett's esophagus by calculating the total sum of the distances between adjacent two points at the squamocolumnar junction or not.

With reference to FIGS. 49 and 50, Embodiment 9 of the present invention will be described next. By focusing on the characteristic that the squamocolumnar junction 37 of Barrett's esophagus has a complex form, either squamocolumnar junction or Barrett's esophagus is determined from the characteristic by calculating the length of the squamocolumnar junction 37.

FIG. 49 shows a developed view Ib created from an endoscopic image as in the embodiments above. Since the developed view Ib is a discrete image, the curved line of the squamocolumnar junction 37 is expressed by a polyline in reality. Therefore, the line length $L_A$ of the squamocolumnar junction 37 can be obtained by calculating the distance $L_{i-,i}$ between adjacent two points $A_{i-1}(\theta_{i-1}, Z_{i-1})$ and $A_i(\theta_i, Z_i)$ and obtaining the total sum value of the distance $L_{i-1,i}$ as in:

[EQ 27]

$$L_{i-1,i} = \sqrt{(\theta_i - \theta_{i-1})^2 + (Z_i - Z_{i-1})^2} \quad (28)$$

$$L_A = \sum_{i=1}^{N} L_{i-1,i}$$

where i is a value from one (1) to N when 360 degrees (2π) is divided into N.

The calculated length $L_A$ of the squamocolumnar junction 37 is used to determine either squamocolumnar junction or Barrett's esophagus by the steps shown in FIG. 50. Since the steps S81 to S83 are the same as those in FIG. 37, they are omitted in FIG. 50.

After the detection of the squamocolumnar junction 37 by the step S84 as shown in FIG. 50, the CPU 22 in step S161 calculates the length $L_A$ of the squamocolumnar junction 37.

The CPU 22 in the next step S1162 compares the calculated length $L_A$ of the squamocolumnar junction 37 with the length $L_{th}$ of the squamocolumnar junction, which is a reference to be used for determination based on many samples the diagnoses of which have been confirmed. If the length $L_A$ is smaller than the reference length $L_{th}$ of the squamocolumnar junction 37, the CPU 22 in step S88 determines the squamocolumnar junction. If the length $L_A$ is equal to or larger than the reference length $L_{th}$ of the squamocolumnar junction, the CPU 22 in step S89 determines Barrett's esophagus.

Then, the CPU 22 in step S90 outputs the determination result in step S88 or S89 to display on the monitor 4 and exits the processing.

According to the present embodiment, Barrett's esophagus can be determined accurately since there are many cases that the squamocolumnar junction 37 has a complex form.

Notably, in order to calculate the length $L_A$ of the squamocolumnar junction 37, the curved line of the squamocolumnar junction 37 may be expressed by an approximate expression, and the line length may be calculated by the approximate expression. Thus, a highly accurate line length can be calculated, and the determination based on the line length can be performed with high accuracy.

Having described that the length $L_A$ of the squamocolumnar junction 37 is calculated from the total sum value of the distance $L_{i-1,i}$ between adjacent two points $A_{i-1}(\theta_{i-1}, Z_{i-1})$ and $A_i(\theta_i, Z_i)$ for the entire circumference (360 degrees) in the circumferential direction, the present embodiment is not necessarily limited to the entire circumference. This is also true for other embodiments.

Embodiment 10

Figure 51A:
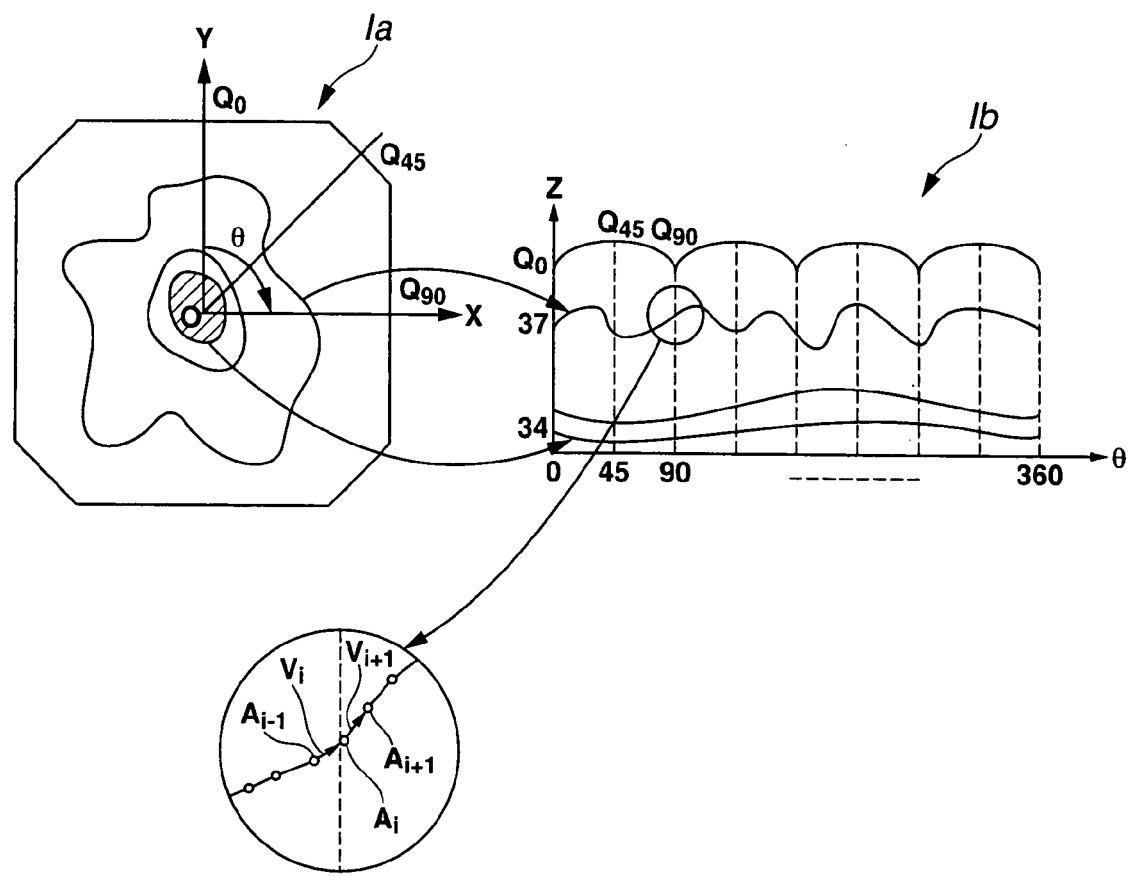
FIG. 51A is an explanatory diagram showing a state that vectors are defined at the squamocolumnar junction in the developed view created from an endoscopic image in Embodiment 10.
Figure 51B:
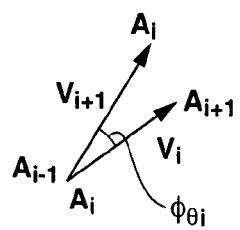
FIG. 51B is an explanatory diagram showing a state that the angle formed by adjacent two vectors is calculated from adjacent three points at the squamocolumnar junction of a developed view.
Figure 52:
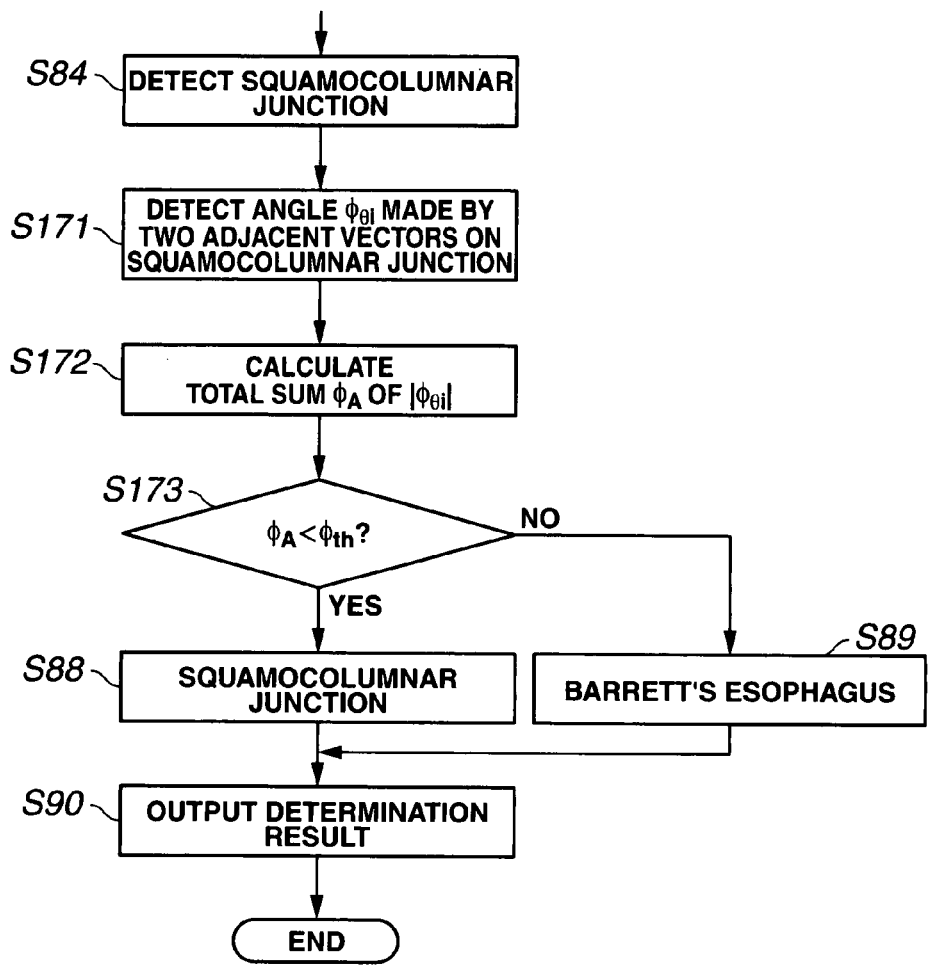
FIG. 52 is a flowchart showing processing steps for determining whether Barrett's esophagus by calculating the total sum of angles made by adjacent two vectors or not.

With reference to FIGS. 51A to 52, Embodiment 10 of the present invention will be described next. According to the present embodiment, the total sum value in the circumferential direction of the absolute values of the angle formed by adjacent vectors on the curved lines of the squamocolumnar junction, and either squamocolumnar junction or Barrett's esophagus is determined based on the total sum value.

Also in the present embodiment, the CPU 22 creates a developed view Ib on the right side of FIG. 51A from an endoscopic image Ia shown on the left side. The CPU 22 detects the squamocolumnar junction 37 from the developed view Ib. Since the developed view Ib is a discrete image, the squamocolumnar junction 37 is expressed by a polyline.

Adjacent three points on the squamocolumnar junction 37 are extracted, and the angle formed by two line segments each connecting adjacent two points, or the angle formed by two vectors is obtained.

For example, as shown in the enlarged view of a part of the circle C in FIG. 51A, the vectors $V_i$ and $V_{i+1}$ at three points $A_{i-1}$, $A_i$ and $A_{i+1}$ are shown in FIG. 51B.

Then, the CPU 22 calculates the angle $\phi_{\theta i}$ formed by both of the vectors $V_i$ and $V_{i+1}$.

Then, the CPU 22 moves the three points $A_{i-1}$, $A_i$ and $A_{i+1}$ to the left side so as to increment i by one from zero and calculates the total sum $\phi_{Ai}$ of the absolute values of the angle $\phi_{\theta i}$ in that case by:

[EQ 28]

$$\phi_{\theta i} = \cos^{-1} \frac{V_i \cdot V_{i+1}}{|V_i||V_{i+1}|} \quad (29)$$

$$\phi_A = \sum_{i=0}^{N-1} |\phi_{\theta i}|$$

The method for determining either squamocolumnar junction or Barrett's esophagus in the present embodiment is as shown in FIG. 52. Since the first steps S81 through step S83 are also the same as those in FIG. 37, the steps are omitted in FIG. 52.

After the detection of the squamocolumnar junction 37 by the step S84, the CPU 22 in the next step S171 defines two vectors $V_i$ and $V_{i+1}$ sequentially from adjacent three points on the developed view Ib as described in FIGS. 51A and 51B and calculates the angle $\phi_{\theta i}$ formed thereby. Then, the CPU 22 in the next step S172 calculates the total sum $\phi_A$ of the absolute values of the angles $\phi_{\theta i}$.

The CPU 22 in the next step S173 compares the calculated total sum $\phi_A$ with the total sum value $\phi_{th}$ of the squamocolumnar junction, which is a reference calculated based on many samples the diagnoses of which have been confirmed. If the calculated total sum $\phi_A$ is smaller than the reference total sum value $\phi_{th}$, the CPU 22 in step S88 determines the squamocolumnar junction. If the calculated total sum $\phi_A$ is equal to or larger than the reference total sum value $\phi_{th}$, on the other hand, the CPU 22 in step S89 determines Barrett's esophagus.

Then, the CPU 22 in step S90 outputs the determination result in step S88 or S89 to display on the monitor 4 and exits the processing.

According to the present embodiment, Barrett's esophagus can be determined accurately since there are many cases that the squamocolumnar junction 37 has a complex form.

Embodiment 11

Figure 53:
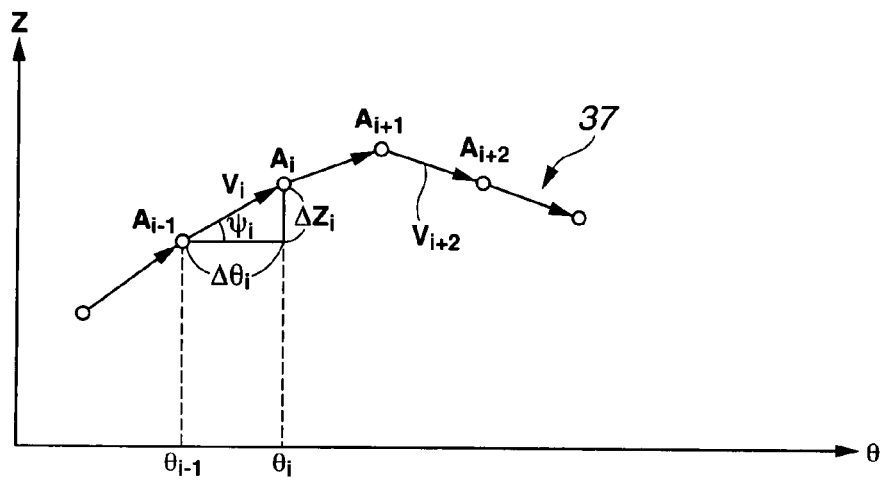
FIG. 53 is an explanatory diagram showing a state that the gradient of the vector connecting adjacent two points at the squamocolumnar junction in a developed view in Embodiment 11 is calculated.
Figure 54:
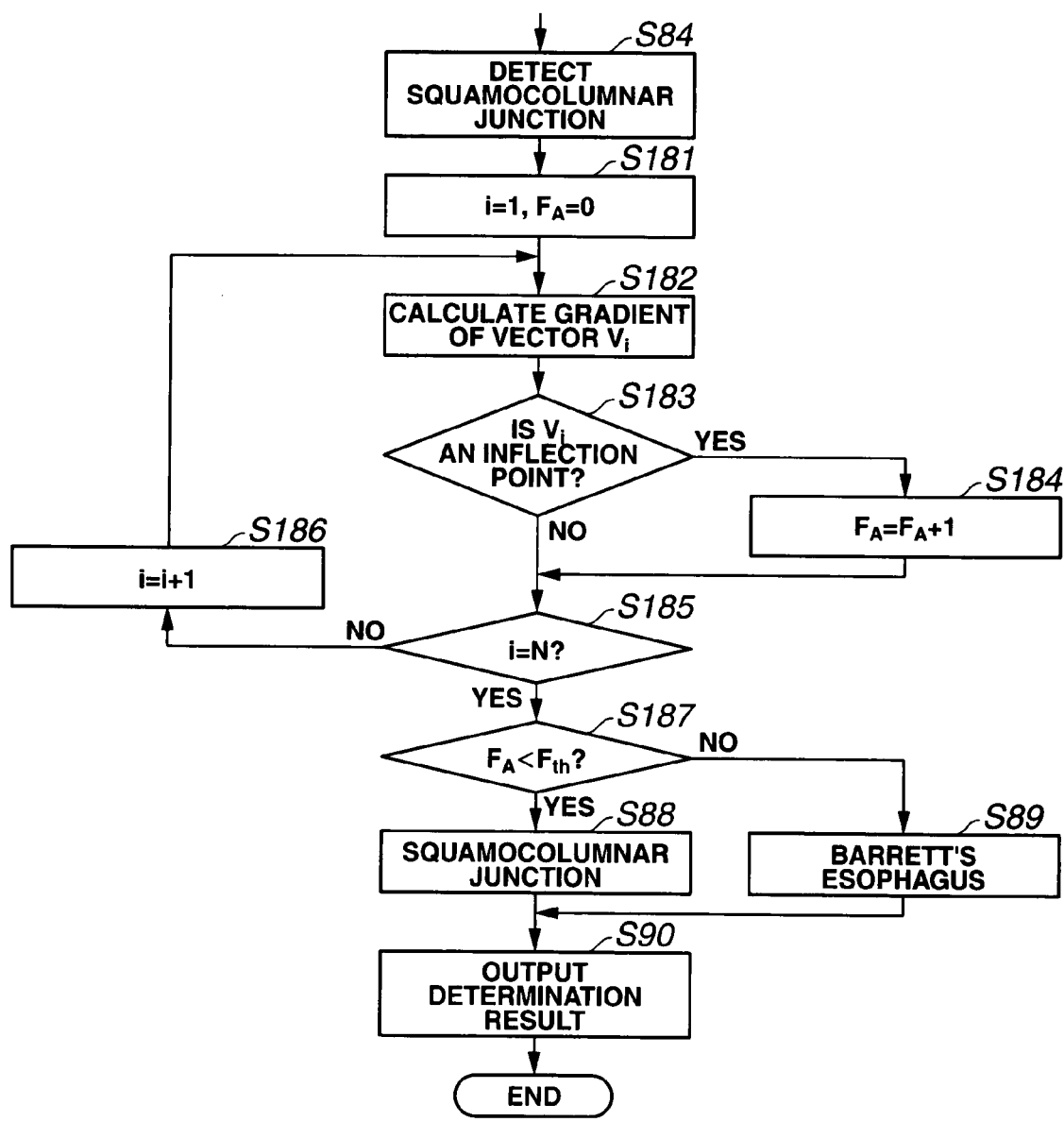
FIG. 54 is a flowchart showing processing steps for calculating the total number of inflection points where the gradient of a vector changes from positive to negative or from negative to positive and from the total number, determining whether Barrett's esophagus or not.

With reference to FIGS. 53 and 54, Embodiment 11 of the present invention will be described next. In the present embodiment, the number of inflection points on the squamocolumnar junction is calculated, and either squamocolumnar junction or Barrett's esophagus is determined based on the magnitude of the number. As described above, there are many cases of Barrett's esophagus having a complex form such as serration. For example, as shown in FIG. 51A, the squamocolumnar junction 37 may often have pits and projection forms in a case of Barrett's esophagus.

In the present embodiment, specifically for calculating (evaluating) the number of break points, the number of inflection points corresponding to maximum and minimum values of the squamocolumnar junction 37 on a developed view may be calculated. Alternatively, the number of points may be calculated where the angle formed by the line segment or vector connecting adjacent two points on the squamocolumnar junction 37 on a developed view and the horizontal direction is changed from the state beyond zero degree to zero degree or below (a positive value to a negative value) or from the degree below zero degree to zero degree or above (a negative value to a positive value). The state is shown in FIG. 53.

As shown in FIG. 53, the numbers of the point where the gradient $\Delta Z_i/\Delta \theta_i = \Psi_i$ of the vector $V_i$ of the two points $A_{i-1}$ and $A_i$ on the squamocolumnar junction 37 is changed from a positive value to a negative value and the inflection points from a negative value to a positive value are calculated. In FIG. 53, since the gradient of the vector $V_{i+2}$ is negative, the point $A_{i+2}$ is determined as the inflection point.

Then, the detection of inflection points is performed in cases where i of $\theta$i is equal to 1 to N, and the total sum of the inflection points is calculated. Based on the magnitude of the total sum value of the inflection points, either squamocolumnar junction or Barrett's esophagus is determined.

The method for determining either squamocolumnar junction or Barrett's esophagus in the present embodiment is as shown in FIG. 54. Since the first step S81 to S83 are the same as those of FIG. 37, the steps are omitted in FIG. 54.

After the detection of the squamocolumnar junction 37 in step S84, the CPU 22 in the next step S181 initializes a variable parameter i of $\theta$ and the number $F_A$ of inflection points. In other words, the CPU 22 defines i=1 and $F_A=0$. The CPU 22 in the next step S182 calculates the gradient $\Psi_i$ of the vector $V_i$ as shown in FIG. 53. Then, the CPU 22 in the next step S183 determines whether the gradient $\Psi_i$ is an inflection point or not. If it is determined so, the CPU 22 in step S184 increments the value of the number $F_A$ by one and then moves to the next step S185.

If the CPU 22 in the determination processing in step S183 determines not, the CPU 22 moves to step S185. The CPU 22 in step S185 determines whether the variable parameter i is equal to the number N of divisions of θ or not. If not, the CPU 22 increments the number of the variable parameter i by one in step S186 and returns to step S182.

In this way, the CPU 22 repeats the processing from steps S182 to S186 up to i=N.

Then, when i=N, the CPU 22 in step S187 determines whether the number $F_A$ is smaller than a reference number $F_{th}$ or not. The reference number $F_{th}$ is calculated from many samples the diagnoses of which have been confirmed.

Then, if the number $F_A$ is smaller than the reference number $F_{th}$, the CPU 22 in step S88 determines the squamocolumnar junction. If the number $F_A$ is equal to or larger than the reference number $F_{th}$, the CPU 22 in step S89 determines Barrett's esophagus.

Then, the CPU 22 in step S90 outputs the determination result of step S88 or S89 to display on the monitor 4 and exits the processing.

According to the present embodiment, Barrett's esophagus can be determined accurately since there are many cases that the squamocolumnar junction 37 has a complex form.

Having described in the present embodiment the case that either squamocolumnar junction or Barrett's esophagus is determined by calculating the number $F_A$ of inflection points and comparing the calculated number, either squamocolumnar junction or Barrett's esophagus may be determined by calculating and comparing the number of break points as disclosed in Japanese Unexamined Patent Application Publication No. 2004-360319.

The determination method only requires performing processing in steps S4 through S14 in FIG. 4 in Japanese Unexamined Patent Application Publication No. 2004-360319. In this case, the processing is performed on image data obtained from an endoscopic image.

Having described the example in which either squamocolumnar junction or Barrett's esophagus is determined by calculating the number $F_A$ of inflection points or the number of break points and comparing the number with a reference value, the determination may be performed by comparing the values of adjacent two gradients $\Psi_i$ and $\Psi_{i+1}$ and counting the number of points where the value changes (for example, points where the subtracted value varies) and comparing the total sum value with a reference value.

Having described that the squamocolumnar junction 37 is detected in step S84 after a developed view is created in the step S83 therebefore in the processing steps in FIG. 37, for example, the developed view Ib may be created after the squamocolumnar junction 37 is detected first.

Having described the case Barrett's esophagus is quantitatively determined as a disease in the margin of the esophagogastric junction within the esophagus functioning as an upper digestive tract in the embodiments above, the same is also applicable to a lower digestive tract.

For example, a developed view may be created from an image picked up by the endoscope 6 inserted to the large intestine, and the junction of the mucosa of a lesion, which is different in tone from a normal part, may be detected from the developed view. Then, the detected junction may be analyzed on the form of the junction, for example, to obtain the analysis result. In other words, the present invention is widely applicable to an apparatus and method for creating a developed view from an endoscopic image resulting from the pickup of an image of a tubular part within a body and performing an analysis on a lesion from the developed view. In this case, by also using the analysis result along with the developed view, a lesion, for example, may be easily grasped, which may allow performing a diagnosis efficiently. Embodiments including partial combinations of the embodiments above belong to the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical image processing apparatus comprising:
   an image conversion section including a coordinate-system converting section for converting an image in an orthogonal coordinate system to an image in a polar coordinate system, for geometrically converting a medical image of a tubular part in vivo picked up and obtained by the coordinate-system converting section;
   a squamocolumnar junction detecting section for detecting a squamocolumnar junction that is a junction between a squamous epithelium and a columnar epithelium on the image of the polar coordinate system;
   an analyzing section for comparing an evaluation value for a feature value determined for the detected squamocolumnar junction and a predetermined reference value and calculating an analysis result; and
   an estimating section for estimating a relative positional relationship between an image pickup apparatus and the tubular part,
   wherein the medical image is a picked-up image, which is picked up by the image pickup apparatus, the image pickup apparatus being a direct-view type image pickup apparatus having the direction of the field of vision in the longitudinal direction of the tubular part.

2. The medical image processing apparatus according to claim 1, further comprising a developed-view output section for outputting the image in the polar coordinate system obtained by the image conversion section to a display device as an image of a developed view.

3. The medical image processing apparatus according to claim 2, further comprising the display device displaying an image of the developed view.

4. The medical image processing apparatus according to claim 1, wherein the image conversion section creates the image in the polar coordinate system by projecting the picked-up image to the surface of a cylinder.

5. The medical image processing apparatus according to claim 1, further comprising a center-position defining section defining the center position of the picked-up image.

6. The medical image processing apparatus according to claim 5, wherein the center-position defining section detects the darkest part within the picked-up image and handles the center of gravity of the detected darkest part as the center position.

7. The medical image processing apparatus according to claim 1, further comprising a distortion/aberration correcting section correcting a distortion/aberration of the medical image.

8. The medical image processing apparatus according to claim 1, wherein the estimating section detects a model image close to the picked-up image actually picked up by the image pickup apparatus from multiple model images obtained in states with definition of multiple different positional relationships between the tubular part and the image pickup apparatus and thus estimates the positional relationship for the detected model image.

9. The medical image processing apparatus according to claim 1, further comprising a three-dimensional form estimating section estimating a three-dimensional form of the tubular part from the picked-up image.

10. The medical image processing apparatus according to claim 9, wherein the image conversion section performs geometric conversion to project the picked-up image to the surface of the three-dimensional form estimated by the three-dimensional form estimating section and creates the image in the polar coordinate system.

11. The medical image processing apparatus according to claim 10, further comprising:
 a developed-view output section for outputting the image in the polar coordinate system obtained by the image conversion section as an image of a developed view; and
 a display device for displaying the image of the developed view created from the image in the polar coordinate system by the image conversion section.

12. The medical image processing apparatus according to claim 9, wherein the three-dimensional form estimating section estimates a three-dimensional form of the tubular part from evolution equations on curved lines on the surface, which are considered as being apart from illumination means by an equal distance.

13. The medical image processing apparatus according to claim 1, wherein the developed-view output section has an interpolation processing section performing interpolation processing on the image in the polar coordinate system and outputting an image of the developed view.

14. The medical image processing apparatus according to claim 1, wherein the analyzing section calculates the analysis result using a feature value of the form of the squamocolumnar junction in a Barrett's esophagus as the predetermined feature value.

15. The medical image processing apparatus according to claim 1, further comprising a direct-view type endoscope including the image pickup apparatus, the longitudinal direction of an insertion section of which is the direction of the field of vision.

16. The medical image processing apparatus according to claim 1, further comprising a developed-view output section for outputting the image in the polar coordinate system obtained by the image conversion section to a display device as an image of a developed view,
 wherein the developed-view output section creates an image of a developed view corresponding to an image resulting from the development of the inner circumferential surface of the tubular part from the picked-up image.

17. A medical image processing apparatus comprising:
 an image conversion section including a coordinate-system converting section for converting an image in an orthogonal coordinate system to an image in a polar coordinate system, for geometrically converting a medical image of a tubular part in vivo picked up and obtained by the coordinate-system converting section;
 a squamocolumnar junction detecting section for detecting a squamocolumnar junction that is a junction between a squamous epithelium and a columnar epithelium on the image of the polar coordinate system;
 an analyzing section for comparing an evaluation value for a feature value determined for the detected squamocolumnar junction and a predetermined reference value and calculating an analysis result; and
 a three-dimensional form estimating section for estimating a three-dimensional form of the tubular part from the medical image,
 wherein the medical image is a picked-up image, which is picked up by a direct-view type image pickup apparatus having the direction of the field of vision in the longitudinal direction of the tubular part, and
 the three-dimensional form estimating section estimates image pickup positions and the three-dimensional form of the tubular part based on a movement amount of one same subject part between/among multiple picked-up images picked up at different image pickup positions.

18. A medical image processing apparatus comprising:
 an image conversion section including a coordinate-system converting section for converting an image in an orthogonal coordinate system to an image in a polar coordinate system, for geometrically converting a medical image of a tubular part in vivo picked up and obtained by the coordinate-system converting section;
 a squamocolumnar junction detecting section for detecting a squamocolumnar junction that is a junction between a squamous epithelium and a columnar epithelium on the image of the polar coordinate system;
 an analyzing section for comparing an evaluation value for a feature value determined for the detected squamocolumnar junction and a predetermined reference value and calculating an analysis result;
 a three-dimensional form estimating section for estimating a three-dimensional form of the tubular part from the medical image, and
 a straight-line estimating section estimating a straight line passing through the near/close center of a three-dimensional form estimated by the three-dimensional form estimating section.

19. The medical image processing apparatus according to claim 18, further comprising a conversion parameter calculating section calculating a conversion parameter for conversion from a coordinate system representing a three-dimensional form estimated by the three-dimensional form estimating section to the coordinate system based on the straight line.

20. A medical image processing apparatus comprising:
 an image conversion section including a coordinate-system converting section for converting an image in an orthogonal coordinate system to an image in a polar coordinate system, for geometrically converting a medical image of a tubular part in vivo picked up and obtained by the coordinate-system converting section;
 a squamocolumnar junction detecting section for detecting a squamocolumnar junction that is a junction between a squamous epithelium and a columnar epithelium on the image of the polar coordinate system; and
 an analyzing section for comparing an evaluation value for a feature value determined for the detected squamocolumnar junction and a predetermined reference value and calculating an analysis result,
wherein:
 the medical image is a picked-up image, which is picked up by a direct-view type image pickup apparatus having the direction of the field of vision in the longitudinal direction of the tubular part, and the analyzing section has an average value calculating section calculating the average value of the squamocolumnar junction, and an amount-of-variation calculating section calculating an amount of variation from the average value of the squamocolumnar junction and calculating an analysis result corresponding to the predetermined feature value by the calculation of the amount of variation.

21. A medical image processing apparatus comprising:
an image conversion section including a coordinate-system converting section for converting an image in an orthogonal coordinate system to an image in a polar coordinate system, for geometrically converting a medical image of a tubular part in vivo picked up and obtained by the coordinate-system converting section;
a squamocolumnar junction detecting section for detecting a squamocolumnar junction that is a junction between a squamous epithelium and a columnar epithelium on the image of the polar coordinate system; and
an analyzing section for comparing an evaluation value for a feature value determined for the detected squamocolumnar junction and a predetermined reference value and calculating an analysis result,
wherein:
the medical image is a picked-up image, which is picked up by a direct-view type image pickup apparatus having the direction of the field of vision in the longitudinal direction of the tubular part, and
the analyzing section calculates the difference value between a maximum value and a minimum value in the direction of the luminalis of the esophagus at the squamocolumnar junction and handles the comparison result with a predetermined value as the analysis result.

22. A medical image processing apparatus comprising:
an image conversion section including a coordinate-system converting section for converting an image in an orthogonal coordinate system to an image in a polar coordinate system, for geometrically converting a medical image of a tubular part in vivo picked up and obtained by the coordinate-system converting section;
a squamocolumnar junction detecting section for detecting a squamocolumnar junction that is a junction between a squamous epithelium and a columnar epithelium on the image of the polar coordinate system; and
an analyzing section for comparing an evaluation value for a feature value determined for the detected squamocolumnar junction and a predetermined reference value and calculating an analysis result,
wherein:
the medical image is a picked-up image, which is picked up by a direct-view type image pickup apparatus having the direction of the field of vision in the longitudinal direction of the tubular part, and
the analyzing section calculates an amount of variation of the distance from a reference part such as the junction between the stomach and the esophagus to the squamocolumnar junction and compares the calculated amount of variation with a reference value as the analysis result.

23. A medical image processing apparatus comprising:
an image conversion section including a coordinate-system converting section for converting an image in an orthogonal coordinate system to an image in a polar coordinate system, for geometrically converting a medical image of a tubular part in vivo picked up and obtained by the coordinate-system converting section;
a squamocolumnar junction detecting section for detecting a squamocolumnar junction that is a junction between a squamous epithelium and a columnar epithelium on the image of the polar coordinate system; and
an analyzing section for comparing an evaluation value for a feature value determined for the detected squamocolumnar junction and a predetermined reference value and calculating an analysis result,
wherein:
the medical image is a picked-up image, which is picked up by a direct-view type image pickup apparatus having the direction of the field of vision in the longitudinal direction of the tubular part, and
the analyzing section calculates the total sum value of the distances between adjacent two points on the squamocolumnar junction and handles the comparison result from comparison between the calculated total sum value and a reference value as the analysis result.

24. A medical image processing apparatus comprising:
an image conversion section including a coordinate-system converting section for converting an image in an orthogonal coordinate system to an image in a polar coordinate system, for geometrically converting a medical image of a tubular part in vivo picked up and obtained by the coordinate-system converting section;
a squamocolumnar junction detecting section for detecting a squamocolumnar junction that is a junction between a squamous epithelium and a columnar epithelium on the image of the polar coordinate system; and
an analyzing section for comparing an evaluation value for a feature value determined for the detected squamocolumnar junction and a predetermined reference value and calculating an analysis result,
wherein:
the medical image is a picked-up image, which is picked up by a direct-view type image pickup apparatus having the direction of the field of vision in the longitudinal direction of the tubular part, and
the analyzing section calculates the total sum value of the absolute values of the angle formed by two vectors connecting adjacent two points of adjacent three points on the squamocolumnar junction and handles the comparison result from comparison between the calculated total sum value and a reference value as the analysis result.

25. A medical image processing apparatus comprising:
an image conversion section including a coordinate-system converting section for converting an image in an orthogonal coordinate system to an image in a polar coordinate system, for geometrically converting a medical image of a tubular part in vivo picked up and obtained by the coordinate-system converting section;
a squamocolumnar junction detecting section for detecting a squamocolumnar junction that is a junction between a squamous epithelium and a columnar epithelium on the image of the polar coordinate system; and
an analyzing section for comparing an evaluation value for a feature value determined for the detected squamocolumnar junction and a predetermined reference value and calculating an analysis result,
wherein:
the medical image is a picked-up image, which is picked up by a direct-view type image pickup apparatus having the direction of the field of vision in the longitudinal direction of the tubular part, and
the analyzing section calculates the number of break points when the form at points on the squamocolumnar junction has pits and projections in the direction of the luminalis of the esophagus and handles the comparison result from the comparison of the calculated number of break points with a reference value as the analysis result.

26. A medical image processing apparatus comprising:
an image conversion section including a coordinate-system converting section for converting an image in an orthogonal coordinate system to an image in a polar coordinate system, for geometrically converting a medical image of a tubular part in vivo picked up and obtained by the coordinate-system converting section;
a squamocolumnar junction detecting section for detecting a squamocolumnar junction that is a junction between a squamous epithelium and a columnar epithelium on the image of the polar coordinate system; and
an analyzing section for comparing an evaluation value for a feature value determined for the detected squamocolumnar junction and a predetermined reference value and calculating an analysis result,
wherein:
the medical image is a picked-up image, which is picked up by a direct-view type image pickup apparatus having the direction of the field of vision in the longitudinal direction of the tubular part, and
the analyzing section calculates the number of extreme where the form of the squamocolumnar junction is maximum and minimum in the direction of the luminalis of the esophagus and handles the comparison result from the comparison of the calculated number of extreme with a reference value as the analysis result.

27. A medical image processing method comprising:
an image conversion step for geometrically converting a medical image of a tubular part in vivo picked up and obtained by a coordinate-system converting section for converting an image in an orthogonal coordinate system to an image in a polar coordinate system;
a squamocolumnar junction detecting step for detecting a squamocolumnar junction that is a junction between a squamous epithelium and a columnar epithelium on the image of the polar coordinate system; and
an analyzing step for comparing an evaluation value for a feature value determined for the detected squamocolumnar junction and a predetermined reference value and calculating an analysis result,
wherein the image conversion step performs geometric image conversion creating a two-dimensional image resulting from the projection of the medical image to the surface of a cylinder.

28. The medical image processing method according to claim 27, further comprising a developed-view outputting step for outputting the converted image obtained by the image conversion step to a display device as an image of a developed view.

29. The medical image processing method according to claim 27, further comprising a three-dimensional form estimating step of estimating a three-dimensional form of the tubular part from the medical image.

30. The medical image processing method according to claim 29, wherein the image conversion step performs geometric conversion on the medical image to the surface of the three-dimensional form estimated by the three-dimensional form estimating step.

31. The medical image processing method according to claim 27, wherein the analyzing step calculates an analysis result by calculating an evaluation value of a feature value of the squamocolumnar junction in a Barrett's esophagus as the predetermined feature value and comparing the evaluation value with a reference value, which is a reference.

* * * * *